US007196189B2

(12) United States Patent
Roberts et al.

(10) Patent No.: US 7,196,189 B2
(45) Date of Patent: Mar. 27, 2007

(54) LOVE VARIANT REGULATOR MOLECULES

(75) Inventors: Shannon Roberts, Cambridge, MA (US); Amir Sherman, Jerusalem (IL); Joshua Trueheart, Concord, MA (US); G. Todd Milne, Brookline, MA (US); John C. Royer, Lexington, MA (US)

(73) Assignee: Microbia, Inc., Cambridge, MA (US)

( * ) Notice: Subject to any disclaimer, the term of this patent is extended or adjusted under 35 U.S.C. 154(b) by 339 days.

(21) Appl. No.: 10/402,056

(22) Filed: Mar. 28, 2003

(65) Prior Publication Data

US 2004/0191877 A1    Sep. 30, 2004

Related U.S. Application Data

(63) Continuation-in-part of application No. PCT/US02/32248, filed on Oct. 9, 2002.

(60) Provisional application No. 60/328,339, filed on Oct. 9, 2001.

(51) Int. Cl.
*C07H 21/04* (2006.01)
*C12P 1/00* (2006.01)
*C12N 1/00* (2006.01)
*C12N 1/19* (2006.01)
*C12N 1/15* (2006.01)
*C07K 14/00* (2006.01)

(52) U.S. Cl. .................. 536/23.74; 435/41; 435/254.1; 435/254.2; 435/254.11; 536/23.1

(58) Field of Classification Search ...................... None
See application file for complete search history.

(56) References Cited

U.S. PATENT DOCUMENTS

| 4,554,101 | A | 11/1985 | Hopp | |
|---|---|---|---|---|
| 5,849,541 | A * | 12/1998 | Vinci et al. | 435/91.1 |
| 5,888,732 | A | 3/1999 | Hartley et al. | 435/6 |
| 6,391,583 | B1 | 5/2002 | Hutchinson et al. | |
| 6,806,082 | B2 | 10/2004 | Cali et al. | 435/325 |
| 2003/0143705 | A1 | 7/2003 | Roberts et al. | 435/183 |

FOREIGN PATENT DOCUMENTS

| WO | WO00/37629 | 12/1999 |
|---|---|---|
| WO | WO 02/24865 | 3/2002 |

OTHER PUBLICATIONS

Kennedy et al. Modulation of Polyketide Synthase Activity by Accessory Proteins During Lovastatin Biosynthesis. Science 284: 1368-1372. 1999.*
Everett et al. Pendred syndrome is caused by mutations in a putative sulphate transporter gene (PDS). Nature Genetics 17: 411-422, 1997.*
Scott et al. The pendred syndrome gene encodes a chloride-Iodide trasnport protein. Nature Genetics 21: 440-443, 1999.*
Brachmann et al., "Designer Deletion Strains derived from *Saccharomyces cerevisiae* S288C: . . . " Yeast 14:115-132, 1998.

Drocourt et al., "Cassettes of the *Streptoalloteichus hindustanus* ble gene . . . " Nucl. Acids Res. 18(13):4009, 1990.
Hoffman et al., "A ten-minute DNA preparation from yeast efficiently releases autonomous plasmids . . . " Gene 57:267-272, 1987.
Mumberg et al., "Regulatable promoters of *Saccharomyces cerevisiae*; . . . " Nucl. Acids Res. 22(25):5767-5768, 1994.
Myers et al., "Yeast shuttle and integrative vectors with multiple cloning sites suitable for construction of *lacZ* fusions" Gene 45:299-310, 1986.
Sikorski et al., "A system of shuttle vectors and yeast host strains designed for efficient manipulation of DNA in *Saccharomyces cerevisiae*" Genetics 122:19-27, 1989.
Woods et al., "High-efficiency transformation of plasmid DNA into yeast" Methods in Mol. Biol. 177:85-97, 2001.
Xiao et al., "Conditional gene targeted deletion by Cre recombinase demonstrates . . . " Nucl. Acids Res. 25(15):2985-2991, 1997.
Kyte et al. (1982), "A Simple Method for Displaying the Hydropathic Character of a Protein," *Mol. Biol.* 157:105-132.
Muhlrad et al. (1992), "A Rapid Method for Localized Mutagenesis of Yeast Genes," *Yeast* 8:79-82.
Su et al. (1993), "Identification of Functionally Related Genes That Stimulate Early Meiotic Gene Expression in Yeast," *Genetics* 133:67-77.
Woloshuk et al. (1994), "Molecular Characterization of aflR, a Regulatory Locus for Aflatoxin Biosynthesis," *Appl. Environ. Microbiol.* 60:2408-2414.
Tilburn et al. (1995), "The Aspergillus PacC zinc finger transcription fator mediates regulation of both acid and alkaline- expressed genes by ambient pH," 14 *EMBO J.* 4:779-790.
Brown et al. (1996), "Twenty-five coregulated transcripts define a sterigmatocystin gene cluster in *Aspergillus nidulans*," *Proc. Natl. Acad. Sci. USA* 93:1418-1422.
MacCabe et al. (1996), "Identification, cloning and analysis of the *Aspergillus niger* gene pacC, a wide domain regulatory gene responsive to ambient pH," *Mol. Gen. Genet.* 250:367-374.
Suarez et al. (1996), "Characterization of a *Penicillium chrysogenum* gene encoding a PacC transcription factor and its binding sites in the divergent pcbAB-pcbC promoter of the penicillin biosynthetic cluster," *Mol. Microbiol.* 20:529-540.
Lambert et al. (1997), "Genetic Analysis of Regulatory Mutants Affecting Synthesis of Extracellular Proteinases in the Yeast Yarrowia lipolytica: Identification of a RIM101 /pacC Homolog," *Mol. Cell Biol.* 17:3966-3976.
Trapp et al. (1998), "Characterization of the gene cluster for biosynthesis of macrocyclic trichothecenes in *Myrothecium roridum*," *Mol. Gen. Genet.* 257:421-432.

(Continued)

*Primary Examiner*—David Guzo
*Assistant Examiner*—Michele K. Joike
(74) *Attorney, Agent, or Firm*—Fish & Richardson P.C.

(57) ABSTRACT

The invention provides variant regulator proteins of secondary metabolite production and nucleic acids encoding said variant regulator proteins. In particular, the invention provides variant regulator molecules of the lovE protein.

46 Claims, 11 Drawing Sheets

OTHER PUBLICATIONS

Hendrickson et al. (1999), "Lovastatin biosynthesis in *Aspergillus terreus*; characterization of blocked mutants, enzyme activities and a multifunctional polyketide synthase gene," *Chem. Biol.* 6:429-439.

Kennedy et al. (1999), "Modulation of Polyketide Synthase Activity by Accessory Proteins During Lovastatin Biosynthesis," *Science* 284:1368-1372.

Litzka et al. (1999), "Transcriptional control of expression of fungal B-lactam biosynthesis genes," *Antonie van Leeuwenhoek* 75:95-105.

Matsumoto et al. (1999), "The Trichothecene Biosynthesis Regulatory Gene from the Type B Producer Fusarium Strains: Sequence of Tri6 and Its Expression in *Escherichia coli*," *Biosci. Biotechnol. Biochem.* 63:2001-2004.

Hutchinson et al. (2000), "Aspects of Biosynthesis of Non-Aromatic Fungal Polyketides by Iterative Polyketide Synthases," *Antonie van Leeuwenhoek* 78:287-295.

Lesova et al. (2000), "Factors affecting the production of (-)-mitorubrinic acid by *Penicillium funiculosum*," *J. Basic Microbiol.* 40:369-375.

Schmitt et al. (2000), "The Fungal CPCR1 Protein, Which Binds Specifically to B-Lactam Biosynthesis Genes, Is Related to Human Regulatory Factor X Transcription Factors," *J. Biol. Chem.* 275:9348-9357.

Tag et al. (2000), "G-protein signaling mediates differential production of toxic secondary metabolites," *Mol. Microbiol.* 38:658-665.

Brown et al. (2001), "A Genetic and Biochemical Approach to Study Trichothecene Diversity in *Fusarium sporotrichioldes* and *Fusarium graminearum*," *Fungal Genet.* 257:421-432.

Sutherland et al. (2001), "Recent Advances in the Biosynthetic Studies of Lovastatin," 4 *Curr. Opinion in Drug Discovery & Dev.* 2:229-236.

Hajjaj et al. (2001), "Lovastatin Biosynthesis by *Aspergillus terreus* in a Chemically Defined Medium," *Appl. Environ. Microbiol.* 67:2596-2602.

Robinson et al. (2001), "Solid-state fermentation: a promising microbial technology for secondary metabolite production," *Appl. Microbiol. Biotechnol.* 55:284-289.

Waters (2001), "Are We Aggressive Enough in Lowering Cholesterol?" *Am. J. Cardiol.* 88:10F-5F.

Young et al. (2001), "Molecular cloning and genetic analysis of an indolediterpene gene cluster from *Penicillium paxilli*," *Mol. Microbiol.* 39:754-764.

Hendrickson et al., "Lovastatin Biosynthesis in *Aspergillus terreus*: Characterization of Blocked Mutants . . . " Chem. Biol. 6(7):429-39, 1999.

Accession No.:AF151722; GI: 5106754; Hendrickson et al., Jun. 20, 1999.

Accession No.: AAD34559; GI: 4959952; Hutchinson et al., Jun. 2, 1999.

Accession No.: AF141924; GI: 4959940; Hutchinson et al., Jun. 2, 1999.

* cited by examiner

*lovE* VARIANTS INCREASE EXPRESSION OF *lovFp-HIS3p-neo* lovFp-CYCIp-lacZ OF lovE VARIANTS x1

LOVASTATIN CONCENTRATION OF *lovE* VARIANTS IN MF117
(ENZYME INHIBITION ASSAY)

LOVASTATIN CONCENTRATION OF *lovE* VARIANTS IN MF117
(HPLC ASSAY)

LOVASTATIN CONCENTRATION OF *lovE* VARIANTS IN MF117
(HPLC ASSAY)

us 7,196,189 B2

```
                            SEQUENCE LISTING

<160> NUMBER OF SEQ ID NOS: 118

<210> SEQ ID NO 1
<211> LENGTH: 46
<212> TYPE: DNA
<213> ORGANISM: Artificial Sequence
<220> FEATURE:
<223> OTHER INFORMATION: primer

<400> SEQUENCE: 1
ggccatggag gccgctagct cgagtcgacg gcctaggtgg ccagct                       46

<210> SEQ ID NO 2
<211> LENGTH: 46
<212> TYPE: DNA
<213> ORGANISM: Artificial Sequence
<220> FEATURE:
<223> OTHER INFORMATION: primer

<400> SEQUENCE: 2
ggccacctag gccgtcgact cgagctagcg gcctccatgg ccgtac                       46

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
ggcggccgct ctagaactag tctcgagggt acc                                     33

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
ggtaccctcg agactagttc tagagcggcc gcc                                     33

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
cacagcggcc gctcaacctt cccattgggg c                                       31

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
```
caccactagt acgcgggctg attcgac            27

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
caccactagt tatacattat ataaagtaat gtg            33

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
cacaggatcc gtcatctttg ccttcgttta tc            32

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
cgcggatcct attgaacaag atggattgca c            31

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
ccggaattca gaagaactcg tcaagaag            28

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11
acaaaaaagc aggctccaca atggctgcag atcaaggtat            40

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
acaagaaagc tgggttcatg gaggaatatt gttga            35

<210> SEQ ID NO 13
<211> LENGTH: 28
<212> TYPE: DNA
<213> ORGANISM: Artificial Sequence

```
<220> FEATURE:
<223> OTHER INFORMATION: primer

<400> SEQUENCE: 13
ggggatccaa tcgaggtcca cgaccagt                                          28

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
ggggacaagt ttgtacaaaa aagcaggct                                         29

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
ggggatccgc caatggtccc gttcaaac                                          28

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
acaagaaagc tgggttcaca gaatgtttag ctcaa                                  35

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
ggggaccact ttgtacaaga aagctgggt                                         29

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18
gcgatgcccc aagcgcaagc tacgccaatc caggg                                  35

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19
cgtcgcgcca ttcgccattc aggctgcgca actgt                                  35
```

<210> SEQ ID NO 20
<211> LENGTH: 31
<212> TYPE: DNA
<213> ORGANISM: Artificial Sequence
<220> FEATURE:
<223> OTHER INFORMATION: primer

<400> SEQUENCE: 20
ggacctttgc agcataaatt actatacttc t                          31

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
ggcgcgtcca ttcgccattc aggctgcgca actgt                      35

<210> SEQ ID NO 22
<211> LENGTH: 31
<212> TYPE: DNA
<213> ORGANISM: Artificial Sequence
<220> FEATURE:
<223> OTHER INFORMATION: primer

<400> SEQUENCE: 22
taaaactctt gttttcttct tttctctaaa t                          31

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
cagtgagcgc gcgtaatacg actcactata gggcga                     36

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
atacttctat agacacacaa acacaaatac acacac                     36

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
cgcggatccc gtcgttttac aac                                   23

<210> SEQ ID NO 26
<211> LENGTH: 31
<212> TYPE: DNA
<213> ORGANISM: Artificial Sequence
<220> FEATURE:
<223> OTHER INFORMATION: primer

<400> SEQUENCE: 26
cccaagctta ttatttttga caccagacca a                              31

<210> SEQ ID NO 27
<211> LENGTH: 36
<212> TYPE: DNA
<213> ORGANISM: Artificial Sequence
<220> FEATURE:
<223> OTHER INFORMATION: primer

<400> SEQUENCE: 27
ggaagatcta gcatcgtggc caatttcttc tagttt                         36

<210> SEQ ID NO 28
<211> LENGTH: 41
<212> TYPE: DNA
<213> ORGANISM: Artificial Sequence
<220> FEATURE:
<223> OTHER INFORMATION: primer

<400> SEQUENCE: 28
ataagaatgc ggccgctcaa ccttcccatt ggggcgtttg c                   41

<210> SEQ ID NO 29
<211> LENGTH: 37
<212> TYPE: DNA
<213> ORGANISM: Artificial Sequence
<220> FEATURE:
<223> OTHER INFORMATION: primer

<400> SEQUENCE: 29
cacaggatcc agcattatta atttagtgtg tgtattt                        37

<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
caccactagt ctcgagcaga tccgccag                                  28

<210> SEQ ID NO 31
<211> LENGTH: 27
<212> TYPE: DNA
<213> ORGANISM: Artificial Sequence
<220> FEATURE:
<223> OTHER INFORMATION: primer

<400> SEQUENCE: 31
caccactagt acgcgggctg attcgac                                   27

<210> SEQ ID NO 32
<211> LENGTH: 31
<212> TYPE: DNA
<213> ORGANISM: Artificial Sequence
<220> FEATURE:
<223> OTHER INFORMATION: primer

<400> SEQUENCE: 32
cacagcggcc gctcaaacctt cccattgggg c                             31

<210> SEQ ID NO 33

```
<210> SEQ ID NO 33
<211> LENGTH: 35
<212> TYPE: DNA
<213> ORGANISM: Artificial Sequence
<220> FEATURE:
<223> OTHER INFORMATION: primer

<400> SEQUENCE: 33
ggccatcgat acaagtttgt acaaaaaagc tgaac                              35

<210> SEQ ID NO 34
<211> LENGTH: 33
<212> TYPE: DNA
<213> ORGANISM: Artificial Sequence
<220> FEATURE:
<223> OTHER INFORMATION: primer

<400> SEQUENCE: 34
ggcgccctat tacaccactt tgtacaagaa agc                                33

<210> SEQ ID NO 35
<211> LENGTH: 35
<212> TYPE: DNA
<213> ORGANISM: Artificial Sequence
<220> FEATURE:
<223> OTHER INFORMATION: primer

<400> SEQUENCE: 35
cacacgtctc cggcctcaac cttcccattg gggcg                              35

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
cacacagatc tcgtggccaa tttcttctag tttga                              35

<210> SEQ ID NO 37
<211> LENGTH: 37
<212> TYPE: DNA
<213> ORGANISM: Artificial Sequence
<220> FEATURE:
<223> OTHER INFORMATION: primer

<400> SEQUENCE: 37
cacacggatc cacaatgtta cgtcctgtag aaacccc                            37

<210> SEQ ID NO 38
<211> LENGTH: 34
<212> TYPE: DNA
<213> ORGANISM: Artificial Sequence
<220> FEATURE:
<223> OTHER INFORMATION: primer

<400> SEQUENCE: 38
cacagcggcc gcttcattgt ttgcctccct gctg                               34

<210> SEQ ID NO 39
<211> LENGTH: 34
<212> TYPE: DNA
<213> ORGANISM: Artificial Sequence
<220> FEATURE:
<223> OTHER INFORMATION: primer

<400> SEQUENCE: 39
```

```
gcggccgcgg cgcccggccc atgtcaacaa gaat                              34
```

<210> SEQ ID NO 40
<211> LENGTH: 25
<212> TYPE: DNA
<213> ORGANISM: Artificial Sequence
<220> FEATURE:
<223> OTHER INFORMATION: primer

<400> SEQUENCE: 40

```
ccgcggccga gtggagatgt ggagt                                       25
```

<210> SEQ ID NO 41
<211> LENGTH: 469
<212> TYPE: PRT
<213> ORGANISM: Artificial Sequence
<220> FEATURE:
<223> OTHER INFORMATION: synthetically generated variant

<400> SEQUENCE: 41

```
Met Ala Ala Asp Gln Gly Ile Phe Thr Asn Ser Val Thr Leu Ser Pro
  1               5                  10                  15

Val Glu Gly Ser Arg Thr Gly Thr Leu Pro Arg Arg Ala Phe Arg
             20                  25                  30

Arg Ser Cys Asp Arg Cys His Ala Gln Lys Ile Lys Cys Thr Gly Asn
         35                  40                  45

Lys Glu Val Thr Gly Arg Ala Pro Cys Gln Arg Cys Gln Gln Ala Gly
     50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Ala Gln Ala Asp Cys Arg Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285
```

```
Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Pro Tyr Val Asp Pro Leu Thr His Ala Leu Phe Ser
                340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
        370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
        450                 455                 460

Asn Asn Ile Pro Pro
465
```

<210> SEQ ID NO 42
<211> LENGTH: 469
<212> TYPE: PRT
<213> ORGANISM: Artificial Sequence
<220> FEATURE:
<223> OTHER INFORMATION: synthetically generated variant

<400> SEQUENCE: 42

```
Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
                20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
                100                 105                 110

Glu Ser His Ser Ser Asn Thr Ser Trp Gln Phe Leu Asp Pro Pro Asp
            115                 120                 125

Ser Tyr Asp Trp Leu Trp Thr Ser Ile Gly Thr Asp Glu Ala Ile Asp
        130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175
```

-continued

```
Glu Lys Ala Pro Leu Pro Pro Val Ser Ser Asp Ile Ala Arg Ala Ala
            180                 185                 190
Ser Ala Gln Arg Glu Leu Phe Asp Asp Leu Ser Ala Val Ser Gln Glu
        195                 200                 205
Leu Glu Glu Ile Leu Leu Ala Val Thr Val Glu Trp Pro Lys Gln Glu
    210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Thr Ala Ile Ser Glu Leu Leu Leu
        275                 280                 285
Ser Gln Ile Arg Arg Thr Gln Asn Ser His Met Ser Pro Leu Glu Gly
    290                 295                 300
Ser Arg Ser Gln Ser Pro Ser Arg Asp Asp Thr Ser Ser Ser Ser Gly
305                 310                 315                 320
His Gly Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
        355                 360                 365
Ile Thr Leu Gly Val His Ser Ala Gln Gly Ile Ala Ala Ser Ile Ser
    370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
        435                 440                 445
Ile Phe Ser Leu Ala Arg Lys His Lys His Gly Met Leu Arg Asp Leu
    450                 455                 460
Asn Asn Ile Pro Pro
465
```

<210> SEQ ID NO 43
<211> LENGTH: 469
<212> TYPE: PRT
<213> ORGANISM: Artificial Sequence
<220> FEATURE:
<223> OTHER INFORMATION: synthetically generated variant

<400> SEQUENCE: 43

```
Met Ala Ala Asp Gln Gly Ile Phe Thr Asn Ser Val Thr Leu Ser Pro
1               5                   10                  15
Val Glu Gly Ser Arg Thr Gly Thr Leu Pro Arg Arg Ala Phe Arg
            20                  25                  30
Arg Ser Cys Asp Arg Cys His Ala Gln Lys Ile Lys Cys Thr Gly Asn
        35                  40                  45
Lys Glu Val Thr Gly Arg Ala Pro Cys Gln Arg Cys Gln Gln Ala Gly
    50                  55                  60
```

-continued

```
Leu Arg Cys Val Tyr Ser Glu Arg Arg Pro Lys Arg Lys Leu Arg Gln
 65                  70                  75                  80

Ser Arg Val Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Ile Ser Ile Gly Thr Asp Glu Ala Ile Asp
            130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
            275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
450                 455                 460

Asn Asn Ile Pro Pro
465
```

-continued

<210> SEQ ID NO 44
<211> LENGTH: 469
<212> TYPE: PRT
<213> ORGANISM: Artificial Sequence
<220> FEATURE:
<223> OTHER INFORMATION: synthetically generated variant

<400> SEQUENCE: 44

Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Arg Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Gly Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser

```
                    370                 375                 380
Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
                435                 440                 445

Ile Phe Ser Leu Ala Arg Lys His Lys His Gly Met Leu Arg Asp Leu
                450                 455                 460

Asn Asn Ile Pro Pro
465

<210> SEQ ID NO 45
<211> LENGTH: 469
<212> TYPE: PRT
<213> ORGANISM: Artificial Sequence
<220> FEATURE:
<223> OTHER INFORMATION: synthetically generated variant

<400> SEQUENCE: 45

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
                20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
50                  55                  60

Leu Arg Cys Val Tyr Ser Glu Arg Arg Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
                100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
```

-continued

```
                    260                 265                 270
Tyr Ile Leu Asn Val Arg Ile Leu Thr Ala Ile Ser Glu Leu Leu
            275                 280                 285
Ser Gln Ile Arg Arg Thr Gln Asn Ser His Met Ser Pro Leu Glu Gly
        290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
            355                 360                 365
Ile Thr Leu Gly Val His Ser Ala Gln Gly Ile Ala Ala Ser Ile Ser
        370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
                420                 425                 430
Gly Ser Arg Gly Arg Thr Ile Ala Ala Leu Arg Arg Cys Tyr Glu Asp
            435                 440                 445
Ile Phe Ser Leu Ala Arg Lys His Lys His Gly Met Leu Arg Asp Leu
        450                 455                 460
Asn Asn Ile Pro Pro
465

<210> SEQ ID NO 46
<211> LENGTH: 469
<212> TYPE: PRT
<213> ORGANISM: Artificial Sequence
<220> FEATURE:
<223> OTHER INFORMATION: synthetically generated variant

<400> SEQUENCE: 46

Met Ala Ala Asp Gln Gly Ile Phe Thr Asn Ser Val Thr Leu Ser Pro
  1               5                  10                  15
Val Glu Gly Ser Arg Thr Gly Gly Thr Leu Pro Arg Arg Ala Phe Arg
             20                  25                  30
Arg Ser Cys Asp Arg Cys His Ala Gln Lys Ile Lys Cys Thr Gly Asn
         35                  40                  45
Lys Glu Val Thr Gly Arg Ala Pro Cys Gln Arg Cys Gln Gln Ala Gly
     50                  55                  60
Leu Arg Cys Val Tyr Ser Glu Arg Cys Pro Lys Arg Lys Leu Arg Gln
 65                  70                  75                  80
Ser Arg Ala Ala Asp Leu Val Ser Ala Asp Pro Asp Cys Leu His
                 85                  90                  95
Met Ser Ser Pro Pro Val Pro Ser Gln Ser Leu Pro Leu Asp Val Ser
                100                 105                 110
Glu Ser His Ser Ser Asn Thr Ser Arg Gln Phe Leu Asp Pro Pro Asp
            115                 120                 125
Ser Tyr Asp Trp Ser Trp Thr Ser Ile Gly Thr Asp Glu Ala Ile Asp
        130                 135                 140
Thr Asp Cys Trp Gly Leu Ser Gln Tyr Asp Gly Gly Phe Ser Cys Gln
```

```
            145                 150                 155                 160
Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Lys Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Ala Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 47
<211> LENGTH: 469
<212> TYPE: PRT
<213> ORGANISM: Artificial Sequence
<220> FEATURE:
<223> OTHER INFORMATION: synthetically generated variant

<400> SEQUENCE: 47

Met Ala Ala Asp Gln Gly Ile Phe Thr Asn Ser Val Thr Leu Ser Pro
 1               5                  10                  15

Val Glu Gly Ser Arg Thr Gly Gly Thr Leu Pro Arg Arg Ala Phe Arg
                20                  25                  30

Arg Ser Cys Asp Arg Cys His Ala Gln Lys Ile Lys Cys Thr Gly Asn
```

-continued

```
                35                  40                  45
Lys Glu Val Thr Gly Arg Ala Pro Cys Gln Arg Cys Gln Gln Ala Gly
 50                  55                  60
Leu Arg Cys Val Tyr Ser Glu Arg Arg Pro Lys Arg Lys Leu Arg Gln
 65                  70                  75                  80
Ser Arg Ala Ala Asp Leu Val Ser Ala Asp Pro Asp Pro Cys Leu His
                 85                  90                  95
Met Ser Ser Pro Pro Val Pro Ser Gln Ser Leu Pro Leu Asp Val Ser
                100                 105                 110
Glu Ser His Ser Ser Asn Thr Ser Arg Gln Phe Leu Asp Pro Pro Asp
                115                 120                 125
Ser Tyr Asp Trp Ser Trp Thr Ser Ile Gly Thr Asp Glu Ala Ile Asp
                130                 135                 140
Thr Asp Cys Trp Gly Leu Ser Gln Cys Asp Gly Phe Ser Cys Gln
145                 150                 155                 160
Leu Glu Pro Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
                180                 185                 190
Ser Ala Gln Arg Glu Leu Phe Asp Asp Leu Ser Ala Val Ser Gln Glu
                195                 200                 205
Leu Glu Glu Ile Leu Leu Ala Val Thr Val Glu Trp Pro Lys Gln Glu
                210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Ala
                245                 250                 255
Leu Asp Glu Cys Leu Arg Thr Lys Asn Leu Phe Thr Ala Val His Cys
                260                 265                 270
Tyr Ile Leu Asn Val Arg Ile Leu Thr Ala Ile Ser Glu Leu Leu Leu
                275                 280                 285
Ser Gln Ile Arg Arg Thr Gln Asn Ser His Met Ser Pro Leu Glu Gly
                290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
                340                 345                 350
Ala Cys Thr Thr Leu His Val Gly Val Gln Leu Leu Arg Glu Asn Glu
                355                 360                 365
Ile Thr Leu Gly Val His Ser Ala Gln Gly Ile Ala Ala Ser Ile Ser
                370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
                420                 425                 430
Gly Ser Arg Gly Arg Thr Ile Ala Ala Leu Arg Arg Cys Tyr Glu Asp
                435                 440                 445
Ile Phe Ser Leu Ala Arg Lys His Lys His Gly Met Leu Arg Asp Leu
                450                 455                 460
```

Asn Ser Ile Pro Pro
465

<210> SEQ ID NO 48
<211> LENGTH: 469
<212> TYPE: PRT
<213> ORGANISM: Artificial Sequence
<220> FEATURE:
<223> OTHER INFORMATION: synthetically generated variant

<400> SEQUENCE: 48

```
Met Ala Ala Asp Gln Gly Ile Phe Thr Asn Ser Val Thr Leu Ser Pro
 1               5                  10                  15

Val Glu Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Arg Pro Lys Arg Lys Leu Arg Gln
 65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Ala
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350
```

```
Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
        370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
                435                 440                 445

Ile Phe Ser Leu Ala Arg Lys His Lys His Gly Met Leu Arg Asp Leu
        450                 455                 460

Asn Ser Ile Pro Pro
465

<210> SEQ ID NO 49
<211> LENGTH: 469
<212> TYPE: PRT
<213> ORGANISM: Artificial Sequence
<220> FEATURE:
<223> OTHER INFORMATION: synthetically generated variant

<400> SEQUENCE: 49

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Arg Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
                100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
        130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240
```

```
Leu Thr Val Leu Arg Gln Gln Ala Gln Ala Asp Cys His Gln Gly Ala
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Thr Ala Ile Ser Glu Leu Leu Leu
        275                 280                 285
Ser Gln Ile Arg Arg Thr Gln Asn Ser His Met Ser Pro Leu Glu Gly
    290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
        355                 360                 365
Ile Thr Leu Gly Val His Ser Ala Gln Gly Ile Ala Ala Ser Ile Ser
    370                 375                 380
Met Ser Gly Glu Pro Gly Glu Asp Ile Ala Arg Thr Gly Ala Thr Asn
385                 390                 395                 400
Ser Ala Arg Cys Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
        435                 440                 445
Ile Phe Ser Leu Ala Arg Lys His Lys His Gly Met Leu Arg Asp Leu
    450                 455                 460
Asn Ser Ile Pro Pro
465

<210> SEQ ID NO 50
<211> LENGTH: 469
<212> TYPE: PRT
<213> ORGANISM: Artificial Sequence
<220> FEATURE:
<223> OTHER INFORMATION: synthetically generated variant

<400> SEQUENCE: 50

Met Ala Ala Asp Gln Gly Ile Phe Thr Asn Ser Val Thr Leu Ser Pro
1               5                   10                  15
Val Glu Gly Ser Arg Thr Gly Gly Thr Leu Pro Arg Arg Ala Phe Arg
            20                  25                  30
Arg Ser Cys Asp Arg Cys His Ala Gln Lys Ile Lys Cys Thr Gly Asn
        35                  40                  45
Lys Glu Val Thr Gly Arg Ala Pro Cys Gln Arg Cys Gln Gln Ala Gly
    50                  55                  60
Leu Arg Cys Val Tyr Ser Glu Arg Arg Pro Lys Arg Lys Leu Arg Gln
65                  70                  75                  80
Ser Arg Ala Ala Asp Leu Val Ser Ala Asp Pro Asp Pro Cys Leu His
            85                  90                  95
Met Ser Ser Pro Pro Val Pro Ser Gln Ser Leu Pro Leu Asp Val Ser
        100                 105                 110
Glu Ser His Ser Ser Asn Thr Ser Arg Gln Phe Leu Asp Pro Pro Asp
    115                 120                 125
```

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Ala
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Ser Ile Pro Pro
465

<210> SEQ ID NO 51
<211> LENGTH: 469
<212> TYPE: PRT
<213> ORGANISM: Artificial Sequence
<220> FEATURE:
<223> OTHER INFORMATION: synthetically generated variant

<400> SEQUENCE: 51

Met Ala Ala Asp Gln Gly Ile Phe Met Asn Ser Val Thr Leu Ser Ala
1               5                   10                  15

-continued

```
Val Glu Gly Ser Arg Thr Ser Gly Thr Leu Pro Arg Arg Ala Phe Arg
         20                  25                  30

Arg Ser Cys Asp Arg Cys His Ala Lys Lys Ile Lys Cys Thr Gly Asn
         35                  40                  45

Lys Glu Val Thr Gly Arg Ala Pro Cys Gln Arg Cys Gln Gln Ala Gly
         50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
                100                 105                 110

Glu Ser His Ser Ser Asn Thr Ser Arg Gln Phe Leu Asp Pro Pro Asp
             115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Glu Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430
```

```
Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
450                 455                 460

Asn Asn Ile Pro Pro
465

<210> SEQ ID NO 52
<211> LENGTH: 469
<212> TYPE: PRT
<213> ORGANISM: Artificial Sequence
<220> FEATURE:
<223> OTHER INFORMATION: synthetically generated variant

<400> SEQUENCE: 52

Met Ala Ala Asp Gln Gly Ile Phe Thr Asn Ser Val Thr Leu Ser Pro
1               5                   10                  15

Val Glu Gly Ser His Thr Gly Gly Thr Leu Pro Arg Arg Ala Phe Arg
            20                  25                  30

Arg Ala Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg His
65                  70                  75                  80

Ser Arg Ala Ser Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Asp Gly
    290                 295                 300

Ser Arg Ser Gln Ser Pro Ser Arg Asp Asp Thr Ser Ser Ser Ser Gly
305                 310                 315                 320
```

```
His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
                340                 345                 350

Ala Cys Thr Thr Leu His Val Gly Val Gln Leu Leu Arg Glu Asn Glu
                355                 360                 365

Ile Thr Leu Gly Val Asp Ser Ala Gln Gly Ile Ala Ala Ser Ile Ser
            370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Thr Val Leu Arg Arg Ser Tyr Glu Asp
                435                 440                 445

Ile Phe Ser Leu Ala Arg Lys His Lys His Gly Met Leu Arg Asp Leu
            450                 455                 460

Asn Asn Ile Pro Ser
465

<210> SEQ ID NO 53
<211> LENGTH: 469
<212> TYPE: PRT
<213> ORGANISM: Artificial Sequence
<220> FEATURE:
<223> OTHER INFORMATION: synthetically generated variant

<400> SEQUENCE: 53

Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Leu Arg
                20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
                100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
        130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
                180                 185                 190

Ser Ala Gln Arg Glu Leu Phe Asp Asp Leu Ser Ala Val Ser Gln Glu
            195                 200                 205
```

```
Leu Glu Glu Ile Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu
            275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
    355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Ile Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 54
<211> LENGTH: 469
<212> TYPE: PRT
<213> ORGANISM: Artificial Sequence
<220> FEATURE:
<223> OTHER INFORMATION: synthetically generated variant

<400> SEQUENCE: 54

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Leu Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95
```

```
Ile Ser Ser Pro Pro Val Pro Ser Gln Ser Leu Pro Leu Asp Val Ser
            100                 105                 110
Asp Ser His Ser Ser Asn Thr Ser Arg Gln Phe Leu Asp Pro Pro Asp
            115                 120                 125
Ser Tyr Asp Trp Ser Trp Thr Ser Ile Gly Thr Asp Glu Ala Ile Asp
    130                 135                 140
Thr Asn Cys Trp Gly Leu Ser Gln Cys Asp Gly Gly Phe Ser Cys Gln
145                 150                 155                 160
Leu Glu Ser Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
                180                 185                 190
Ser Ala Gln Arg Glu Leu Phe Asp Asp Leu Ser Ala Val Ser Gln Glu
            195                 200                 205
Leu Glu Glu Ile Leu Leu Ala Val Thr Val Glu Trp Pro Lys Gln Glu
        210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Thr Ala Ile Ser Glu Leu Leu Leu
        275                 280                 285
Ser Gln Ile Arg Arg Thr Gln Asn Ser His Met Ser Pro Leu Glu Gly
        290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Ile Glu
            355                 360                 365
Ile Thr Leu Gly Val His Ser Ala Gln Gly Ile Ala Ala Ser Ile Ser
        370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
            405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
            435                 440                 445
Ile Phe Ser Leu Ala Arg Lys His Lys Tyr Gly Met Leu Arg Asp Leu
        450                 455                 460
Asn Asn Ile Pro Pro
465

<210> SEQ ID NO 55
<211> LENGTH: 470
<212> TYPE: PRT
<213> ORGANISM: Artificial Sequence
<220> FEATURE:
<223> OTHER INFORMATION: synthetically generated variant
```

-continued

<400> SEQUENCE: 55

```
Met Ala Ala Asp Gln Gly Ile Phe Thr Asn Ser Val Thr Leu Ser Pro
 1               5                  10                  15
Val Glu Gly Ser Arg Thr Gly Gly Thr Leu Pro Arg Arg Ala Phe Arg
            20                  25                  30
Arg Ser Cys Asp Arg Cys His Ala Gln Lys Val Lys Cys Thr Gly Asn
        35                  40                  45
Lys Glu Val Thr Gly Arg Ala Pro Cys Gln Arg Cys Gln Gln Ala Gly
    50                  55                  60
Leu Arg Cys Val Tyr Ser Glu Arg Cys Pro Lys Arg Lys Leu Arg Gln
65                  70                  75                  80
Ser Arg Ala Ala Asp Leu Val Ser Ala Asp Pro Asp Pro Cys Leu His
                85                  90                  95
Met Ser Ser Pro Pro Val Pro Ser Gln Ser Leu Pro Leu Asp Val Ser
            100                 105                 110
Glu Ser His Ser Ser Asn Thr Ser Arg Gln Phe Leu Asp Pro Pro Asp
        115                 120                 125
Ser Tyr Asp Trp Ser Trp Thr Ser Ile Gly Thr Asp Glu Ala Ile Asp
    130                 135                 140
Thr Asp Cys Trp Gly Leu Ser Gln Cys Asp Gly Gly Phe Ser Cys Gln
145                 150                 155                 160
Leu Glu Pro Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
            180                 185                 190
Ser Ala Gln Arg Glu Leu Phe Asp Asp Leu Ser Ala Val Ser Gln Glu
        195                 200                 205
Leu Glu Glu Ile Leu Leu Ala Val Thr Val Glu Trp Pro Lys Gln Glu
    210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Thr Ala Ile Ser Glu Leu Leu Leu
        275                 280                 285
Ser Gln Ile Arg Arg Thr Leu Asn Ser His Met Ser Pro Leu Glu Gly
    290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
        355                 360                 365
Ile Thr Leu Gly Val His Ser Ala Gln Gly Ile Ala Ala Ser Ile Ser
    370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
```

```
                        405                 410                 415
Phe Met Phe Leu Ser Asp Glu Gly Ala Phe Gln Glu Ala Lys Ser Ala
                420                 425                 430
Gly Ser Arg Gly Arg Thr Ile Ala Ala Leu Arg Arg Cys Tyr Glu Asp
            435                 440                 445
Ile Phe Ser Leu Ala Arg Lys His Lys His Gly Met Leu Arg Asp Leu
        450                 455                 460
Asn Asn Ile Pro Pro Cys
465                 470

<210> SEQ ID NO 56
<211> LENGTH: 469
<212> TYPE: PRT
<213> ORGANISM: Artificial Sequence
<220> FEATURE:
<223> OTHER INFORMATION: synthetically generated variant

<400> SEQUENCE: 56

Met Ala Ala Asp Gln Gly Ile Phe Thr Asn Ser Val Thr Leu Ser Pro
1               5                   10                  15
Val Glu Gly Ser Arg Thr Gly Gly Thr Leu Pro Arg Arg Ala Leu Arg
            20                  25                  30
Arg Ser Cys Asp Arg Cys His Ala Gln Lys Ile Lys Cys Thr Gly Asn
        35                  40                  45
Lys Glu Val Thr Gly Arg Ala Pro Cys Gln Arg Cys Gln Gln Ala Gly
    50                  55                  60
Leu Arg Cys Val Tyr Ser Glu Arg Cys Pro Lys Arg Lys Leu Arg Gln
65                  70                  75                  80
Ser Arg Ala Ala Asp Leu Val Ser Ala Asp Pro Asp Pro Cys Leu His
                85                  90                  95
Met Ser Ser Pro Ser Val Pro Ser Gln Ser Leu Pro Leu Asp Val Ser
            100                 105                 110
Glu Ser His Ser Ser Asn Thr Ser Arg Gln Phe Leu Asp Pro Pro Asp
        115                 120                 125
Ser Tyr Asp Trp Ser Trp Thr Ser Ile Gly Thr Asp Glu Ala Ile Asp
    130                 135                 140
Thr Asp Cys Trp Gly Leu Ser Gln Arg Asp Gly Gly Phe Ser Ser Gln
145                 150                 155                 160
Leu Lys Pro Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
            180                 185                 190
Ser Ala Gln Arg Glu Leu Phe Asp Asp Leu Ser Ala Val Ser Gln Glu
        195                 200                 205
Leu Glu Glu Ile Leu Leu Ala Val Thr Val Glu Trp Pro Lys Gln Glu
    210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Thr Ala Ile Ser Glu Leu Leu Leu
        275                 280                 285
Ser Gln Ile Arg Leu Thr Gln Asn Ser His Met Ser Pro Leu Glu Gly
```

-continued

```
              290                 295                 300
Ser Arg Ser Gln Ser Pro Asn Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
                340                 345                 350

Ala Cys Thr Thr Leu His Val Gly Val Gln Leu Leu Arg Glu Asn Glu
                355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
                435                 440                 445

Ile Phe Ser Leu Ala Arg Lys His Lys His Gly Met Leu Arg Asp Leu
                450                 455                 460

Asn Asn Ile Pro Pro
465
```

<210> SEQ ID NO 57
<211> LENGTH: 469
<212> TYPE: PRT
<213> ORGANISM: Artificial Sequence
<220> FEATURE:
<223> OTHER INFORMATION: synthetically generated variant

<400> SEQUENCE: 57

```
Met Ala Ala Asp Gln Gly Ile Phe Thr Asn Ser Val Thr Ile Ser Pro
1               5                   10                  15

Val Val Gly Ser Arg Thr Gly Gly Thr Leu Pro Arg Arg Ala Phe Arg
                20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
                100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Cys Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
```

```
                180                 185                 190
Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Gly Leu Phe Ser Tyr Val Asp Pro Leu Thr His Ala Leu Phe Ser
            340                 345                 350

Ala Cys Thr Thr Leu His Val Gly Leu Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Ser Gly Glu Asp Ile Ala Arg Thr Gly Ala Thr Ser
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 58
<211> LENGTH: 469
<212> TYPE: PRT
<213> ORGANISM: Artificial Sequence
<220> FEATURE:
<223> OTHER INFORMATION: synthetically generated variant

<400> SEQUENCE: 58

Met Ala Ala Asp Gln Gly Ile Phe Thr Asn Ser Val Thr Leu Ser Pro
  1               5                  10                  15

Val Glu Gly Ser Arg Thr Gly Thr Leu Pro Arg Arg Ala Phe Arg
             20                  25                  30

Arg Ser Cys Asp Arg Cys His Ala Arg Lys Ile Lys Cys Thr Gly Asn
            35                  40                  45

Lys Glu Val Thr Gly Arg Ala Pro Cys Gln Arg Cys Gln Gln Ala Gly
        50                  55                  60

Leu Arg Cys Val Tyr Ser Glu Arg Cys Pro Lys Arg Lys Leu Arg Gln
```

-continued

```
                65                  70                  75                  80
Ser Arg Ala Ala Asp Leu Val Ser Ala Asp Pro Asp Pro Cys Leu His
                    85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Tyr Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Thr Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 59
```

-continued

<211> LENGTH: 469
<212> TYPE: PRT
<213> ORGANISM: Artificial Sequence
<220> FEATURE:
<223> OTHER INFORMATION: synthetically generated variant

<400> SEQUENCE: 59

```
Met Ala Ala Asp Gln Gly Ile Phe Thr Asn Ser Val Thr Leu Ser Pro
 1               5                  10                  15

Val Glu Gly Ser Arg Thr Gly Gly Thr Leu Pro Arg Arg Ala Leu Arg
            20                  25                  30

Arg Ser Cys Asp Arg Cys His Ala Gln Lys Ile Lys Cys Thr Gly Asn
        35                  40                  45

Lys Glu Val Ile Gly Arg Ala Pro Cys Gln Arg Cys Gln Gln Ala Gly
 50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                85                  90                  95

Met Ser Ser Pro Gln Val Pro Ser Gln Ser Leu Ser Leu Asp Ile Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
370                 375                 380
```

-continued

```
Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
            405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
        450                 455                 460

Asn Asn Ile Pro Pro
465
```

<210> SEQ ID NO 60
<211> LENGTH: 469
<212> TYPE: PRT
<213> ORGANISM: Artificial Sequence
<220> FEATURE:
<223> OTHER INFORMATION: synthetically generated variant

<400> SEQUENCE: 60

```
Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asn Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Phe Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Ile Phe Phe Asn Ala Ser Arg Arg Leu
225                 230                 235                 240

Leu Thr Val Leu Arg Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270
```

-continued

Tyr Ile Leu Asn Val Arg Ile Leu Thr Ala Ile Ser Glu Leu Leu Leu
            275                 280                 285

Ser Gln Ile Arg Arg Thr Gln Asn Ser His Met Ser Pro Leu Glu Gly
        290                 295                 300

Ser Arg Ser Gln Ser Pro Ser Arg Asp Asp Ile Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Tyr Ile Ser
        370                 375                 380

Lys Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
        450                 455                 460

Asn Asn Ile Pro Pro
465

<210> SEQ ID NO 61
<211> LENGTH: 469
<212> TYPE: PRT
<213> ORGANISM: Artificial Sequence
<220> FEATURE:
<223> OTHER INFORMATION: synthetically generated variant

<400> SEQUENCE: 61

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Ile Gly Asn
        35                  40                  45

Lys Glu Val Thr Gly Arg Ala Pro Cys Gln Arg Cys Gln Arg Ala Gly
    50                  55                  60

Leu Arg Cys Val Tyr Ser Glu Arg Cys Pro Lys Arg Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

```
Leu Glu Pro Thr Leu Pro Asp Leu Pro Ser Pro Phe Glu Ser Thr Val
                165                 170                 175

Glu Lys Ala Pro Leu Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
            275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Cys Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Tyr Glu
            355                 360                 365

Ile Thr Leu Gly Ile His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 62
<211> LENGTH: 469
<212> TYPE: PRT
<213> ORGANISM: Artificial Sequence
<220> FEATURE:
<223> OTHER INFORMATION: synthetically generated variant

<400> SEQUENCE: 62

Met Ala Ala Asp Gln Gly Ile Phe Thr Asn Ser Val Thr Leu Ser Pro
  1               5                  10                  15

Val Glu Gly Ser Arg Thr Gly Thr Leu Pro Arg Arg Ala Phe Arg
             20                  25                  30

Arg Ser Cys Asp Arg Cys His Ala Arg Lys Ile Lys Cys Thr Gly Asn
             35                  40                  45
```

-continued

```
Lys Glu Val Thr Gly Arg Ala Pro Cys Gln Arg Cys Gln Gln Ala Gly
 50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Ile Gln Asn Ser His Met Ser Pro Leu Glu Gly
    290                 295                 300

Ser Arg Ser Gln Ser Leu Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Asp Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Leu Gly Glu Asp Ile Val Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Ser Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460
```

Asn Asn Ile Pro Pro
465

<210> SEQ ID NO 63
<211> LENGTH: 469
<212> TYPE: PRT
<213> ORGANISM: Artificial Sequence
<220> FEATURE:
<223> OTHER INFORMATION: synthetically generated variant

<400> SEQUENCE: 63

Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Asn Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Ile Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Ile Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Ile Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Ala Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
        370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
        450                 455                 460

Asn Asn Ile Pro Pro
465

<210> SEQ ID NO 64
<211> LENGTH: 469
<212> TYPE: PRT
<213> ORGANISM: Artificial Sequence
<220> FEATURE:
<223> OTHER INFORMATION: synthetically generated variant

<400> SEQUENCE: 64

Met Ala Ala Glu Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Arg Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Ile Ser Ala Asp Pro Asp Pro Cys Leu His
                85                  90                  95

Met Ser Ser Pro Pro Val Pro Ser Gln Ser Leu Pro Leu Glu Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Lys Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Thr Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

-continued

```
Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asp Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Arg His Ala Leu Phe Ser
            340                 345                 350

Ala Cys Thr Thr Leu His Val Gly Val Gln Leu Leu Arg Glu Ile Glu
        355                 360                 365

Ile Thr Leu Gly Val His Ser Ala Arg Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Thr Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 65
<211> LENGTH: 469
<212> TYPE: PRT
<213> ORGANISM: Artificial Sequence
<220> FEATURE:
<223> OTHER INFORMATION: synthetically generated variant

<400> SEQUENCE: 65

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125
```

Ser Tyr Asn Trp Leu Trp Thr Ser Ile Gly Thr Asp Glu Ala Ile Asp
            130                 135                 140

Thr Asp Cys Trp Gly Leu Ser Gln Cys Asp Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Val Ser Ser Asp Ile Ala Arg Ala Ala
                180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
    275                 280                 285

Ser Gln Ile Arg Arg Thr Gln Asn Ser His Met Ser Pro Leu Glu Gly
290                 295                 300

Ser Arg Ser Gln Ser Pro Ser Gly Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
                355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Gly Lys Ser Ala
            420                 425                 430

Gly Ser Arg Gly Arg Thr Ile Ala Ala Leu Arg Arg Cys Tyr Glu Asp
    435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 66
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 66
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120

-continued

```
caaaagatca aatgtactgg aaataaggag gttactggcc gtgctccctg tcagcgttgc        180
cagcaggctg gacttcgatg cgtctacagt gagcgatgcc ccaagcgcaa gctacgccaa        240
tccagggcag cggatctcgt ctctgctgac ccagatccct gcttgcacat gtcctcgcct        300
ccagtgccct cacagagctt gccgctagac gtatccgagt cgcattcctc aaatacctcc        360
cggcagtttc ttgatccacc ggacagctac gactggtcgt ggacctcgat tggcactgac        420
gaggctattg acactgactg ctgggggctg tcccaatgtg atggaggctt cagctgtcag        480
ttagagccaa cgctgccgga tctaccttcg cccttcgagt ctacggttga aaaagctccg        540
ttgccaccgg tatcgagcga cattgctcgt gcggccagtg cgcaacgaga gcttttcgat        600
gacctgtcgg cggtgtcgca ggaactggaa gagatccttc tggccgtgac ggtagaatgg        660
ccgaagcagg aaatctggac ccatcccatc ggaatgtttt tcaatgcgtc acgacggctt        720
cttactgtcc tgcgccaaca agcgcaggcc gactgccgtc aaggcacact agacgaatgt        780
ttacggacca agaacctctt tacggcagta cactgttaca tattgaatgt gcggattttg        840
accgccatat cggagttgct cctgtcgcaa attaggcgga cccagaacag ccatatgagc        900
ccactggaag ggagtcgatc ccagtcgccg agcagagacg acaccagcag cagcagcggc        960
cacagcagtg ttgacaccat accettctttt agcgagaacc tcctattgg tgagctgttc       1020 ccctatgttg accccctgac acacgcccta ttctcggctt gcactacgtt acatgttggg       1080
gtacaattgc tgcgtgagaa tgagattact ctgggagtac actccgccca gggcattgca       1140
gcttccatca gcatgagcgg ggaaccaggc gaggatatag ccaggacagg ggcgaccaat       1200
tccgcaagat gcgaggagca gccgaccact ccagcggctc gggttttgtt catgttcttg       1260
agtgatgaag gggcttttcca ggaggcaaag tctgctggtt cccgaggtcg aaccatcgca       1320
gcactgcgac gatgctatga ggatatcttt tccctcgccc gcaaacacaa acatggcatg       1380
ctcagagacc tcaacaatat tcctccatga                                         1410
```

<210> SEQ ID NO 67
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 67

```
atggctgcag atcaaggtat attcacgaac tcggtcactc tctcgccagt ggagggttca         60
cgcaccggtg gaacattacc ccgccgtgca ttccgacgct cttgtgatcg gtgtcatgca        120
caaaagatca aatgtactgg aaataaggag gttactggcc gtgctccctg tcagcgttgc        180
cagcaggctg gacttcgatg cgtctacagt gagcgatgcc ccaagcgcaa gctacgccaa        240
tccagggcag cggatctcgt ctctgctgac ccagatccct gcttgcacat gtcctcgcct        300
ccagtgccct cacagagctt gccgctagac gtatccgagt cgcattcctc aaatacctcc        360
tggcaatttc ttgatccacc ggacagctac gactggttgt ggacctcgat tggcactgac        420
gaggctattg acactgactg ctgggggctg tcccaatgtg atggaggctt cagctgtcag        480
ttagagccaa cgctgccgga tctaccttcg cccttcgagt ctacggttga aaaagctccg        540
ttgccaccgg tatcgagcga cattgctcgt gcggccagtg cgcaacgaga gcttttcgat        600
gacctgtcgg cggtgtcgca ggaactggaa gagatccttc tggccgtgac ggtagagtgg        660
ccgaagcagg aaatctggac ccatcccatc ggaatgtttt tcaatgcgtc acgacggctt        720
```

| | |
|---|---|
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacggcagtg ttgacaccat acccttcttt agcgagaacc tccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcttttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 68
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 68

| | |
|---|---|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc ccaagcgcaa gctacgccaa | 240 |
| tccaggtag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggatctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat acccttcttt agcgagaacc tccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcttttcca ggaggcaaag tctgctggtt cccgaggtcg aaccatcgca | 1320 |
| gcactgcgac gatgctatga ggatatcttt tccctcgccc gcaaacacaa acatggcatg | 1380 | ctcagagacc tcaacaatat tcctccatga        1410

<210> SEQ ID NO 69
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 69

| | | |
|---|---|---|
| atggctgcag atcaaggtat attcacgaac tcggtcactc tctcgccagt ggagggttca | 60 |
| cgcaccggtg aacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc caagcgcaa gctacgccaa | 240 |
| tccagggcag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttgg aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatcctc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat accttctttt agcgagaacc tcctattgg tgagctgttc | 1020 |
| tcctatgttg acccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcttttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 70
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 70

| | | |
|---|---|---|
| atggctgcag atcaaggtat attcacgaac tcggtcactc tctcgccagt ggagggttca | 60 |
| cgcaccggtg aacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc caagcgcaa gctacgccaa | 240 |

```
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctggggctg tcccaatgtg atggaggctt cagctgtcag     480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat accctttcttt agcgagaacc tccctattgg tgagctgttc   1020
tcctatgttg accccctgac acacgcccta ttctcggctt gcactacgtt acatgttggg    1080
gtacaattgc tgcgtgagaa tgagattact ctgggagtac actccgccca gggcattgca    1140
gcttccatca gcatgagcgg ggaaccaggc gaggatatag ccaggacagg ggcgaccaat    1200
tccgcaagat gcgaggagca gccgactact ccagcggctc gggttttgtt catgttcttg    1260
agtgatgaag gggctttcca ggaggcaaag tctgctggtt cccgaggtcg aaccatcgca    1320
gcactgcgac gatgctatga ggatatcttt tccctcgccc gcaaacacaa acatggcatg    1380
ctcagagacc tcaacaatat tcctccatga                                    1410

<210> SEQ ID NO 71
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 71
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctggggctg tcccaatatg atggaggctt cagctgtcag     480
ttagagccaa cgctgccgga tctaccttcg cccttcgagt ctacggttga aaaagctccg    540
ttgccaccgg tatcgagcga cattgctcgt gcggccagtg cgcaacgaaa gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
gccgccatat cggagttgct cctgtcgcaa attaggcgga cccagaacag ccatatgagc    900
```

-continued

```
ccactggaag ggagtcgatc ccagtcgccg agcagagacg acaccagcag cagcagcggc      960
cacagcagtg ttgacaccat accttctttt agcgagaacc tccctattgg tgagctgttc     1020
tcctatgttg accccctgac acacgcccta ttctcggctt gcactacgtt acatgttggg     1080
gtacaattgc tgcgtgagaa tgagattact ctgggagtac actccgccca gggcattgca     1140
gcttccatca gcatgagcgg ggaaccaggc gaggatatag ccaggacagg ggcgaccaat     1200
tccgcaagat gcgaggagca gccgaccact ccagcggctc gggttttgtt catgttcttg     1260
agtgatgaag gggcttttcca ggaggcaaag tctgctggtt cccgaggtcg aaccatcgca    1320
gcactgcgac gatgctatga ggatatcttt ccctcgccc gcaaacacaa acatggcatg      1380
ctcagagacc tcaacaatat tcctccatga                                      1410
```

<210> SEQ ID NO 72
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 72

```
atggctgcag atcaaggtat attcacgaac tcggtcactc tctcgccagt ggagggttca       60
cgcaccggtg gaacattacc ccgccgtgca ttccgacgct cttgtgatcg gtgtcatgca      120
caaaagatca aatgtactgg aaataaggag gttactggcc gtgctccctg tcagcgttgc      180
cagcaggctg gacttcgatg cgtctacagt gagcgacgcc ccaagcgcaa gctacgccaa      240
tccagggcag cggatctcgt ctctgctgac ccagatccct gcttgcacat gtcctcgcct      300
ccagtgccct cacagagctt gccgctagac gtatccgagt cgcattcctc aaatacctcc      360
cggcaatttc ttgatccacc ggacagctac gactggtcgt ggacctcgat tggcactgac      420
gaggctattg acactgactg ctgggggctg tcccaatgtg atggaggctt cagctgtcag      480
ttagagccaa cgctgccgga tctaccttcg cccttcgagt ctacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcgtc acgacggctt      720
cttactgtcc tgcgccaaca agcgcaggcc gactgccatc aaggcgcact agacgaatgt      780
ttacggacca agaacctctt tacgcagtac cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acaccagcag cagcagcggc      960
cacagcagtg ttgacaccat accttctttt agcgagaacc tccctattgg tgagctgttc     1020
tcctatgttg accccctgac acacgcccta ttctcggctt gcactacgtt acatgttggg     1080
gtacaattgc tgcgtgagaa tgagattact ctgggagtac actccgccca gggcattgca     1140
gcttccatca gcatgagcgg ggaaccaggc gaggatatag ccaggacagg ggcgaccaat     1200
tccgcaagat gcgaggagca gccgaccact ccagcggctc gggttttgtt catgttcttg     1260
agtgatgaag gggcttttcca ggaggcaaag tctgctggtt cccgaggtcg aaccatcgca    1320
gcactgcgac gatgctatga ggatatcttt ccctcgccc gcaaacacaa acatggcatg      1380
ctcagagacc tcaacagtat tcctccatga                                      1410
```

<210> SEQ ID NO 73

<211> LENGTH: 1410
<212> TYPE: DNA
<213> ORGANISM: Artificial Sequence
<220> FEATURE:
<223> OTHER INFORMATION: synthetically generated variant

<400> SEQUENCE: 73

| | |
|---|---|
| atggctgcag atcaaggtat attcacgaac tcggtcactc tctcgccagt ggagggttca | 60 |
| cgcaccggtg aacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc ccaagcgcaa gctacgccaa | 240 |
| tccagggcag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gtggctattg acactgactg ctggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca gcgcaggcc gactgccatc aaggcacact agacgaatgt | 780 |
| ttacggacca agaacctctt tacgcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat accttctt agcgagaacc tccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggctttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 74
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 74

| | |
|---|---|
| atggctgcag atcaaggtat attcacgaac tcggtcactc tctcgccagt ggagggttca | 60 |
| cgcaccggtg aacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc ccaagcgcaa gctacgccaa | 240 |
| tccagggcag cggatctcgt ttctgctgac ccagatccct gcttgcacat gtcctcgcct | 300 |
| ccagtgccct cacagagctt gccactagac gtatccgagt cgcattcctc aaatacctcc | 360 |
| cggcaatttc ttgatccacc ggacagctac gactggtcgt ggacctcgat tggcactgac | 420 |

-continued

```
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaacgt gcggattttg    840
accgccatat cggagttgct cctgtcgcaa attaggcgga cccagaacag ccatatgagc    900
ccactgaaag gggtcgatc ccagtcgccg agcagagacg acaccagcag cagcagcggc    960
cacagcagtg ttgacaccat accttctttt agcgagaacc tccctattgg tgagctgttc    1020
tcctatgttg accccctgac acgcccta ttctcggctt gcactacgtt acatgttggg    1080
gtacaattgc tgcgtgagaa tgagattact ctgggagtac actccgccca gggcattgca    1140
gcttccatca gcatgagcgg ggaaccagge gaggatatag ccaggacagg ggcgaccaat    1200
tccgcaagat gcgaggagca gccgaccact ccagcggctc gggttttgtt catgttcttg    1260
agtgatgaag gggcttttcca ggaggcaaag tctgctggtt cccgaggtcg aaccatcgca    1320
gcactgcgac gatgctatga ggatatcttt tccctcgccc gcaaacacaa acatggcatg    1380
ctcagagacc tcaacaatat tcctccatga                                    1410
```

<210> SEQ ID NO 75
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 75

```
atggctgcag atcaaggtat attcacgaac tcggtcactc tctcgccagt ggagggttca    60
cgcaccggtg gaacattacc ccgccgtgca ttccgacgct cttgtgatcg gtgtcatgca    120
aaaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactgaaag gggtcgatc ccagtcgccg agcagagacg acaccagcag cagcagcggc    960
cacagcagtg ttgacaccat accttctttt agcgagaacc tccctattgg tgagctgttc    1020
```

```
tcctatgttg accccctgac acacgcccta ttctcggctt gcactacgct acatgttggg    1080
gtacaattgc tgcgtgagaa tgagattact ctgggagtac actccgccca gggcattgca    1140
gcttccatca gcatgagcgg ggaaccaggc gaggatatag ccaggacagg ggcgaccaat    1200
tccgcaagat gcgaggagca gccgaccact ccagcggctc gggttttgtt catgttcttg    1260
agtgatgaag gggctttcca ggaggcaaag tctgctggtt cccgaggtcg aaccatcgca    1320
gcactgcgac gatgctatga ggatatcttt ccctcgccc gcaaacacaa acatggcatg    1380
ctcagagacc tcaacaatat tcctccatga                                     1410
```

<210> SEQ ID NO 76
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 76

```
atggctgcag atcaaggtat attcatgaac tcggtcactc tctctgcagt ggagggttca      60
cgcaccagtg gaacattacc ccgccgtgca ttccgacgct cttgtgatcg gtgtcatgca     120 aaaagatca aatgtactgg aaataaggag gttactggcc gtgctccctg tcagcgttgc      180
cagcaggctg gacttcgatg cgtctacagt gagcgatgcc ccaagcgcaa gctacgccaa     240
tccagggcag cggatctcgt ctctgctgac ccagatccct gcttgcacat gtcctcgcct     300
ccagtgccct cacagagctt gccgctagac gtatccgagt cgcattcctc aaataccccc     360
cggcaatttc ttgatccacc ggacagctac gactggtcgt ggacctcgat tggcactgac     420
gaggctattg acactgactg ctgggggctg tcccaatgtg atggaggctt cagctgtcag     480
ttagagccaa cgctgccgga tctaccttcg cccttcgagt ctacagttga aaaagctccg     540
ttgccaccgg tatcgagcga cattgctcgt gcggccagtg cgcaacgaga gcttttcgat     600
gacctgtcgg cggtgtcgca ggaactggaa gagatccttc tggccgtgac ggtagaatgg     660
ccgaagcagg aaatctggac ccatcccatc ggaatgtttt tcaatgcgtc acgacggctt     720
cttactgtcc tgcgccaaca agcgcaggcc gactgccatc aaggcacact agacgaatgt     780
ttacggacca agaacctctt tacggcagta cactgttaca tattgaatgt gcggattttg     840
accgccatat cggagttgct cctatcgcaa attaggcgga cccagaacag ccatatgagc     900
ccactggaag ggagtcgatc ccagtcgccg agcagagacg acactagcag cagcagcggc     960
cacagcagtg ttgacaccat accttctttt agcgagaacc tccctattgg tgagctgttc    1020
tcctatgttg accccctgac acacgcccta ttctcggctt gcactacgtt acatgttggg    1080
gtagaattgc tgcgtgagaa tgagattact ctgggagtac actccgccca gggcattgca    1140
gcttccatca gcatgagcgg ggaaccaggc gaggatatag ccaggacagg ggcgaccaat    1200
tccgcaagat gcgaggagca gccgaccact ccagcggctc gggttttgtt catgttcttg    1260
agtgatgaag gggctttcca ggaggcaaag tctgctggtt cccgaggtcg aaccatcgca    1320
gcactgcgac gatgctatga ggatatcttt ccctcgccc gcaaacacaa acatggcatg    1380
ctcagagacc tcaacaatat tcctccatga                                     1410
```

<210> SEQ ID NO 77
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 77

| | |
|---|---|
| atggctgcag atcaaggtat attcacgaac tcggtcactc tctcgccagt ggagggttca | 60 |
| cacaccggtg aacattacc cgccgtgca ttccgacgcg cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgatgcc ccaagcgcaa gctacgccat | 240 |
| tccagggcat cggatctcgt tctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggacg ggagtcgatc ccagtcgccg agcagagacg acaccagcag cagcagcggc | 960 |
| cacagcagtg ttgacaccat accttctttt agcgagaacc tccctattgg tgagctattc | 1020 |
| tcctatgttg accccctgac acacgcccta ttctcggctt gcactacgtt acatgttggg | 1080 |
| gtacaattgc tgcgtgagaa tgagattact ctgggagtag actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcttttcca ggaggcaaag tctgctggtt cccgaggtcg aaccatcaca | 1320 |
| gtactgcgac gaagctatga ggatatcttt ccctcgccc gcaaacacaa acatggcatg | 1380 |
| ctcagagacc tcaacaatat tccttcatga | 1410 |

<210> SEQ ID NO 78
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 78

| | |
|---|---|
| atggctgcag atcaaggtat attcacgaac tcggtcactc tctcgccagt ggagggttca | 60 |
| cgcaccggtg aacattacc cgccgtgca ctccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgatgcc ccaagcgcaa gctacgccaa | 240 |
| tccagggcag cggatctcgt tctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |

```
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcgtc acgacggctt      720
cttactgtcc tgcgccaaca agcgcaggcc gactgccatc aaggcacact agacgaatgt      780
ttacggacca agaacctctt tacggcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acaccagcag cagcagcggc      960
cacagcagtg ttgacaccat accccttcttt agcgagaacc tccctattgg tgagctgttc     1020
tcctatgttg accccctgac acacgcccta ttctcggctt gcactacgtt acatgttggg     1080
gtacaattgc tgcgtgagaa tgagattact ctgggagtac actccgccca ggcattgca      1140 gcttccatca gcatgagcgg ggaaccaggc gaggatatag ccaggacagg ggcgaccaat     1200
tccgcaagat gcgaggagca gccgatcact ccagcggctc gggttttgtt catgttcttg     1260
agtgatgaag gggctttcca ggaggcaaag tctgctggtt cccgaggtcg aaccatcgca     1320
gcactgcgac gatgctatga ggatatcttt tccctcgccc gcaaacacaa acatggcatg     1380
ctcagagacc tcaacaatat tcctccatga                                       1410
```

```
<210> SEQ ID NO 79
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 79
```

```
atggctgcag atcaaggtat attcacgaac tcggtcactc tctcgccagt ggagggttca       60
cgcaccggtg gaacattacc ccgccgtgca ctccgacgct cttgtgatcg gtgtcatgca      120
caaaagatca aatgtactgg aaataaggag gttactggcc gtgctccctg tcagcgttgc      180
cagcaggctg gacttcgatg cgtctacagt gagcgatgcc ccaagcgcaa gctacgccaa      240
tccagggcag cggatctcgt ctctgctgac ccagatccct gcttgcacat atcctcgcct      300
ccagtgccct cacagagctt accgctagag gtatccgatt cgcattcctc aaatacctcc      360
cggcaatttc ttgatccacc ggacagctac gactggtcgt ggacctcgat tggcactgac      420
gaggctattg acactaactg ctgggggctg tcccaatgtg atggaggctt cagctgtcag      480
ttagagtcaa cgctgccgga tctaccttcg cccttcgagt ctacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
cctaagcagg aaatctggac ccatcccatc ggaatgtttt tcaatgcgtc acgacggctt      720
cttactgtcc tgcgccaaca agcgcaggcc gactgccatc aaggcacact agacgaatgt      780
ttacggacca agaacctctt tacggcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acaccagcag cagcagcggc      960
cacagcagtg ttgacaccat accccttcttt agcgagaacc tccctattgg tgagctgttc     1020
tcctatgttg accccctgac acacgcccta ttctcggctt gcactacgtt acatgttggg     1080
gtacaattgc tgcgtgagat tgagattact ctgggagtac actccgccca ggcattgca      1140 gcttccatca gcatgagcgg ggaaccaggc gaggatatag ccaggacagg ggcaaccaat     1200
```

```
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa atatggcatg   1380
ctcagagacc tcaacaatat tcctccatga                                    1410

<210> SEQ ID NO 80
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 80
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120
caaaaggtca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt tctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgc cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga ccctgaacag ccatatgagc    900
ccactggaag ggagtcgatc ccagtcgccg agcagagacg acaccagcag cagcagcggc    960
cacagcagtg ttgacaccat acccttcttt agcgagaacc tccctattgg tgagctgttc   1020
tcctatgttg acccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                    1410

<210> SEQ ID NO 81
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 81
atggctgcag atcaaggtat attcacgaac tccgtcactc tctcgccagt ggagggttca     60
```

| | |
|---|---|
| cgcaccggtg gaacattacc ccgccgtgca ttacgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgatgcc ccaagcgcaa gttacgccaa | 240 |
| tccagggcag cggatctcgt ctctgctgac ccagatccct gcttgcacat gtcctcgcct | 300 |
| tcagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctggggctg tcccaacgtg atggaggctt cagctctcag | 480 |
| ttaaagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct actgtcgcaa attaggctga cccagaacag ccatatgagc | 900 |
| ccactggaag ggagtcgatc ccagtcgccg aacagagacg acaccagcag cagcagcggc | 960 |
| cacagcagtg ttgacaccat accttctttt agcgagaacc tccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcttttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 82
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 82

| | |
|---|---|
| atggctgcag atcaaggtat attcactaac tcggtcacta tctcgccagt ggtgggttca | 60 |
| cgcaccggtg gaacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgatgcc ccaagcgcaa gctacgccaa | 240 |
| tccagggcag cggatctcgt ctctgctgac ccagatccct gcttgcacat gtcctcgcct | 300 |
| ccagtgccct cacagagttt gccgctagac gtatccgagt cgcattcctc aaatacctcc | 360 |
| cggcaatttc ttgatccacc ggacagctac gactggtcgt ggacctcgat ttgcactgac | 420 |
| gaggctattg acactgactg ctggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |

```
cttactgtcc tgcgccaaca agcgcaggcc gactgccatc aaggcacact agacgaatgt      780
ttacggacca agaacctctt tacggcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acaccagcag cagcagcggc      960
cacagcagtt ttgacaccat acccttcttt agcgagaacc tccctattgg tgggctgttc     1020
tcctatgttg accccctgac acacgcccta ttctcggctt gcactacgtt acatgttggg     1080
ctacaattgc tgcgtgagaa tgagattact ctgggagtac actccgccca gggcattgca     1140
gcttccatca gcatgagcgg ggaatcaggc gaggatatag ccaggacagg ggcgaccagt     1200
tccgcaagat gcgaggagca gccgaccact ccagcggctc gggttttgtt catgttcttg     1260
agtgatgaag gggcttttcca ggaggcaaag tctgctggtt cccgaggtcg aaccatcgca     1320
gcactgcgac gatgctatga ggatatcttt tccctcgccc gcaaacacaa acatggcatg     1380
ctcagagacc tcaacaatat tcctccatga                                     1410

<210> SEQ ID NO 83
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 83
atggctgcag atcaaggtat attcacgaac tcggtcactc tctcgccagt ggagggttca       60
cgcaccggtg gaacattacc ccgccgtgca ttccgacgct cttgtgatcg gtgtcatgca      120
cgaaagatca aatgtactgg aaataaggag gttactggcc gtgctccctg tcagcgttgc      180
cagcaggctg gacttcgatg cgtctacagt gagcgatgcc ccaagcgcaa gctacgccaa      240
tccagggcag cggatctcgt ctctgctgac ccagatccct gcttgcacat gtcctcgcct      300
ccagtgccct cacagagctt gccgctagac gtatccgagt cgcattcctc aaatacctcc      360
cggcaatttc ttgatccacc ggacagctac gactggtcgt ggaccTcgat tggcactgac      420
gaggctattg acactgactg ctgggggctg tcccaatgtg atggaggctt cagctgtcag      480
ttagagccaa cgctgccgga tctaccttcg cccttcgagt atacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcgtc acgacggctt      720
cttactgtcc tgcgccaaca agcgcaggcc gactgccatc aaggcacact agacgaatgt      780
ttacggacca agaacctctt tacggcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acaccagcag cagcagcggc      960
cacagcagtt ttgacaccat acccttcttt agcgagaacc tccctattgg tgagctgttc     1020
tcctatgttg accccctgac acacgcccta ttctcggctt gcactacgtt acatgttggg     1080
gtacaattgc tgcgtgagaa tgagattact ctgggagtac actccgccca gggcattgca     1140
gcttccatca gcatgagcgg ggaaccaggc gaggatatag ccaggacagg ggcgaccaat     1200
tccacaagat gcgaggagca gccgaccact ccagcggctc gggttttgtt catgttcttg     1260
agtgatgaag gggcttttcca ggaggcaaag tctgctggtt cccgaggtcg aaccatcgca     1320
```

| | |
|---|---:|
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 84
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 84

| | |
|---|---:|
| atggctgcag atcaaggtat attcacgaac tcggtcactc tctcgccagt ggagggttca | 60 |
| cgcaccggtg aacattacc ccgccgtgca ttgcgacgct cttgtgatcg gtgtcatgca | 120 |
| caaaagatca aatgtactgg aaataaggag gttattggcc gtgctccctg tcagcgttgc | 180 |
| cagcaggctg gacttcgatg cgtatacagt gagcgatgcc ccaagcgcaa gctacgccaa | 240 |
| tccagggcag cggatctcgt ctctgctgac ccagatccct gcttgcacat gtcctcgcct | 300 |
| caagtgccct cacagagctt gtcgctagac atatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat acccttcttt agcgagaacc tccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcattcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 85
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 85

| | |
|---|---:|
| atggctgcag atcaaggtat attcacgaac tcggtcactc tctcaccagt ggagggttca | 60 |
| cgcaccggtg aacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgatgcc ccaagcgcaa gctacgccaa | 240 |

-continued

```
tccagggcag cgaatctcgt ctctgctgac ccagatccct gcttacacat gtcctcgcct      300
ccagtgccct cacagagctt gccgctagac gtatccgagt cgcattcctc aaatacctcc      360
cggcaatttc ttgatccacc ggacagctac gactggtcgt ggacctcgat tggcactgac      420
gaggcttttg acactgactg ctgggggcta tcccaatgtg atggaggctt cagctgtcag      480
ctagagccaa cgctgccgga tctaccttcg cccttcgagt ctacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatctttt tcaatgcgtc acgacggctt      720
cttactgtcc tgcgccagca agcgcaggcc gactgccatc aaggcacact agacgaatgt      780
ttacggacca agaacctctt tacggcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acatcagcag cagcagcggc      960
cacagcagtg ttgacaccat acccttcttt agcgagaacc tccctattgg tgagctgttc     1020
tcctatgttg accccctgac acacgcccta ttctcggctt gcactacgtt acatgttggg     1080
gtacaattgc tgcgtgagaa tgagattact ctgggagtac actccgccca gggcattgca     1140
gcttacatca gcaagagcgg ggaaccaggc gaggatatag ccaggacagg ggcgaccaat     1200
tccgcaagat gcgaggagca gccgaccact ccagcggctc gggtgttgtt catgttcttg     1260
agtgatgaag gggctttcca ggaggcaaag tctgctggtt cccgaggtcg aaccatcgca     1320
gcactgcgac gatgctatga ggatatcttt tccctcgccc gcaaacacaa acatggcatg     1380
ctcagagacc tcaacaatat tcctccatga                                      1410
```

<210> SEQ ID NO 86
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 86

```
atggctgcag atcaaggtat attcacgaac tcggtcactc tctcgccagt ggagggttca       60
cgcaccggtg gaacattacc ccgccgtgca ttccgacgct cttgtgatcg tgtcatgca       120 caaaagatca aatgtattgg aaataaggag gttactggcc gtgctccctg tcagcgttgc      180
caacgggctg gacttcgatg cgtctacagt gagcgatgcc ccaagcgcag gctacgccaa      240
tccagggcag cggatctcgt ctctgctgac ccagatccct gcttgcacat gtcctcgcct      300
ccagtgccct cacagagctt gccgctagac gtatccgagt cgcattcctc aaatacctcc      360
cggcaatttc ttgatccacc ggacagctac gactggtcgt ggacctcgat tggcactgac      420
gaggctattg acactgactg ctgggggctg tcccaatgtg atggaggctt cagctgtcag      480
ttagagccaa cgctgccgga tctaccttcg cccttcgagt ctacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcttc acgacggctt      720
cttactgtcc tgcgccaaca agctcaggcc gactgccatc aaggcacact agacgaatgt      780
ttacggacca agaacctctt tacggcagta cactgttaca tattgaatgt gcggattttg      840
```

```
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagctgtg tcgacaccat acccttcttt agcgagaacc tccctattgg tgagctgttc   1020
tcctatgttg acccctgac acacgcccta ttctcggctt gcactacgtt acatgttggg   1080
gtacaattgc tgcgtgagta tgagattact ctgggaatac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg   1380
ctcagagatc tcaacaatat tcctccatga                                    1410

<210> SEQ ID NO 87
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 87
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120
cgaaagatca aatgtactgg aaataaggag gttactggcc gtgctccctg tcagcgttgc    180
cagcaagctg gacttcgatg cgtctatagt gagcgatgcc ccaagcgcaa gctacgccaa    240
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctgggggctg tcccaatgtg atggaggctt cagctgtcag    480
ctagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga tccagaacag ccatatgagc    900
ccactggaag ggagtcgatc ccagtcgctg agcagagacg acaccagcag cagtagcggc    960
cacagcagtg ttgacaccat acccttcttt agcgagaacc tccctattga tgagctgttc   1020
tcctatgttg acccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaactaggc gaggatatag tcaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgagtcg aaccatcgca   1320
gcactgcgac gatgctatga ggatatcttt tccctcgccc gcaaacacaa acatggcatg   1380
ctcagagacc tcaacaatat tcctccatga                                    1410
```

<210> SEQ ID NO 88
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 88

| | | | | | |
|---|---|---|---|---|---|
| atggctgcag | atcaaggtat | attcacgaac | tcggtcactc | tctcaccagt | ggagggttca | 60 |
| cgcaccggtg | gaacattacc | ccgccgtgca | ttccgacgct | cttgtgatcg | gtgtcatgca | 120 |
| caaaagatca | aatgtactgg | aaataaggag | gttaatggcc | gtgctccctg | tcagcgttgc | 180 |
| cagcaggctg | gacttcgatg | cgtctacagt | gagcgatgcc | ccaagcgcaa | gctacgccaa | 240 |
| tccagggcag | cggatctcgt | ctctgctgac | ccagatccct | gcttgcacat | gtcctcgcct | 300 |
| ccagtgccct | cccagagctt | gccgctagac | atatccgagt | cgcattcctc | aaatacctcc | 360 |
| cggcaatttc | ttgatccacc | ggacagctac | gactggtcgt | ggacctcgat | tggcattgac | 420 |
| gaggctattg | acactgactg | ctgggggctg | tcccaatgtg | atggaggctt | cagctgtcag | 480 |
| ttagagccaa | cgctgccgga | tctaccttcg | cccttcgagt | ctacggttga | aaaagctccg | 540 |
| ttgccaccga | tatcgagcga | cattgctcgt | gcggccagtg | cgcaacgaga | gcttttcgat | 600 |
| gacctgtcgg | cggtgtcgca | ggaactggaa | gagatcccttc | tggccgtgac | ggtagaatgg | 660 |
| ccgaagcagg | aaatctggac | ccatcccatc | ggaatgtttt | tcaatgcgtc | acgacggctt | 720 |
| cttactgtcc | tgcgccaaca | agcgcaggcc | gactgccatc | aaggcacact | agacgaatgt | 780 |
| ttacggacca | agaacctctt | tacggcagta | cactgttaca | tattgaatgt | gcggattttg | 840 |
| gccgccatat | cggagttgct | cctgtcgcaa | attaggcgga | cccagaacag | ccatatgagc | 900 |
| ccactggaag | ggagtcgatc | ccagtcgccg | agcagagacg | acaccagcag | cagcagcggc | 960 |
| cacagcagtg | ttgacaccat | acccttcttt | agcgagaacc | tccctattgg | tgagctgttc | 1020 |
| tcctatgttg | acccccctgac | acacgcccta | ttctcggctt | gcactacgtt | acatgttggg | 1080 |
| gtacaattgc | tgcgtgagaa | tgagattact | ctgggagtac | actccgccca | gggcattgca | 1140 |
| gcttccatca | gcatgagcgg | ggaaccaggc | gaggatatag | ccaggacagg | ggcgaccaat | 1200 |
| tccgcaagat | gcgaggagca | gccgaccact | ccagcggctc | gggttttgtt | catgttcttg | 1260 |
| agtgatgaag | gggcttttcca | ggaggcaaag | tctgctggtt | cccgaggtcg | aaccatcgca | 1320 |
| gcactgcgac | gatgctatga | ggatatcttt | tccctcgccc | gcaaacacaa | acatggcatg | 1380 |
| ctcagagacc | tcaacaatat | tcctccatga | | | | 1410 |

<210> SEQ ID NO 89
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 89

| | | | | | |
|---|---|---|---|---|---|
| atggctgcag | aacaaggtat | attcacgaac | tcggtcactc | tctcgccagt | ggagggttca | 60 |
| cgcaccggtg | gaacattacc | ccgccgtgca | ttccgacgct | cttgtgatcg | gtgtcatgca | 120 |
| cgaaagatca | aatgtactgg | aaataaggag | gttactggcc | gtgctccctg | tcagcgttgc | 180 |
| cagcaggctg | gacttcgatg | tgtctacagt | gagcgatgcc | ccaagcgcaa | gctacgccaa | 240 |
| tccagggcag | cggatctcat | ctctgctgac | ccagatccct | gcttgcacat | gtcctcgcct | 300 |
| ccagtgccct | cacagagctt | gccgctagaa | gtatccgagt | cgcattcctc | aaatacctcc | 360 |

-continued

```
cggcaatttc ttgatccacc ggacagctac gactggtcgt ggacctcgat tggcactgac      420
aaggctattg acactgactg ctgggggctg tcccaatgtg atggaggctt cagctgtcag      480
ttagagccaa cgctgccgga tctaccttcg ccctttgagt ctacggttga aaaagctccg      540
ttgccaccgg tatcgagcga cattactcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcgtc acgacggctt      720
cttactgtcc tgcgccaaca agcgcaggcc gactgccatc aaggcacact agacgaatgt      780
ttacggacca agaacctctt tacggcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acaccagcag cagcagcggc      960
cacagcagtg ttgacaccat accttctttt agcgagaacc tccctattgg tgagctgttc     1020
tcctatgttg accccctgag acacgcccta ttctcggctt gcactacgtt acatgttggg     1080
gtacaattgc tgcgtgagat tgagattact ctgggagtac actccgcccg ggcattgca      1140
gcttccatca gcatgagcgg ggaaccaggc gaggatatag ccaggacagg ggcgaccaat     1200
tccgcaagat gcgaggagca gccgaccact ccagcggctc gggttttgtt catgttcttg     1260
agtgatgaag ggactttcca ggaggcaaag tctgctggtt cccgaggtcg aaccatcgca     1320
gcactgcgac gatgctatga ggatatcttt ccctcgccc gcaaacacaa acatggcatg     1380
ctcagagacc tcaacaatat tcctccatga                                     1410
```

<210> SEQ ID NO 90
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 90

```
atggctgcag atcaaggtat attcacgaac tcggtcactc tctcgccagt ggagggttca       60
cgcaccggtg gaacattacc ccgccgtgca ttccgacgct cttgtgatcg gtgtcatgca      120
caaaagatca aatgtactgg aaataaggag gttactggcc gtgctccctg tcagcgttgc      180
cagcaggctg gacttcgatg cgtctacagt gagcgatgcc ccaagcgcaa gctacgccaa      240
tccagggcag cggatctcgt ctctgctgac ccagatccct gcttgcacat gtcctcacct      300
ccagtgccct cacagagctt gccgctagac gtatccgagt cgcattcctc aaataccctcc     360
cggcaatttc ttgatccacc ggacagctac aactggttgt ggacctcgat tggcactgac      420
gaggctattg acactgactg ctgggggctg tcccaatgtg atggaggctt cagctgtcag      480
ttagagccaa cgctgccgga tctaccttcg cccttcgaat ctacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcgtc acgacggctt      720
cttactgtcc tgcgccaaca agcgcaggcc gactgccatc aaggcacact agacgaatgt      780
ttacggacca agaacctctt tacggcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcggagacg acaccagcag cagcagcggc      960
cacagcagtg ttgacaccat accttctttt agcgagaacc tccctattgg tgagctgttc     1020
```

-continued

```
tcctatgttg acccccctgac acacgccta ttctcggctt gcactacgtt acatgttggg    1080
gtacaattgc tgcgtgagaa tgagattact ctgggagtac actccgccca gggtattgca    1140
gcttccatca gcatgagcgg ggaaccaggc gaggatatag ccaggacagg ggcgaccaat    1200
tccgcaagat gcgaggagca gccgaccact ccagcggctc gggttttgtt catgttcttg    1260
agtgatgaag gggcttttcca ggagggaaag tctgctggtt cccgaggtcg aaccatcgca    1320
gcactgcgac gatgctatga ggatatcttt tccctcgccc gcaaacacaa acatggcatg    1380
ctcagagacc tcaacaatat tcctccatga                                      1410
```

<210> SEQ ID NO 91
<211> LENGTH: 469
<212> TYPE: PRT
<213> ORGANISM: Aspergillus terreus

<400> SEQUENCE: 91

```
Met Ala Ala Asp Gln Gly Ile Phe Thr Asn Ser Val Thr Leu Ser Pro
  1               5                  10                  15

Val Glu Gly Ser Arg Thr Gly Gly Thr Leu Pro Arg Arg Ala Phe Arg
             20                  25                  30

Arg Ser Cys Asp Arg Cys His Ala Gln Lys Ile Lys Cys Thr Gly Asn
         35                  40                  45

Lys Glu Val Thr Gly Arg Ala Pro Cys Gln Arg Cys Gln Gln Ala Gly
     50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300
```

```
Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
450                 455                 460

Asn Asn Ile Pro Pro
465

<210> SEQ ID NO 92
<211> LENGTH: 1410
<212> TYPE: DNA
<213> ORGANISM: Aspergillus terreus

<400> SEQUENCE: 92
atggctgcag atcaaggtat attcacgaac tcggtcactc tctcgccagt ggagggttca      60
cgcaccggtg gaacattacc ccgccgtgca ttccgacgct cttgtgatcg gtgtcatgca     120
caaaagatca aatgtactgg aaataaggag gttactggcc gtgctccctg tcagcgttgc     180
cagcaggctg gacttcgatg cgtctacagt gagcgatgcc caagcgcaa gctacgccaa      240 tccagggcag cggatctcgt ctctgctgac ccagatccct gcttgcacat gtcctcgcct     300
ccagtgccct cacagagctt gccgctagac gtatccgagt cgcattcctc aaatacctcc     360
cggcaatttc ttgatccacc ggacagctac gactggtcgt ggacctcgat tggcactgac     420
gaggctattg acactgactg ctgggggctg tcccaatgtg atggaggctt cagctgtcag     480
ttagagccaa cgctgccgga tctaccttcg cccttcgagt ctacggttga aaaagctccg     540
ttgccaccgg tatcgagcga cattgctcgt gcggccagtg cgcaacgaga gcttttcgat     600
gacctgtcgg cggtgtcgca ggaactggaa gagatccttc tggccgtgac ggtagaatgg     660
ccgaagcagg aaatctggac ccatcccatc ggaatgtttt tcaatgcgtc acgacggctt     720
cttactgtcc tgcgccaaca agcgcaggcc gactgccatc aaggcacact agacgaatgt     780
ttacggacca agaacctctt tacggcagta cactgttaca tattgaatgt gcggattttg     840
accgccatat cggagttgct cctgtcgcaa attaggcgga cccagaacag ccatatgagc     900
ccactggaag ggagtcgatc ccagtcgccg agcagagacg acaccagcag cagcagcggc     960
cacagcagtg ttgacaccat accttctttt agcgagaacc tccctattgg tgagctgttc    1020
tcctatgttg accccctgac acacgcccta ttctcggctt gcactacgtt acatgttggg    1080
gtacaattgc tgcgtgagaa tgagattact ctgggagtac actccgccca gggcattgca    1140
```

```
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                     1410
```

<210> SEQ ID NO 93
<211> LENGTH: 480
<212> TYPE: PRT
<213> ORGANISM: Aspergillus terreus

<400> SEQUENCE: 93

```
Met Thr Gln Asp Thr Ala Gln Tyr Arg Gly Ala Met Ala Ala Asp Gln
 1               5                   10                  15

Gly Ile Phe Thr Asn Ser Val Thr Leu Ser Pro Val Glu Gly Ser Arg
                20                  25                  30

Thr Gly Gly Thr Leu Pro Arg Arg Ala Phe Arg Arg Ser Cys Asp Arg
            35                  40                  45

Cys His Ala Gln Lys Ile Lys Cys Thr Gly Asn Lys Glu Val Thr Gly
        50                  55                  60

Arg Ala Pro Cys Gln Arg Cys Gln Gln Ala Gly Leu Arg Cys Val Tyr
 65                  70                  75                  80

Ser Glu Arg Cys Pro Lys Arg Lys Leu Arg Gln Ser Arg Ala Ala Asp
                85                  90                  95

Leu Val Ser Ala Asp Pro Asp Pro Cys Leu His Met Ser Ser Pro Pro
            100                 105                 110

Val Pro Ser Gln Ser Leu Pro Leu Asp Val Ser Glu Ser His Ser Ser
        115                 120                 125

Asn Thr Ser Arg Gln Phe Leu Asp Pro Pro Asp Ser Tyr Asp Trp Ser
    130                 135                 140

Trp Thr Ser Ile Gly Thr Asp Glu Ala Ile Asp Thr Asp Cys Trp Gly
145                 150                 155                 160

Leu Ser Gln Cys Asp Gly Gly Phe Ser Cys Gln Leu Glu Pro Thr Leu
                165                 170                 175

Pro Asp Leu Pro Ser Pro Phe Glu Ser Thr Val Glu Lys Ala Pro Leu
            180                 185                 190

Pro Pro Val Ser Ser Asp Ile Ala Arg Ala Ala Ser Ala Gln Arg Glu
        195                 200                 205

Leu Phe Asp Asp Leu Ser Ala Val Ser Gln Glu Leu Glu Glu Ile Leu
    210                 215                 220

Leu Ala Val Thr Val Glu Trp Pro Lys Gln Glu Ile Trp Thr His Pro
225                 230                 235                 240

Ile Gly Met Phe Phe Asn Ala Ser Arg Arg Leu Leu Thr Val Leu Arg
                245                 250                 255

Gln Gln Ala Gln Ala Asp Cys His Gln Gly Thr Leu Asp Glu Cys Leu
            260                 265                 270

Arg Thr Lys Asn Leu Phe Thr Ala Val His Cys Tyr Ile Leu Asn Val
        275                 280                 285

Arg Ile Leu Thr Ala Ile Ser Glu Leu Leu Ser Gln Ile Arg Arg
    290                 295                 300

Thr Gln Asn Ser His Met Ser Pro Leu Glu Gly Ser Arg Ser Gln Ser
305                 310                 315                 320
```

```
Pro Ser Arg Asp Asp Thr Ser Ser Ser Gly His Ser Ser Val Asp
            325                 330                 335

Thr Ile Pro Phe Phe Ser Glu Asn Leu Pro Ile Gly Glu Leu Phe Ser
            340                 345                 350

Tyr Val Asp Pro Leu Thr His Ala Leu Phe Ser Ala Cys Thr Thr Leu
            355                 360                 365

His Val Gly Val Gln Leu Leu Arg Glu Asn Glu Ile Thr Leu Gly Val
            370                 375                 380

His Ser Ala Gln Gly Ile Ala Ala Ser Ile Ser Met Ser Gly Glu Pro
385                 390                 395                 400

Gly Glu Asp Ile Ala Arg Thr Gly Ala Thr Asn Ser Ala Arg Cys Glu
                405                 410                 415

Glu Gln Pro Thr Thr Pro Ala Ala Arg Val Leu Phe Met Phe Leu Ser
            420                 425                 430

Asp Glu Gly Ala Phe Gln Glu Ala Lys Ser Ala Gly Ser Arg Gly Arg
            435                 440                 445

Thr Ile Ala Ala Leu Arg Arg Cys Tyr Glu Asp Ile Phe Ser Leu Ala
            450                 455                 460

Arg Lys His Lys His Gly Met Leu Arg Asp Leu Asn Asn Ile Pro Pro
465                 470                 475                 480

<210> SEQ ID NO 94
<211> LENGTH: 482
<212> TYPE: PRT
<213> ORGANISM: Aspergillus terreus

<400> SEQUENCE: 94

Met Leu Met Thr Gln Asp Thr Ala Gln Tyr Arg Gly Ala Met Ala Ala
1               5                   10                  15

Asp Gln Gly Ile Phe Thr Asn Ser Val Thr Leu Ser Pro Val Glu Gly
            20                  25                  30

Ser Arg Thr Gly Gly Thr Leu Pro Arg Arg Ala Phe Arg Ser Cys
        35                  40                  45

Asp Arg Cys His Ala Gln Lys Ile Lys Cys Thr Gly Asn Lys Glu Val
        50                  55                  60

Thr Gly Arg Ala Pro Cys Gln Arg Cys Gln Gln Ala Gly Leu Arg Cys
65                  70                  75                  80

Val Tyr Ser Glu Arg Cys Pro Lys Arg Lys Leu Arg Gln Ser Arg Ala
                85                  90                  95

Ala Asp Leu Val Ser Ala Asp Pro Asp Pro Cys Leu His Met Ser Ser
            100                 105                 110

Pro Pro Val Pro Ser Gln Ser Leu Pro Leu Asp Val Ser Glu Ser His
            115                 120                 125

Ser Ser Asn Thr Ser Arg Gln Phe Leu Asp Pro Pro Asp Ser Tyr Asp
        130                 135                 140

Trp Ser Trp Thr Ser Ile Gly Thr Asp Glu Ala Ile Asp Thr Asp Cys
145                 150                 155                 160

Trp Gly Leu Ser Gln Cys Asp Gly Gly Phe Ser Cys Gln Leu Glu Pro
                165                 170                 175

Thr Leu Pro Asp Leu Pro Ser Pro Phe Glu Ser Thr Val Glu Lys Ala
            180                 185                 190

Pro Leu Pro Pro Val Ser Ser Asp Ile Ala Arg Ala Ala Ser Ala Gln
            195                 200                 205

Arg Glu Leu Phe Asp Asp Leu Ser Ala Val Ser Gln Glu Leu Glu Glu
        210                 215                 220
```

-continued

```
Ile Leu Leu Ala Val Thr Val Glu Trp Pro Lys Gln Glu Ile Trp Thr
225                 230                 235                 240

His Pro Ile Gly Met Phe Phe Asn Ala Ser Arg Arg Leu Leu Thr Val
            245                 250                 255

Leu Arg Gln Gln Ala Gln Ala Asp Cys His Gln Gly Thr Leu Asp Glu
        260                 265                 270

Cys Leu Arg Thr Lys Asn Leu Phe Thr Ala Val His Cys Tyr Ile Leu
    275                 280                 285

Asn Val Arg Ile Leu Thr Ala Ile Ser Glu Leu Leu Leu Ser Gln Ile
290                 295                 300

Arg Arg Thr Gln Asn Ser His Met Ser Pro Leu Glu Gly Ser Arg Ser
305                 310                 315                 320

Gln Ser Pro Ser Arg Asp Asp Thr Ser Ser Ser Gly His Ser Ser
            325                 330                 335

Val Asp Thr Ile Pro Phe Phe Ser Glu Asn Leu Pro Ile Gly Glu Leu
            340                 345                 350

Phe Ser Tyr Val Asp Pro Leu Thr His Ala Leu Phe Ser Ala Cys Thr
        355                 360                 365

Thr Leu His Val Gly Val Gln Leu Leu Arg Glu Asn Glu Ile Thr Leu
    370                 375                 380

Gly Val His Ser Ala Gln Gly Ile Ala Ala Ser Ile Ser Met Ser Gly
385                 390                 395                 400

Glu Pro Gly Glu Asp Ile Ala Arg Thr Gly Ala Thr Asn Ser Ala Arg
            405                 410                 415

Cys Glu Glu Gln Pro Thr Thr Pro Ala Ala Arg Val Leu Phe Met Phe
        420                 425                 430

Leu Ser Asp Glu Gly Ala Phe Gln Glu Ala Lys Ser Ala Gly Ser Arg
    435                 440                 445

Gly Arg Thr Ile Ala Ala Leu Arg Arg Cys Tyr Glu Asp Ile Phe Ser
    450                 455                 460

Leu Ala Arg Lys His Lys His Gly Met Leu Arg Asp Leu Asn Asn Ile
465                 470                 475                 480

Pro Pro

<210> SEQ ID NO 95
<211> LENGTH: 11
<212> TYPE: PRT
<213> ORGANISM: Aspergillus terreus

<400> SEQUENCE: 95

Met Thr Gln Asp Thr Ala Gln Tyr Arg Gly Ala
1               5                   10

<210> SEQ ID NO 96
<211> LENGTH: 13
<212> TYPE: PRT
<213> ORGANISM: Aspergillus terreus

<400> SEQUENCE: 96

Met Leu Met Thr Gln Asp Thr Ala Gln Tyr Arg Gly Ala
1               5                   10

<210> SEQ ID NO 97
<211> LENGTH: 469
<212> TYPE: PRT
<213> ORGANISM: Artificial Sequence
<220> FEATURE:
```

-continued

<223> OTHER INFORMATION: synthetically generated variant

<400> SEQUENCE: 97

```
Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Val Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400
```

```
Ser Ala Arg Cys Glu Glu Gln Pro Thr Thr Pro Ala Ala Arg Val Leu
            405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
450                 455                 460

Asn Asn Ile Pro Pro
465

<210> SEQ ID NO 98
<211> LENGTH: 469
<212> TYPE: PRT
<213> ORGANISM: Artificial Sequence
<220> FEATURE:
<223> OTHER INFORMATION: synthetically generated variant

<400> SEQUENCE: 98

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
            50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
            130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
            210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
            275                 280                 285
```

```
Ser Gln Ile Arg Arg Thr Gln Asn Ser His Met Ser Pro Leu Glu Gly
    290                 295                 300

Ser Arg Ser Gln Ser Pro Ser Arg Asp Glu Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Lys Gly Ala Thr Asn
385                 390                 395                 400

Ser Ala Arg Cys Glu Glu Gln Pro Thr Thr Pro Ala Ala Arg Val Leu
                405                 410                 415

Phe Leu Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 99
<211> LENGTH: 469
<212> TYPE: PRT
<213> ORGANISM: Artificial Sequence
<220> FEATURE:
<223> OTHER INFORMATION: synthetically generated variant

<400> SEQUENCE: 99

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Thr Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175
```

```
Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Ile Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 100
<211> LENGTH: 468
<212> TYPE: PRT
<213> ORGANISM: Artificial Sequence
<220> FEATURE:
<223> OTHER INFORMATION: synthetically generated variant

<400> SEQUENCE: 100

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60
```

```
Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Ile Ser Arg Gln Phe Leu Asp Pro Pro Asp
            115                 120                 125

Ser Tyr Asp Trp Ser Trp Thr Ser Ile Gly Thr Asp Glu Ala Ile Asp
        130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Gly His
305                 310                 315                 320

Ser Ser Val Asp Thr Ile Pro Phe Phe Ser Glu Asn Leu Pro Ile Gly
            325                 330                 335

Glu Leu Phe Ser Tyr Val Asp Pro Leu Thr His Ala Leu Phe Ser Ala
            340                 345                 350

Cys Thr Thr Leu His Val Gly Val Gln Leu Leu Arg Glu Asn Glu Ile
            355                 360                 365

Thr Leu Gly Val His Ser Ala Gln Gly Ile Ala Ala Ser Ile Ser Met
    370                 375                 380

Ser Gly Glu Pro Gly Glu Asp Ile Ala Arg Thr Gly Ala Thr Asn Ser
385                 390                 395                 400

Ala Arg Cys Glu Glu Gln Pro Thr Thr Pro Ala Ala Arg Val Leu Phe
            405                 410                 415

Met Phe Leu Thr Asp Glu Gly Ala Phe Gln Glu Ala Lys Ser Ala Gly
            420                 425                 430

Ser Arg Gly Arg Thr Ile Ala Ala Leu Arg Arg Cys Tyr Glu Asp Ile
            435                 440                 445

Phe Ser Leu Ala Arg Lys His Lys His Gly Met Leu Arg Asp Leu Asn
450                 455                 460

Asn Ile Pro Pro
465
```

-continued

<210> SEQ ID NO 101
<211> LENGTH: 469
<212> TYPE: PRT
<213> ORGANISM: Artificial Sequence
<220> FEATURE:
<223> OTHER INFORMATION: synthetically generated variant

<400> SEQUENCE: 101

```
Met Ala Ala Asp Gln Gly Ile Phe Thr Asn Ser Val Thr Leu Ser Pro
 1               5                  10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Leu Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Leu Ser Glu Leu Leu Leu
        275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
```

```
                    370                 375                 380
Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
                435                 440                 445

Ile Phe Ser Leu Ala Arg Lys His Lys His Gly Met Leu Arg Asp Leu
            450                 455                 460

Asn Asn Ile Pro Pro
465

<210> SEQ ID NO 102
<211> LENGTH: 469
<212> TYPE: PRT
<213> ORGANISM: Artificial Sequence
<220> FEATURE:
<223> OTHER INFORMATION: synthetically generated variant

<400> SEQUENCE: 102

Met Ala Ala Asp Gln Gly Ile Phe Thr Asn Ser Val Thr Leu Ser Pro
  1               5                  10                  15

Val Glu Gly Ser Arg Thr Gly Thr Leu Pro Arg Arg Ala Phe Arg
                 20                  25                  30

Arg Ser Cys Asp Arg Cys His Ala Gln Lys Ile Lys Cys Thr Gly Asn
             35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Cys Pro Lys His Lys Leu Arg Gln
 65                  70                  75                  80

Ser Arg Ala Ala Asp Leu Val Ser Ala Asp Pro Asp Pro Cys Leu Arg
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
            210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
```

```
                    260                 265                 270
Tyr Ile Leu Asn Val Arg Ile Leu Thr Ala Ile Ser Glu Leu Leu
            275                 280                 285
Ser Gln Ile Arg Arg Thr Gln Asn Ser His Met Ser Pro Leu Glu Gly
        290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
            355                 360                 365
Ile Thr Leu Gly Val His Ser Ala Gln Gly Ile Ala Ala Ser Ile Ser
        370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
        435                 440                 445
Ile Phe Ser Leu Ala Arg Lys His Lys His Gly Met Phe Arg Asp Leu
    450                 455                 460
Asn Asn Ile Pro Pro
465

<210> SEQ ID NO 103
<211> LENGTH: 469
<212> TYPE: PRT
<213> ORGANISM: Artificial Sequence
<220> FEATURE:
<223> OTHER INFORMATION: synthetically generated variant

<400> SEQUENCE: 103

Met Ala Ala Asp Gln Gly Ile Phe Thr Asn Ser Val Thr Leu Ser Pro
  1               5                  10                  15
Val Glu Gly Ser Arg Thr Gly Gly Thr Leu Pro Arg Arg Ala Phe Arg
             20                  25                  30
Arg Ser Cys Asp Arg Cys His Ala Gln Lys Ile Lys Cys Thr Gly Asn
         35                  40                  45
Lys Glu Val Thr Gly Arg Ala Pro Cys Gln Arg Cys Gln Gln Ala Gly
     50                  55                  60
Leu Arg Cys Val Tyr Ser Glu Arg Cys Pro Lys Arg Lys Leu Arg Gln
 65                  70                  75                  80
Ser Arg Ala Ala Asp Leu Val Ser Ala Asp Pro Asp Cys Leu His
                 85                  90                  95
Met Ser Ser Pro Pro Val Pro Ser Gln Ser Leu Pro Leu Asp Val Ser
                100                 105                 110
Glu Ser His Ser Ser Asn Thr Ser Arg Gln Phe Leu Asp Pro Pro Asp
            115                 120                 125
Ser Tyr Asp Trp Ser Trp Thr Ser Ile Gly Thr Asp Glu Ala Ile Asp
        130                 135                 140
Thr Asp Cys Trp Gly Leu Ser Gln Cys Asp Gly Gly Phe Ser Cys Gln
```

```
                145                 150                 155                 160
Leu Glu Pro Thr Leu Pro Asp Leu Pro Ser Pro Phe Glu Ser Thr Val
                    165                 170                 175
Glu Lys Ala Pro Leu Pro Pro Val Ser Arg Asp Ile Ala Arg Ala Ala
                180                 185                 190
Ser Ala Gln Arg Glu Leu Phe Asp Asp Leu Ser Ala Val Ser Gln Glu
                195                 200                 205
Leu Glu Glu Ile Leu Leu Ala Val Thr Val Glu Trp Pro Lys Gln Glu
            210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                    245                 250                 255
Leu Asp Glu Cys Leu Arg Thr Lys Asn Leu Phe Thr Ala Val His Cys
                260                 265                 270
Tyr Ile Leu Asn Val Arg Ile Leu Thr Ala Ile Ser Glu Leu Leu Gln
                275                 280                 285
Ser Gln Ile Arg Arg Thr Gln Asn Ser His Met Ser Pro Leu Glu Gly
            290                 295                 300
Ser Arg Ser Gln Ser Pro Ser Lys Asp Asp Thr Ser Ser Ser Ser Gly
305                 310                 315                 320
His Ser Ser Val Asp Thr Ile Pro Phe Phe Ser Glu Asn Leu Pro Ile
                    325                 330                 335
Gly Glu Leu Phe Ser Tyr Val Asp Pro Leu Thr His Ala Leu Phe Ser
                340                 345                 350
Ala Cys Thr Thr Leu His Val Gly Val Gln Leu Leu Arg Glu Asn Glu
                355                 360                 365
Ile Thr Leu Gly Val His Ser Ala Gln Gly Ile Ala Ala Ser Ile Ser
            370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                    405                 410                 415
Phe Met Phe Leu Ser Asp Glu Gly Ala Phe Gln Glu Ala Lys Ser Ala
                420                 425                 430
Gly Ser Arg Gly Arg Thr Ile Ala Ala Leu Arg Arg Cys Tyr Glu Asp
                435                 440                 445
Ile Phe Ser Leu Ala Arg Lys His Lys His Gly Met Leu Arg Asp Leu
            450                 455                 460
Asn Asn Ile Pro Pro
465

<210> SEQ ID NO 104
<211> LENGTH: 469
<212> TYPE: PRT
<213> ORGANISM: Artificial Sequence
<220> FEATURE:
<223> OTHER INFORMATION: synthetically generated variant

<400> SEQUENCE: 104

Met Ala Ala Asp Gln Gly Ile Phe Thr Asn Ser Val Thr Leu Ser Pro
1               5                   10                  15
Val Glu Gly Ser Arg Thr Gly Gly Thr Leu Pro Arg Arg Ala Phe Arg
                20                  25                  30
Arg Ser Cys Asp Arg Cys His Ala Gln Lys Ile Lys Cys Thr Gly Asn
```

-continued

```
                35                  40                  45
Lys Glu Val Thr Gly Arg Ala Pro Cys Gln Arg Cys Gln Gln Ala Gly
 50                  55                  60
Leu Arg Cys Val Tyr Ser Glu Arg Cys Pro Lys Arg Lys Leu Arg Gln
 65                  70                  75                  80
Ser Arg Ala Ala Asp Leu Val Ser Ala Asp Pro Asp Pro Cys Leu His
                 85                  90                  95
Met Ser Ser Pro Pro Val Pro Ser Gln Ser Leu Pro Leu Asp Val Pro
                100                 105                 110
Glu Ser His Ser Ser Asn Thr Ser Arg Gln Phe Leu Asp Pro Pro Asp
                115                 120                 125
Ser Tyr Asp Trp Ser Trp Thr Ser Ile Gly Thr Asp Glu Ala Ile Asp
                130                 135                 140
Thr Asp Cys Trp Gly Leu Ser Gln Cys Asp Gly Gly Phe Ser Cys Gln
145                 150                 155                 160
Leu Glu Pro Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
                180                 185                 190
Ser Ala Gln Arg Glu Leu Phe Asp Asp Leu Ser Thr Val Ser Gln Glu
                195                 200                 205
Leu Glu Glu Ile Leu Leu Ala Val Thr Val Glu Trp Pro Lys Gln Glu
                210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
                260                 265                 270
Tyr Ile Leu Asn Val Arg Ile Leu Thr Ala Ile Ser Glu Leu Leu Leu
                275                 280                 285
Ser Gln Ile Arg Arg Thr Gln Asn Ser His Met Ser Pro Leu Glu Gly
                290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
                340                 345                 350
Ala Cys Thr Thr Leu His Val Gly Val Gln Leu Leu Arg Glu Asn Glu
                355                 360                 365
Ile Thr Leu Gly Val His Ser Ala Gln Gly Ile Ala Ala Ser Ile Ser
                370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
                420                 425                 430
Gly Ser Arg Gly Arg Thr Ile Ala Ala Leu Arg Arg Cys Tyr Glu Asp
                435                 440                 445
Ile Phe Ser Leu Ala Arg Lys His Lys His Gly Met Leu Arg Asp Leu
                450                 455                 460
```

```
Asn Asn Ile Pro Pro
465

<210> SEQ ID NO 105
<211> LENGTH: 366
<212> TYPE: PRT
<213> ORGANISM: Artificial Sequence
<220> FEATURE:
<223> OTHER INFORMATION: synthetically generated variant

<400> SEQUENCE: 105

Met Ala Ala Asp Gln Gly Ile Phe Thr Asn Ser Val Thr Leu Ser Pro
 1               5                  10                  15

Leu Glu Gly Ser Arg Thr Gly Gly Thr Leu Pro Arg Arg Ala Phe Arg
            20                  25                  30

Arg Ser Cys Asp Arg Cys Leu Ala Gln Lys Ile Lys Cys Thr Gly Asn
        35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Ser
            260                 265                 270

Ala Gln Gly Ile Ala Ala Ser Ile Ser Met Ser Gly Glu Pro Gly Glu
        275                 280                 285

Asp Ile Ala Arg Thr Gly Ala Thr Asn Ser Ala Arg Cys Glu Glu Gln
    290                 295                 300

Pro Thr Thr Pro Ala Ala Arg Val Leu Phe Met Phe Leu Ser Asp Glu
305                 310                 315                 320

Gly Ala Phe Gln Glu Ala Lys Ser Ala Gly Ser Arg Gly Arg Thr Ile
                325                 330                 335

Ala Ala Leu Arg Arg Cys Tyr Glu Asp Ile Phe Ser Leu Ala Arg Lys
            340                 345                 350
```

His Lys His Gly Met Leu Arg Asp Leu Asn Asn Ile Pro Pro
         355                 360                 365

<210> SEQ ID NO 106
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 106

| | | | | | |
|---|---|---|---|---|---|
| atggctgcag | atcaaggtat | attcacgaac | tcggtcactc | tctcgccagt | ggagggttca | 60 |
| cgcaccggtg | aacattacc | ccgccgtgca | ttccgacgct | cttgtgatcg | gtgtcatgca | 120 |
| caaaagatca | aatgtactgg | aaataaggag | gttactggcc | gtgctccctg | tcagcgttgc | 180 |
| cagcaggctg | gacttcgatg | cgtctacagt | gagcgatgcc | ccaagcgcaa | gctacgccaa | 240 |
| tccagggcag | cggatctcgt | ctctgctgac | ccagatccct | gcttgcacat | gtcctcgcct | 300 |
| ccagtgccct | cacagagctt | gccgctagac | gtatccgagt | cgcattcctc | aaatacctcc | 360 |
| cggcaatttc | ttgatccacc | ggacagctac | gactggtcgt | ggacctcgat | tggcactgac | 420 |
| gaggctattg | acactgactg | ctgggggctg | tcccaatgtg | atggaggctt | cagctgtcag | 480 |
| ttagagccaa | cgctgccgga | tctaccttcg | cccttcgagt | ctacggttga | aaaagctccg | 540 |
| ttgccaccgg | tatcgagcga | cattgctcgt | gcggccagtg | cgcaacgaga | gcttttcgat | 600 |
| gacctgtcgg | cggtgtcgca | ggaactggaa | gaaatccttc | tggccgtgac | ggtagaatgg | 660 |
| ccgaagcagg | aaatctggac | ccatcccatc | ggaatgtttt | tcaatgcgtc | acgacggctt | 720 |
| cttactgtcc | tgcgccaaca | agcgcaggcc | gactgccatc | aaggcacact | agacgaatgt | 780 |
| ttacggacca | agaacctctt | tacggcagta | cactgttaca | tattgaatgt | gcggattttg | 840 |
| accgccatat | cggagttgct | cctgtcgcaa | attaggcgga | cccagaacag | ccatatgagc | 900 |
| ccactggtag | ggagtcgatc | ccagtcgccg | agcagagacg | acaccagcag | cagcagcggc | 960 |
| cacagcagtg | ttgacaccat | acccttcttt | agcgagaacc | tcctattgg | tgagctgttc | 1020 |
| tcctatgttg | accccctgac | acacgcccta | ttctcggctt | gcactacgtt | acatgttggg | 1080 |
| gtacaattgc | tgcgtgagaa | tgagattact | ctgggagtac | actccgccca | ggcattgca | 1140 |
| gcttccatca | gcatgagcgg | ggaaccaggc | gaggatatag | ccaggacagg | ggcgaccaat | 1200 |
| tccgcaagat | gcgaggagca | gccgaccact | ccagcggctc | gggttttgtt | catgttcttg | 1260 |
| agtgatgaag | gggcttttcca | ggaggcaaag | tctgctggtt | cccgaggtcg | aaccatcgca | 1320 |
| gcactgcgac | gatgctatga | ggatatcttt | tccctcgccc | gcaaacacaa | acatggcatg | 1380 |
| ctcagagacc | tcaacaatat | tcctccatga | | | | 1410 |

<210> SEQ ID NO 107
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 107

| | | | | | |
|---|---|---|---|---|---|
| atggctgcag | atcaaggtat | attcacgaac | tcggtcactc | tctcgccagt | ggagggttca | 60 |
| cgcaccggtg | aacattacc | ccgccgtgca | ttccgacgct | cttgtgatcg | gtgtcatgca | 120 |
| caaaagatca | aatgtactgg | aaataaggag | gttactggcc | gtgctccctg | tcagcgttgc | 180 |
| cagcaggctg | gacttcgatg | cgtctacagt | gagcgatgcc | ccaagcgcaa | gctacgccaa | 240 |

```
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg agaccagcag cagcagcggc    960
cacagcagtg ttgacaccat acccttcttt agcgagaacc tccctattgg tgagctgttc   1020
tcctatgttg acccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggaaagg ggcgaccaat   1200
tccgcaagat gcgaggagca gccgaccact ccagcggctc gggttttgtt cttgttcttg   1260
agtgatgaag gggctttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                    1410

<210> SEQ ID NO 108
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 108
atggctgcag atcaaggtat attcacgaac tcggtcactc tctcgccagt ggagggttca     60
cgcaccggtg gaacattacc ccgccgtgca ttccgacgct cttgtgatcg gtgtcataca    120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
```

-continued

| | |
|---|---|
| accgccatat cggagttgct cctgtcgcaa attaggcgga cccagaacag ccatataagc | 900 |
| ccactggaag ggagtcgatc ccagtcgccg agcagagacg acaccagcag cagcagcggc | 960 |
| cacagcagtg ttgacaccat acccttcttt agcgagaacc tccctattgg tgagctgttc | 1020 |
| tcctatgttg acccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcttttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 109
<211> LENGTH: 1407
<212> TYPE: DNA
<213> ORGANISM: Artificial Sequence
<220> FEATURE:
<223> OTHER INFORMATION: synthetically generated variant

<400> SEQUENCE: 109

| | |
|---|---|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgatgcc ccaagcgcaa gctacgccaa | 240 |
| tccagggcag cggatctcgt tctgctgac ccagatccct gcttgcacat gtcctcgcct | 300 |
| ccagtgccct cacagagctt gccgctagac gtatccgagt cgcattcctc aaatatctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctcca | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac agtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcggccac | 960 |
| agcagtgttg acaccatacc cttctttagc gagaacctcc ctattggtga gctgttctcc | 1020 |
| tatgttgacc cctgacaca cgccctattc tcggcttgca ctacgttaca tgttggggta | 1080 |
| caattgctgc gtgagaatga gattactctg ggagtacact ccgcccaggg cattgcagct | 1140 |
| tccatcagca tgagcgggga accaggcgag gatatagcca ggacagggc gaccaattcc | 1200 |
| gcaagatgcg aggagcagcc gaccactcca gcggctcggg ttttgttcat gttcttgact | 1260 |
| gatgaagggg ctttcagga ggcaaagtct gctggttccc gaggtcgaac catcgcagca | 1320 |
| ctgcgacgat gctatgagga tatcttttcc ctcgcccgca aacacaaaca tggcatgctc | 1380 |
| agagacctca acaatattcc tccatga | 1407 |

<210> SEQ ID NO 110
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 110

| | | | | | |
|---|---|---|---|---|---|
| atggctgcag | atcaaggtat | attcacgaac | tcggtcactc | tctcgccagt | ggagggttca | 60 |
| cgcaccggtg | gaacattacc | ccgccgtgca | ttccgacgct | cttgtgatcg | gtgtcatgca | 120 |
| caaaagatca | aatgtactgg | aaataaggag | gttactggcc | gtgctccctg | tcagcgttgc | 180 |
| cagcaggctg | gacttcgatg | cgtctacagt | gagcgatgcc | ccaagcgcaa | gctacgccaa | 240 |
| tccagggcag | cggatctcgt | ctctgctgac | ccagatccct | gcttgcacat | gtcctcgcct | 300 |
| ccagtgccct | cacagagctt | gccgctagac | gtatccgagt | cgcattcctc | aaatacctcc | 360 |
| cggcaatttc | ttgatccacc | ggacagctac | gactggtcgt | ggacctcgat | tggcactgac | 420 |
| gaggctattg | acactgactg | ctgggggctg | tcccaatgtg | atggaggctt | cagctgtcag | 480 |
| ttagagccaa | cgctgccgga | tctaccttcg | cccttcgagt | ctacggttga | aaaagctccg | 540 |
| ttgccactgg | tatcgagcga | cattgctcgt | gcggccagtg | cgcaacgaga | gcttttcgat | 600 |
| gacctgtcgg | cggtgtcgca | ggaactggaa | gagatcctcc | tggccgtgac | ggtagaatgg | 660 |
| ccgaagcagg | aaatctggac | ccatcccatc | ggaatgtttt | tcaatgcgtc | acgacggctt | 720 |
| cttactgtcc | tgcgccaaca | agcgcaggcc | gactgccatc | aaggcacact | agacgaatgt | 780 |
| ttacggacca | agaacctctt | tacggcagta | cactgttaca | tattgaatgt | gcggattttg | 840 |
| accgccttat | cggagttgct | cctgtcgcaa | attaggcgga | cccagaacag | ccatatgagc | 900 |
| ccactggaag | ggagtcgatc | ccagtcgccg | agcagagacg | acaccagcag | cagcagcggc | 960 |
| cacagcagtg | ttgacaccat | accttctctt | agcgagaacc | tccctattgg | tgagctgttc | 1020 |
| tcctatgttg | accccctgac | acacgcccta | ttctcggctt | gcactacgtt | acatgttggg | 1080 |
| gtacaattgc | tgcgtgagaa | tgagattact | ctgggagtac | actccgccca | gggcattgca | 1140 |
| gcttccatca | gcatgagcgg | ggaaccaggc | gaggatatag | ccaggacagg | ggcgaccaat | 1200 |
| tccgcaagat | gcgaggagca | gccgaccact | ccagcggctc | gggttttgtt | catgttcttg | 1260 |
| agtgatgaag | gggcttttcca | ggaggcaaag | tctgctggtt | cccgaggtcg | aaccatcgca | 1320 |
| gcactgcgac | gatgctatga | ggatatcttt | tccctcgccc | gcaaacacaa | acatggcatg | 1380 |
| ctcagagacc | tcaacaatat | tcctccatga | | | | 1410 |

<210> SEQ ID NO 111
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 111

| | | | | | |
|---|---|---|---|---|---|
| atggctgcag | atcaaggtat | attcacgaac | tcggtcactc | tctcgccagt | ggagggttca | 60 |
| cgcaccggtg | gaacattacc | ccgccgtgca | ttccgacgct | cttgtgatcg | gtgtcatgca | 120 |
| caaaagatca | aatgtactgg | aaataaggag | gttactggcc | gtgctccctg | tcagcgttgc | 180 |
| cagcaggctg | gacttcgatg | cgtctacagt | gagcgatgcc | ccaagcacaa | gctacgccaa | 240 |
| tccagggcag | cggatctcgt | ctctgctgac | ccagatccct | gcttgcgcat | gtcctcgcct | 300 |
| ccagtgccct | cacagagctt | gccgctagac | gtatccgagt | cgcattcctc | aaatacctcc | 360 |

-continued

```
cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggtacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat accctt cttt agcgagaacc tccctattgg tgagctgttc   1020
tcctatgttg accccctgac acgcccta ttctcggctt gcactacgtt acatgttggg    1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggctttcca ggaggcaaag tctgctggtt cccgaggtcg aaccatcgca   1320
gcactgcgac gatgctatga ggatatcttt ccctcgccc gcaaacacaa acatggcatg   1380
ttcagagacc tcaacaatat tcctccatga                                    1410
```

<210> SEQ ID NO 112
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 112

```
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt ctctgctgac ccagatccct gcttgcacat gtcctcgcct    300
ccagtgccct cacagagctt gccgctagac gtatccgagt cgcattcctc aaataccctcc    360 cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagaga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct ccgtcgcaa attaggcgga cccagaacag ccatatgagc    900
ccactggaag ggagtcgatc ccagtcgccg agcaaagacg acaccagcag cagcagcggc    960
cacagcagtg ttgacacgat accctt cttt agcgagaacc tccctattgg tgagctgttc   1020
```

```
tcctatgttg acccoctgac acacgcccta ttctcggctt gcactacgtt acatgttggg    1080
gtacaattgc tgcgtgagaa tgagattact ctgggagtac actccgccca gggcattgca    1140
gcttccatca gcatgagcgg ggaaccaggc gaggatatag ccaggacagg ggcgaccaat    1200
tccgcaagat gcgaggagca gccgaccact ccagcggctc gggttttgtt catgttcttg    1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg    1380
ctcagagacc tcaacaatat tcctccatga                                     1410
```

<210> SEQ ID NO 113
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 113

```
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg tgtctacagt gagcgatgcc ccaagcgcaa gctacgccaa    240
tccagggcag cggatctcgt ctctgctgac ccagatccct gcttgcacat gtcctcgcct    300
ccagtgccct cacagagctt gccgctagac gtacccgagt cgcattcctc aaatacctcc    360
cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcga cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacgcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat accttctttt agcgagaacc tccctattgg tgagctgttc   1020
tcctatgttg acccccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact cctgcggctc gggttttgtt catgttcttg   1260
agtgatgaag gggcttttcca ggaggcaaag tctgctggtt cccgaggtcg aaccatcgca  1320
gcactgcgac gatgctatga ggatatcttt tccctcgccc gcaaacacaa acatggcatg   1380
ctcagagacc tcaacaatat tcctccatga                                    1410
```

<210> SEQ ID NO 114
<211> LENGTH: 1101
<212> TYPE: DNA
<213> ORGANISM: Artificial Sequence
<220> FEATURE:

<223> OTHER INFORMATION: synthetically generated variant

<400> SEQUENCE: 114

```
atggctgcag atcaaggtat attcacgaac tcggtcactc tctcgccact ggagggttca      60
cgcaccggtg aacattacc ccgccgtgca ttccgacgct cttgtgatcg gtgtcttgca     120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccaggcag cggatctcgt ctctgctgac ccagatccct gcttgcacat gtcctcgcct     300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctggggctg tcccaatgtg atggaggctt cagctgtcag     480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactccgccc agggcattgc agcttccatc    840
agcatgagcg gggaaccagg cgaggatata gccaggacag gggcgaccaa ttccgcaaga    900
tgcgaggagc agccgaccac tccagcggct cgggttttgt tcatgttctt gagtgatgaa    960
ggggctttcc aggaggcaaa gtctgctggt tcccgaggtc gaaccatcgc agcactgcga   1020
cgatgctatg aggatatctt ttccctcgcc cgcaaacaca acatggcat gctcagagac    1080
ctcaacaata atcctccatg a                                             1101
```

<210> SEQ ID NO 115
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 115

```
ttaccgctag catggatctc g                                              21
```

<210> SEQ ID NO 116
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 116

```
tcttgtgcaa tgtaacatca g                                              21
```

<210> SEQ ID NO 117
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 117

```
gagctgtatc tggaagagg                                                 19
```

-continued

```
<210> SEQ ID NO 118
<211> LENGTH: 18
<212> TYPE: DNA
<213> ORGANISM: Artificial Sequence
<220> FEATURE:
<223> OTHER INFORMATION: synthetically generated oligonucleotide

<400> SEQUENCE: 118
cgtccatctc tctccgta                                                 18
```

LOVE VARIANT REGULATOR MOLECULES

RELATED APPLICATION INFORMATION

This application is a continuation-in-part of International Application PCT/US02/32248, filed Oct. 9, 2002, which claims priority from U.S. application Ser. No. 09/974,760, filed Oct. 9, 2001 and U.S. provisional application Ser. No. 60/328,339, filed Oct. 9, 2001, all of which are hereby incorporated by reference.

FIELD OF THE INVENTION

The invention relates to the fields of microbiology and molecular biology. In particular, the invention relates to the field of mycology and the production of secondary metabolites from fungi.

SUMMARY OF THE RELATED ART

Secondary metabolites are a major source of commercially useful products such as food additives, vitamins, and medicines for the treatment of a wide variety of infections and diseases. By way of example, in 1997 the statin drugs lovastatin, simvastatin, and pravastatin, fungal secondary metabolites used in the treatment of hypercholesteremia, together had US sales of US$7.53 billion (Sutherland et al., *Current Opinion In Drug Discovery & Development* 4:229–236 (2001)). The cost and availability of these plant, bacterial and fungal metabolites are frequently determined by limitations imposed on production and purification of these compounds from culture. This problem is frequently exacerbated by the fact that these products are generally produced during the stationary phase of bacterial and fungal growth.

A wide variety of methods have been utilized to increase the amount of secondary metabolite produced in culture. Studies have demonstrated the importance of carefully designing the medium in which a fungus is grown to maximize the amount of a secondary metabolite produced (see, e.g., Hajjaj H, et al., *Appl. Environ. Microbiol.* 67:2596–602 (2001); Lesova, K., et al., *J. Basic Microbiol.* 40:369–75 (2000)). In addition, the method of culture or fermentation also impacts directly on the amount of secondary metabolite produced. For example, see Robinson, T., et al. (*Appl. Microbiol. Biotechnol.* 55:284–289 (2001)), which demonstrates the advantages of solid state (substrate) fermentation.

In addition to the manipulation of culture and media conditions, genetic approaches have been taken to increase secondary metabolite production. For example, the production of penicillin is limited by the activity of two enzymes, encoded by the ipnA and acvA genes, both of which are regulated by the pacC protein, a zinc-finger transcription factor. Naturally occurring mutant alleles of the pacC locus are known to possess more transcription-activating activity than the cognate, wild-type allele (see, e.g., Tilburn et al. *EMBO J.* 14(4):779–790 (1995)). Thus, one genetic approach to increasing secondary metabolite production is to identify and isolate naturally occurring mutant alleles, the expression of which leads to increased secondary metabolite production.

Although many regulators of secondary metabolite production in many organisms are known, not all of the organisms that produce secondary metabolites are amenable to genetic or molecular genetic manipulation. Thus, these systems are not generally useful as a source for the isolation of naturally occurring mutant alleles and are even less useful for the deliberate manipulation of secondary metabolite regulator protein structure with the aim of creating improved regulators of secondary metabolite production.

It would be advantageous to have improved regulators of the biosynthetic enzymes responsible for secondary metabolite production. For example, recent studies suggest increasing usage of statin drugs, e.g., see Waters D. D., *Am. J. Cardiol.* 88: 10F–5F (2001)). Thus, demand for statin drugs is likely to increase substantially. In order to meet the demand for these and other secondary metabolites, new and improved methods for the production of secondary metabolites must be identified.

BRIEF SUMMARY OF THE INVENTION

The invention provides variant secondary metabolite regulator proteins that enable increased production of secondary metabolites. The invention also provides methods to make these improved regulator proteins. Certain of the variant secondary metabolite regulator proteins have increased ability to stimulate production of secondary metabolites in at least some strains of certain fungal species, e.g., certain strains of *Aspergillus terreus* or *Saccharomyces cerevisiae*.

In a first aspect, the invention provides a variant regulator protein of secondary metabolite production with the same greater activity than that of the cognate, wild-type protein in at least some fungal strains. In certain embodiments of this aspect of the invention, the regulator protein is a fungal regulator protein.

In an embodiment of the first aspect, the invention provides an improved regulator protein comprising an amino acid sequence coding for a variant lovE protein having at least one specific mutation that gives rise to greater transcription-activating properties of the regulator protein and/ or induction of secondary metabolite synthesis in at least some fungal strains.

By way of non-limiting example, certain preferred regulator proteins of this aspect of the invention include at least one of the following mutations (amino acid changes), e.g., in a polypeptide comprising the amino acid sequence of SEQ ID NO:91): (1) a Group 6 amino acid residue (e.g., F) mutated to a Group 2 amino acid residue at position 31, in one embodiment the mutation represented by F31L; (2) a Group 3 amino acid residue (e.g., Q) mutated to a Group 5 amino acid residue at position 41, in one embodiment the mutation represented by Q41K or Q41R; (3) a Group 4 amino acid residue (e.g., T) mutated to a Group 2 amino acid residue at position 52, in one embodiment the mutation represented by T52I; (4) a Group 4 amino acid residue (e.g., T) mutated to a Group 3 amino acid residue at position 52, in one embodiment the mutation represented by T52N; (5) a Group 4 amino acid residue (e.g., C) mutated to a Group 5 amino acid residue at position 73, in one embodiment the mutation represented by C73R; (6) a Group 1 amino acid residue (e.g., P) mutated to a Group 4 amino acid residue at position 101, in one embodiment the mutation represented by P101S; (7) a Group 1 amino acid residue mutated to a Group 3 amino acid residue (e.g., P) at position 101, in one embodiment the mutation represented by P101Q; (8) a valine amino acid residue mutated to another Group 2 amino acid residue at position 111, in one embodiment the mutation represented by V111I; (9) a Group 4 amino acid residue (e.g., S) mutated to a Group 2 amino acid residue at position 133, in one embodiment the mutation represented by S133L; (10) a Group 3 amino acid residue (e.g., E) mutated to a Group 2 amino acid residue at position 141, in one embodiment the mutation represented by E141V; (11) a Group 3 amino acid residue (e.g., E) mutated to a Group 5 amino acid residue at position 141, in one embodiment the mutation represented by E141K; (12) a Group 4 amino acid residue (e.g., C) mutated to Group 6 amino acid residue at position 153, in one embodiment the mutation represented by C153Y; (13) a Group 4 amino acid residue (e.g., C) mutated to a Group 5 amino acid residue at position 153, in one embodiment the mutation represented by C153R; (14) a Group 4 amino acid residue (e.g., T) mutated to a Group 1 amino acid residue at position 281, in one embodiment the mutation represented by T281A; (15) a Group 3 amino acid residue (e.g., N) mutated to a Group 2 amino acid residue at position 367, in one embodiment the mutation represented by N367I; (16) a Group 3 amino acid residue (e.g., N) mutated to a Group 6 amino acid residue at position 367, in one embodiment the mutation represented by N367Y; (17) a Group 1 amino acid residue (e.g., P) mutated to Group 4 amino acid residue at position 389, in one embodiment the mutation represented by P389S; (18) a Group 1 amino acid residue (e.g., P) mutated to a Group 2 amino acid residue at position 389, in one embodiment the mutation represented by P389L; (19) a Group 2 amino acid (e.g., V) mutated to a Group 2 amino acid other than V at position 17, in one embodiment the mutation represented by V17L; (20) a Group 5 amino acid (e.g., H) mutated to a Group 5 amino acid residue other than H at position 39, in one embodiment the mutation represented by H39L; (21) a Group 1 amino acid residue (e.g., A) mutated to a Group 4 amino acid residue at position 40, in one embodiment the mutation represented by A40T; (22) a Group 5 amino acid residue (e.g., R) mutated to a Group 5 amino acid residue other than R at position 76, in one embodiment the mutation represented by R76H; (23) a Group 5 amino acid residue (e.g., H) mutated to a Group 5 amino acid residue other than H at position 96, in one embodiment the mutation represented by H96R; (24) a Group 4 amino acid residue (e.g., S) mutated to a Group 1 amino acid residue at position 112, in one embodiment the mutation represented by S112P; (25) a Group 4 amino acid residue (e.g., T) mutated to a Group 2 amino acid residue at position 119, in one embodiment the mutation represented by T119I; (26) a Group 1 amino acid (e.g., P) mutated to a Group 2 amino acid residue at position 183, in one embodiment the mutation represented by P183L; (27) a Group 4 amino acid residue (e.g., S) mutated to a Group 3 amino acid residue at position 186, in one embodiment the mutation represented by S186R; (28) a Group 1 amino acid residue (e.g., A) mutated to a Group 4 amino acid residue at position 204, in one embodiment the mutation represented by A204T; (29) a deletion of amino acids residues 271–373; (30) a Group 2 amino acid residue (e.g., I) mutated to a Group 2 amino acid residue other than Ile at position 283, in one embodiment the mutation represented by I283L; (31) a Group 2 amino acid residue (e.g., L) mutated to a Group 3 amino acid residue at position 288, in one embodiment the mutation represented by L288Q; (32) a Group 2 amino acid residue (e.g., M) mutated to a Group 2 amino acid residue other than Met at position 299, in one embodiment the mutation represented by M299I; (33) a Group 3 amino acid residue (e.g., E) mutated to a Group 2 amino acid residue at position 303, in one embodiment the mutation represented by E303V; (34) a Group 5 amino acid residue (e.g., R) mutated to a Group 5 amino acid residue other than Arg at position 312, in one embodiment the mutation represented by R312K; (35) a Group 2 amino acid residue (e.g., D) mutated to a Group 2 amino acid residue other than Asp at position 314, in one embodiment the mutation represented by D314E; (36) a deletion of Ser at position 316, 317, 318, or 319; (37) a Group 4 amino acid residue (e.g., T) mutated to a Group 5 amino acid residue at position 396, in one embodiment the mutation represented by T396K; (38) a Group 2 amino acid residue (e.g., M) mutated to a Group 2 amino acid residue other than Met at position 418, in one embodiment the mutation represented by M418L; (39) a Group 4 amino acid residue (e.g., S) mutated to a Group 4 amino acid residue other than Ser at position 421, in one embodiment the mutation represented by S421T; (40) a Group 2 amino acid residue (e.g., L) mutated to a Group 6 amino acid residue at position 461, in one embodiment the mutation represented by L461F; and (41) a Group 2 amino acid residue (e.g., I) mutated to a Group 3 amino acid residue at position 467, in one embodiment the mutation represented by I467N.

In some embodiments of the first aspect, the invention provides regulator proteins with at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen of the above described specific mutations.

In other embodiments of the first aspect, the invention provides an isolated lovE variant regulator protein or a polypeptide comprising, consisting of or consisting essentially of an amino acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:91, SEQ ID NO:93, SEQ ID NO:94, SEQ ID NO:97, SEQ ID NO:98, SEQ ID NO:99, SEQ ID NO:100, SEQ ID NO:101, SEQ ID NO:102, SEQ ID NO:103, SEQ ID NO:104, and SEQ ID NO:105.

In other embodiments of the first aspect, the invention provides an isolated lovE variant regulator protein or a polypeptide comprising, consisting of or consisting essentially of an amino acid sequence selected from the group consisting of: SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:91, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, with the addition of the amino acid sequence of SEQ ID NO:95 or SEQ ID NO:96 at the amino terminus.

In a second aspect, the invention provides a nucleic acid molecule encoding a lovE regulator of the first aspect of the invention. By way of non-limiting example, the invention provides a nucleic acid molecule encoding the lovE variant regulator protein or a polypeptide comprising, consisting or consisting essentially of an amino acid sequence selected from the group consisting of SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:78, SEQ ID NO:79, SEQ ID NO:81, SEQ ID NO:82, SEQ ID NO:83, SEQ ID NO:84, SEQ ID NO:86, SEQ ID NO:87, SEQ ID NO:88, SEQ ID NO:89, SEQ ID NO:90, SEQ ID NO:91, SEQ ID NO:93, SEQ ID NO:94, SEQ ID NO:97, SEQ ID NO:98, SEQ ID NO:99, SEQ ID NO:100, SEQ ID NO:101, SEQ ID NO:102, SEQ ID NO:103, SEQ ID NO:104, and SEQ ID NO:105. In certain embodiments the polypeptide comprises the amino acid sequence of SEQ ID NO:95 or SEQ ID NO:96 at its amino terminus. In a preferred embodiment of the second aspect, the nucleic acid molecule lacks introns that interrupt the polypeptide coding sequence. Thus, the nucleotide sequence encoding the polypeptide is contiguous.

In a third aspect, the invention provides a method of increasing the activity of a protein that regulates secondary metabolite production comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; and (c) selecting a variant regulator protein with more activity than the cognate, wild-type protein.

In various embodiments of the third aspect, the secondary metabolite is a fungal secondary metabolite. In certain embodiments of the third aspect, the protein regulator of secondary metabolite production is a transcription factor. In certain embodiments of the third aspect, the protein regulator of secondary metabolite production is a transmembrane transporter, protein that mediates secretion, kinase, G-protein, cell surface receptor, GTPase activating protein, guanine nucleotide exchange factor, phosphatase, protease, phosphodiesterase, bacterial protein toxin, importin, RNA-binding protein, SCF complex component, adherin, or protein encoded within a biosynthetic cluster. In certain other embodiments of the third aspect, the variant regulator protein is selected to have more activity in a heterologous cell and/or more activity in a homologous cell than the cognate, wild-type regulator protein. In certain embodiments, the variant regulator protein is selected to have more activity in a heterologous cell and/or more activity in a homologous cell than the cognate, wild-type protein and to cause more secondary metabolite to be produced in a homologous cell and/or a heterologous cell when compared to the cognate, wild-type regulator protein. In a particularly preferred embodiment, the variant regulator protein is a lovE variant regulator protein.

In a fourth aspect, the invention provides a method of increasing production of a secondary metabolite comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) expressing the selected variant regulator protein in a cell, thereby increasing production of the secondary metabolite in the cell.

In various embodiments of the fourth aspect, the secondary metabolite is a fungal secondary metabolite. In certain embodiments of the third aspect, the protein regulator of secondary metabolite production is a transcription factor. In certain embodiments of the fourth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain other embodiments of the fourth aspect, the variant regulator protein is selected to have more activity in a heterologous cell and/or more activity in a homologous cell. In certain embodiments, the variant regulator protein is selected to have more activity in a heterologous cell and/or more activity in a homologous cell and to cause more secondary metabolite to be produced in a homologous cell and/or a heterologous cell when compared to the cognate, wild-type regulator protein. In a particularly preferred embodiment, the valiant regulator protein is a lovE variant regulator protein.

In a fifth aspect, the invention provides an isolated variant regulator protein of secondary metabolite production having increased activity compared to a cognate, wild-type protein, the variant regulator protein made by the process comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) recovering the selected variant regulator protein.

In certain embodiments of the fifth aspect, the secondary metabolite is a fungal secondary metabolite. In certain embodiments of the fifth aspect, the protein regulator of secondary metabolite production is a transcription factor. In certain embodiments of the fifth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster.

In certain embodiments of the fifth aspect, the variant regulator protein has more activity in a heterologous and/or a homologous cell than the cognate, wild-type protein in at least some fungal strains, e.g., in at least some strains of A. terreus. In certain embodiments of the fourth aspect, the variant regulator protein increases production of a secondary metabolite in a heterologous cell and/or a homologous cell when compared to the cognate, wild-type protein. In a particularly preferred embodiment, the variant regulator protein is a lovE variant regulator protein.

In a sixth aspect, the invention provides a fungus having improved lovastatin production made by the process of transforming a fungal cell with a nucleic acid molecule encoding a lovE variant protein of the first aspect of the invention. In an embodiment thereof, the nucleic acid molecule is selected from a nucleic acid molecule of the second aspect of the invention.

In a seventh aspect, the invention provides an improved process for making lovastatin comprising transforming a fungal cell with a nucleic acid molecule encoding a variant of the lovE protein of the first aspect of the invention. In an embodiment thereof, the fungal cell is transformed with a nucleic acid molecule of the second aspect of the invention.

In an eighth aspect, the invention provides a nucleic acid molecule encoding a lovE protein defined by SEQ ID NO:91. In one embodiment, the nucleic acid molecule comprises a contiguous coding sequence lacking introns encoding a polypeptide comprising SEQ ID NO:91. In an embodiment thereof, the invention provides an isolated lovE nucleic acid molecule defined by SEQ ID NO:92. In an eighth aspect, the invention provides a nucleic acid molecule encoding a lovE protein defined by SEQ ID NO:91. In an embodiment thereof, the invention provides an isolated lovE nucleic acid molecule defined by SEQ ID NO:92.

In a ninth aspect the invention features an isolated polypeptide comprising, consisting of, or consisting essentially of the amino acid sequence of SEQ ID NO:91 having an amino acid change selected from the group consisting of: (a) a Phe changed to a Group 2 amino acid residue at position 31; (b) a Gln changed to a Group 5 amino acid residue at position 41; (c) a Thr changed to a Group 2 amino acid residue at position 52; (d) a Thr changed to a Group 3 amino acid residue at position 52; (e) a Cys changed to a Group 5 amino acid residue at position 73; (f) a Pro changed to a Group 4 amino acid residue at position 101; (g) a Pro changed to a Group 3 amino acid residue at position 101; (h) a Val changed to a Group 2 amino acid residue other than Val at position 111; (i) a Ser changed to a Group 2 amino acid residue at position 133; (j) a Glu changed to a Group 2 amino acid residue at position 141; (k) a Glu changed to a Group 5 amino acid residue at position 141; (l) a Cys changed to a Group 6 amino acid residue at position 153; (m) a Cys changed to a Group 5 amino acid residue at position 153; (n) a Thr changed to a Group 1 amino acid residue at position 281; (o) a Asn changed to a Group 2 amino acid residue at position 367; (p) a Asn changed to a Group 6 amino acid residue at position 367; (q) a Pro changed to a Group 4 amino acid residue at position 389; (r) a Pro changed to a Group 2 amino acid residue at position 389; (s) a Val changed to a Group 2 amino acid residue other than Val at position 17; (t) a His changed to a Group 5 amino acid residue other than His at position 39; (u) an Ala changed to a Group 4 amino acid residue at position 40; (v) an Arg changed to a Group 5 amino acid residue other than Arg at position 76; (w) a His changed to a Group 5 amino acid residue other than His at position 96; (x) a Ser changed to a Group 1 amino acid residue at position 112; (y) a Thr changed to a Group 2 amino acid residue at position 119; (z) a Pro changed to a Group 2 amino acid residue at position 183; (aa) an Ser changed to a Group 3 amino acid residue at position 186; (bb) an Ala changed to a Group 4 amino acid residue at position 204; (cc) a deletion of amino acids residues 271–373; (dd) an Ile changed to a Group 2 amino acid residue other than Ile at position 283; (ee) a Leu changed to a Group 3 amino acid residue at position 288; (ff) a Met changed to a Group 2 amino acid residue other than Met at position 299; (gg) a Glu changed to a Group 2 amino acid residue at position 303; (hh) an Arg changed to a Group 5 amino acid residue other than Arg at position 312; (ii) an Asp changed to a Group 2 amino acid residue other than Asp at position 314; (jj) a deletion of Ser at position 316, 317, 318, or 319; (kk) a Thr changed to a Group 5 amino acid residue at position 396; (ll) a Met changed to a Group 2 amino acid residue other than Met at position 418; (mm) a Ser changed to a Group 4 amino acid residue other than Ser at position 421; (nn) a Leu changed to a Group 6 amino acid residue at position 461; and (oo) an Ile changed to a Group 3 amino acid residue at position 467.

In various embodiments of the ninth aspect: the polypeptide when expressed in an *A. terreus* cell harboring a lovF gene increases expression of the lovF gene relative to an otherwise identical cell not expressing the polypeptide; the polypeptide when expressed in an *S. cerevisiae* harboring a lovF gene under the control of the *A. terreus* lovF expression control region increases expression of the gene relative to an otherwise identical cell not expressing the polypeptide; the polypeptide has fewer than 15, fewer than 11, fewer than 10, fewer than 8, fewer than 5, fewer than 3, or one amino acid change; the polypeptide further comprises the amino acid sequence of SEQ ID NO:95 immediately amino terminal to the amino acid of SEQ ID NO:91; the polypeptide further comprises the amino acid sequence of SEQ ID NO:96 immediately amino terminal to the amino acid of SEQ ID NO:91; the isolated polypeptide has the amino acid change F31L, Q41K, Q41R, T52N, C73R, P101S, P101Q, V111I, S133L, E141V, E141K, C153Y, C153R, T281A, N367I, N367Y, P389S, P389L, V17L, H39L, A40T, R76H, H96R, S112P, T119I, P183L, S186R, A204T, the deletion of amino acids 271–373, I283L, L288Q, M299I, E303V, R312K, D314E, the deletion of S316, S317, S318, or S319, T396K, M418L, S421T, L461F, or I467N; and the isolated polypeptide comprises, consists of or consists essentially of an amino acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:91, SEQ ID NO:93, SEQ ID NO:94, SEQ ID NO:97, SEQ ID NO:98, SEQ ID NO:99, SEQ ID NO:100, SEQ ID NO:101, SEQ ID NO:102, SEQ ID NO:103, SEQ ID NO:104, and SEQ ID NO:105.

In a tenth aspect the invention features an isolated nucleic acid molecule comprising a nucleotide sequence encoding a polypeptide comprising the amino acid sequence of SEQ ID NO:91 having at least one amino acid change selected from the group consisting of: (a) a Phe changed to a Group 2 amino acid residue at position 31; (b) a Gln changed to a Group 5 amino acid residue at position 41; (c) a Thr changed to a Group 2 amino acid residue at position 52; (d) a Thr changed to a Group 3 amino acid residue at position 52; (e) a Cys changed to a Group 5 amino acid residue at position 73; (f) a Pro changed to a Group 4 amino acid residue at position 101; (g) a Pro changed to a Group 3 amino acid residue at position 101; (h) a Val changed to a Group 2 amino acid residue other than Val at position 111; (i) a Ser changed to a Group 2 amino acid residue at position 133; (j) a Glu changed to a Group 2 amino acid residue at position 141; (k) a Glu changed to a Group 5 amino acid residue at position 141; (l) a Cys changed to a Group 6 amino acid residue at position 153; (m) a Cys changed to a Group 5 amino acid residue at position 153; (n) a Thr changed to a Group 1 amino acid residue at position 281; (o) a Asn changed to a Group 2 amino acid residue at position 367; (p) a Asn changed to a Group 6 amino acid residue at position 367; (q) a Pro changed to a Group 4 amino acid residue at position 389; (r) a Pro changed to a Group 2 amino acid residue at position 389; (s) a Val changed to a Group 2 amino acid residue other than Val at position 17; (t) a His changed to a Group 5 amino acid residue other than His at position 39; (u) an Ala changed to a Group 4 amino acid residue at position 40; (v) an Arg changed to a Group 5 amino acid residue other than Arg at position 76; (w) a His changed to a Group 5 amino acid residue other than His at position 96; (x) a Ser changed to a Group 1 amino acid residue at position 112; (y) a Thr changed to a Group 2 amino acid residue at position 119; (z) a Pro changed to a Group 2 amino acid residue at position 183; (aa) an Ser changed to a Group 3 amino acid residue at position 186; (bb) an Ala changed to a Group 4 amino acid residue at position 204; (cc) a deletion of amino acids residues 271–373; (dd) an Ile changed to a Group 2 amino acid residue other than Ile at position 283; (ee) a Leu changed to a Group 3 amino acid residue at position 288; (ff) a Met changed to a Group 2 amino acid residue other than Met at position 299; (gg) a Glu changed to a Group 2 amino acid residue at position 303; (hh) an Arg changed to a Group 5 amino acid residue other than Arg at position 312; (ii) an Asp changed to a Group 2 amino acid residue other than Asp at position 314; (jj) a deletion of Ser at position 316, 317, 318, or 319; (kk) a Thr changed to a Group 5 amino acid residue at position 396; (ll) a Met changed to a Group 2 amino acid residue other than Met at position 418; (mm) a Ser changed to a Group 4 amino acid residue other than Ser at position 421; (nn) a Leu changed to a Group 6 amino acid residue at position 461; and (oo) an Ile changed to a Group 3 amino acid residue at position 467.

In various embodiments of the tenth aspect: the polypeptide when expressed in an *A. terreus* cell harboring a lovF gene increases expression of the lovF gene relative to an otherwise identical cell not expressing the polypeptide; the polypeptide when expressed in a *S. cerevisiae* harboring a gene under the control of the *A. terreus* lovF expression control region increases expression of the gene relative to an otherwise identical cell not expressing the polypeptide; the polypeptide has fewer than 15, fewer than 11, fewer than 10, fewer than 8, fewer than 5, fewer than 3, or one amino acid change; the polypeptide further comprises the amino acid sequence of SEQ ID NO:95 immediately amino terminal to the amino acid of SEQ ID NO:91; the polypeptide further comprises the amino acid sequence of SEQ ID NO:96 immediately amino terminal to the amino acid of SEQ ID NO:91; the isolated polypeptide has the amino acid change F31L, Q41K, Q41R, T52N, C73R, P101S, P101Q, V111I, S133L, E141V, E141K, C153Y, C153R, T281A, N367I, N367Y, P389S, P389L, V17L, H39L, A40T, R76H, H96R, S112P, T119I, P183L, S186R, A204T, a deletion of amino acids 271–373, I283L, L288Q, M299I, E303V, R312K, D314E, a deletion of S316, S317, S318, or S319, T396K, M418L, S421T, L461F, and I467N; the isolated polypeptide comprises, consists of, or consists essentially of an amino acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:91, SEQ ID NO:93, SEQ ID NO:94, SEQ ID NO:97, SEQ ID NO:98, SEQ ID NO:99, SEQ ID NO:100, SEQ ID NO:101, SEQ ID NO:102, SEQ ID NO:103, SEQ ID NO:104, and SEQ ID NO:105; and the isolated nucleic acid molecule comprises, consists of, or consists essentially of a nucleotide sequence selected from the group consisting of: SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:106, SEQ ID NO:107, SEQ ID NO:108, SEQ ID NO:109, SEQ ID NO:110, SEQ ID NO:111, SEQ ID NO:112, SEQ ID NO:113, and SEQ ID NO:114. In other embodiments of the tenth aspect, the nucleotide sequence encoding the polypeptide is contiguous, i.e., the coding sequence is not interrupted by an intron.

In an eleventh aspect, the invention features a fungal cell containing a nucleic acid molecule encoding any of the forgoing polypeptides.

In a twelfth aspect, the invention features a fungal cell (e.g., an *A. terreus* cell) containing any of the forgoing nucleic acid molecules of any of claims 1–96.

In a thirteen aspect, the invention features a method for providing a fungal cell having improved production of a secondary metabolite (e.g., lovastatin), the method comprising transforming the fungal cell with a nucleic acid molecule described above whereby the fungal cell has increased secondary metabolite production compared to an otherwise identical fungal cell that has not been so transformed.

In a fourteenth aspect, the invention features a method for producing a secondary metabolite (e.g., lovastatin), the method comprising providing a fungal cell containing a forgoing nucleic acid molecule, culturing the cell under conditions so as to produce the secondary metabolite, and isolating from the cells a fraction containing the secondary metabolite.

In a fifteenth aspect, the invention features an isolated polypeptide comprising, consisting of, or consisting essentially of the amino acid sequence of SEQ ID NO:91 having an amino acid change selected from the group consisting of: H253R, S341P, R121W, S322G, A83V, T135I, E177G, E197K, T281A, T256A, N466S, C73R, E303K, Q41K, Q41K, P16A, G23S, T9M, Q362E, R21H, S34A, Q80H, A84S, E303D, H374D, A440T, A441V, C445S, P469S, F31L, T409I, M971, E113D, D146N, P163S, H458Y, I43V, Q295L, F31L, C159S, E162K, R293L, S311N, L141, E18V, G138C, E338G, V361L, N400S, S174Y, A402T, F31L, P108S, D85N, I143F, M232I, T315I, S382Y, M385K, T461, Q62R, K77R, S323C, V373I, T294I, P310L, G337D, A394V, G436S, T139, V184I, D4E, V87I, D110E, A189T, N276D, T347R, N367I, Q377R, A425T, D131N, R312G, A429G, V17L, H39L, A40T, R76H, H96R, S112P, T119I, P183L, S186R, A204T, a deletion of amino acids 271–373, I283L, L288Q, M299I, E303V, R312K, D314E, a deletion of S316, S317, S318, or S319, T396K, M418L, S421T, L461F, and I467N. In other embodiments, the polypeptide includes at least one such amino acid change.

In various embodiments, the invention features a plasmid comprising a lovE variant polypeptide described herein.

In various embodiments of the fifteenth aspect, the invention features the polypeptide, when expressed in an *A. terreus* cell harboring a lovF gene, increases expression of the lovF gene relative to an otherwise identical cell not expressing the polypeptide; the polypeptide when expressed in an *S. cerevisiae* cell harboring a gene under the control of the *A. terreus* lovF expression control region increases expression of the gene relative to an otherwise identical cell not expressing the polypeptide; the polypeptide has fewer than 15, fewer than 11, fewer than 10, fewer than 8, fewer than 5, fewer than 3, or one amino acid change; the polypeptide further comprises the amino acid sequence of SEQ ID NO:95 immediately amino terminal to the amino acid of SEQ ID NO:91; the polypeptide further comprises the amino acid sequence of SEQ ID NO:96 immediately amino terminal to the amino acid of SEQ ID NO:91.

DETAILED DESCRIPTION OF THE PREFERRED EMBODIMENTS

Figure 1:
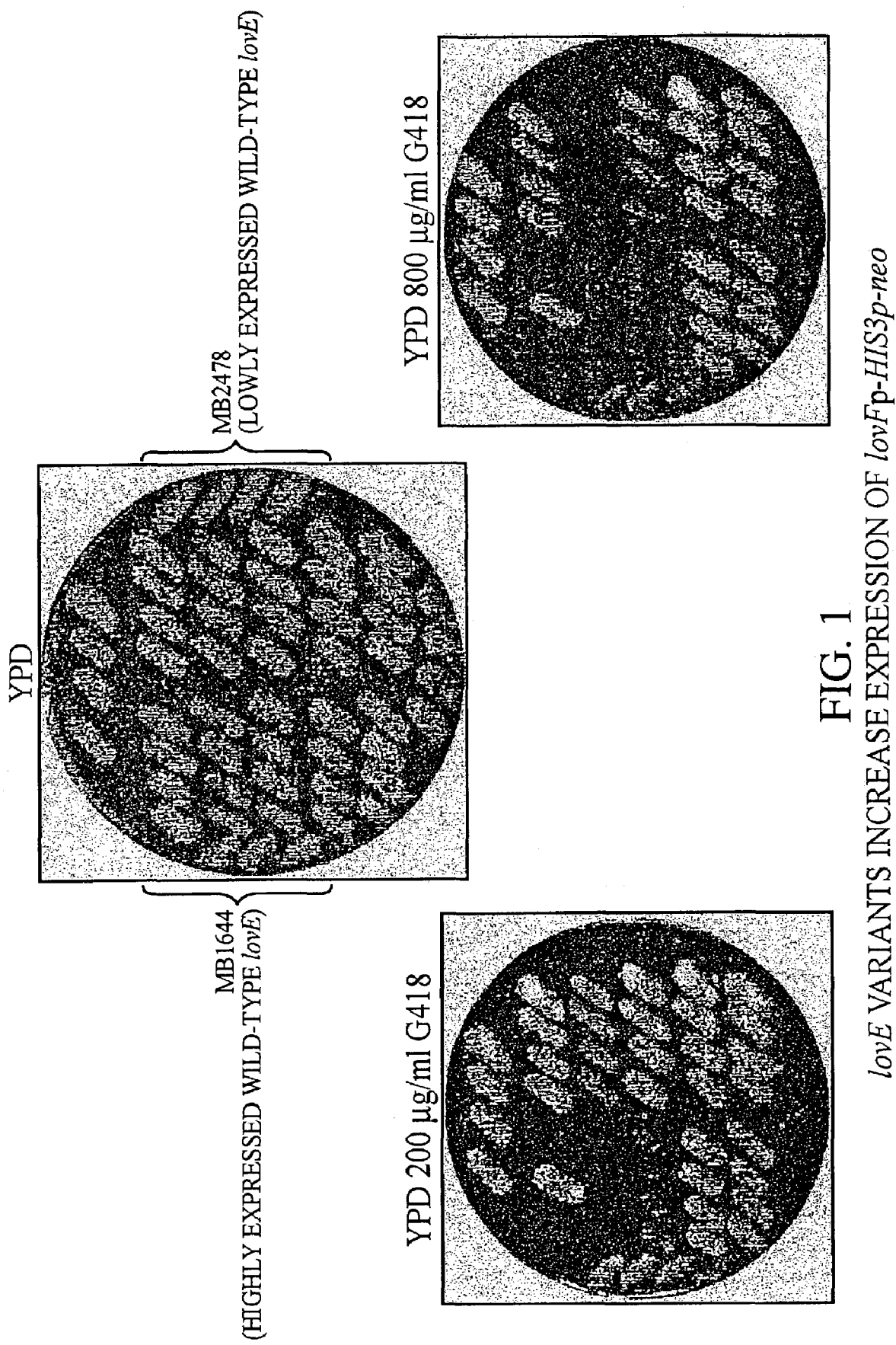
FIG. 1 is a photographic representation of cells growing on media with and without G418 selection demonstrating lovFp-HIS3p-Neo activation in *S. cerevisiae*. Controls include MB968 (vector only), MB2478 (lowly expressed wild-type lovE), and MB1644 (highly expressed wild-type lovE). All lovE variants are expressed in an MB968 vector backbone similar to MB2478.
Figure 2A:
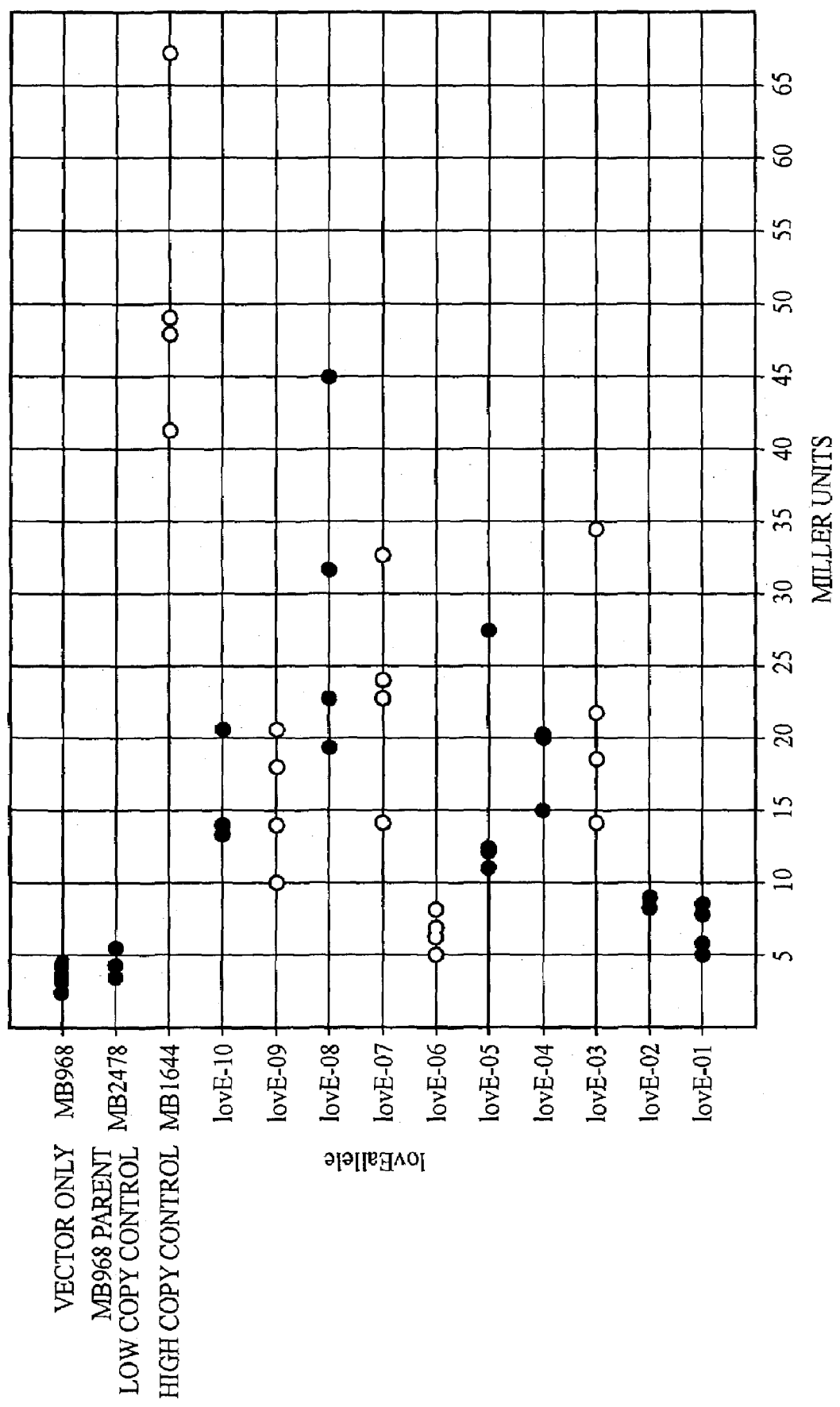
FIG. 2A is a graphic representation of lovFp-CYC1p-lacZ expression in *S. cerevisiae* strains expressing lovE variant proteins from the clones lovE 1–10.
Figure 2B:
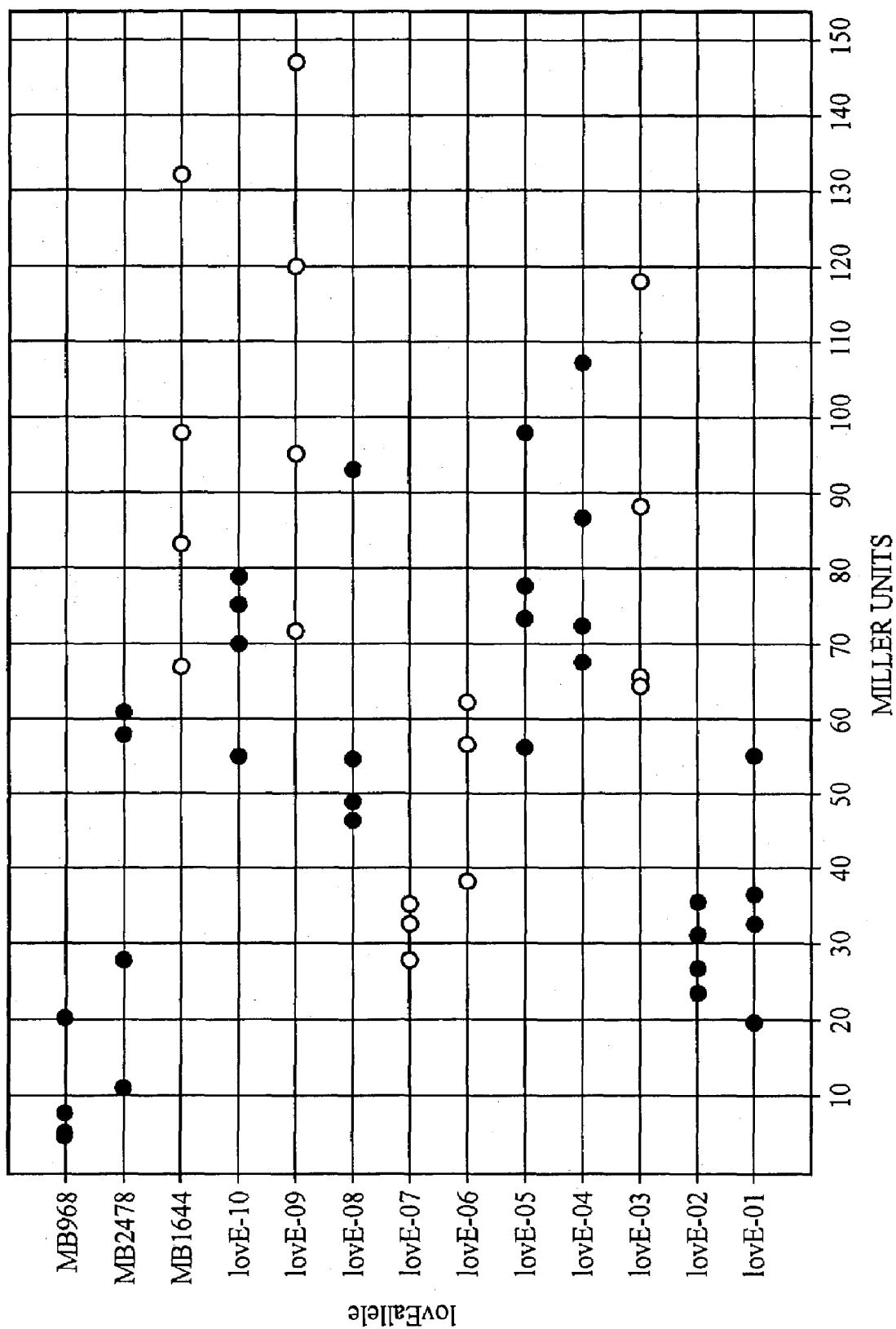
FIG. 2B is a graphic representation of lovFp-CYC1p-lacZ expression in *S. cerevisiae* strains expressing lovE variant proteins from the clones lovE 1–10 from a separate transformation than that of FIG. 2A.
Figure 3:
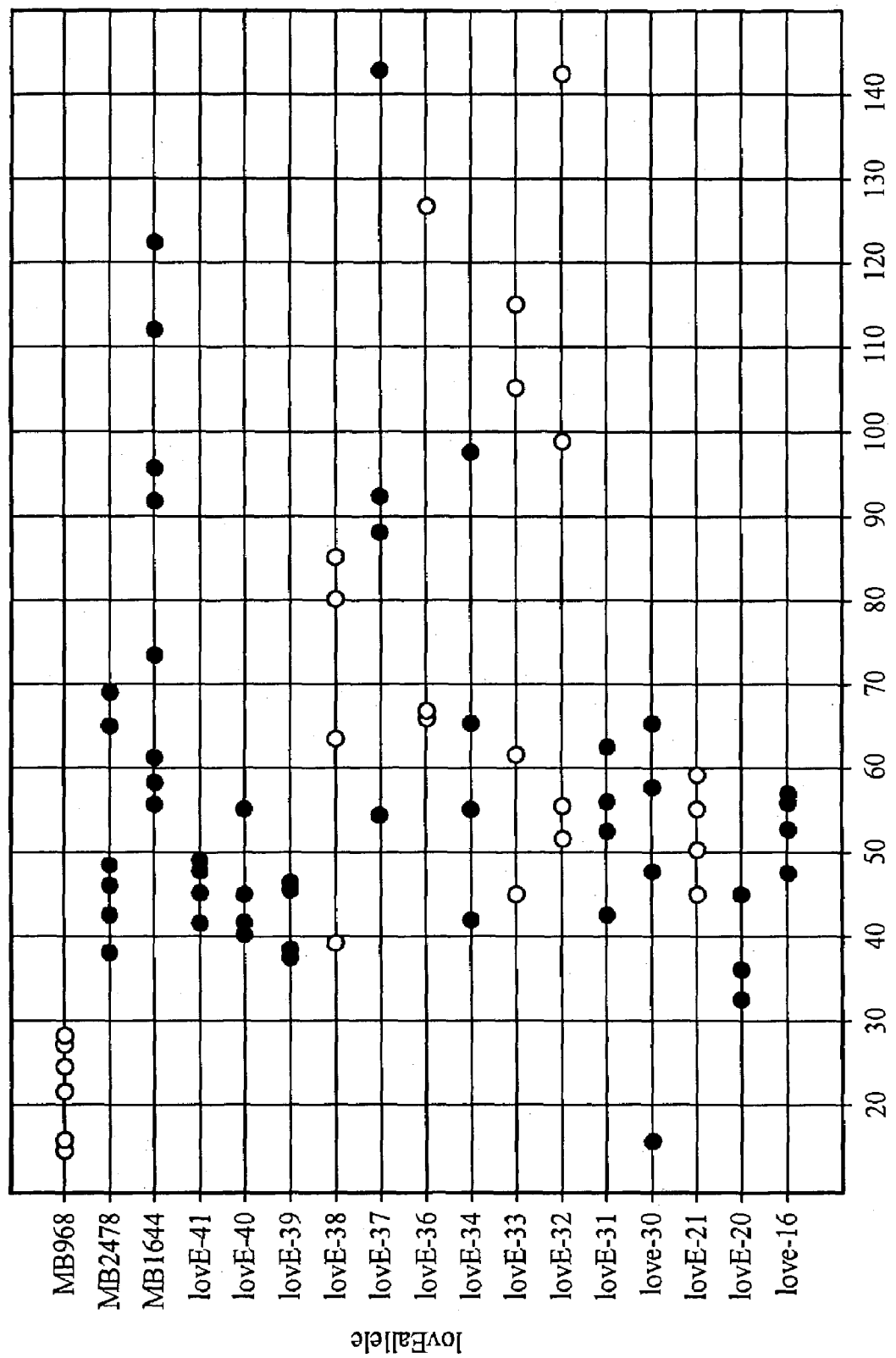
FIG. 3 is a graphic presentation of lovFp-CYC1p-lacZ expression in *S. cerevisiae* strains expressing lovE variant proteins from clones lovE 16–41.
Figure 4:
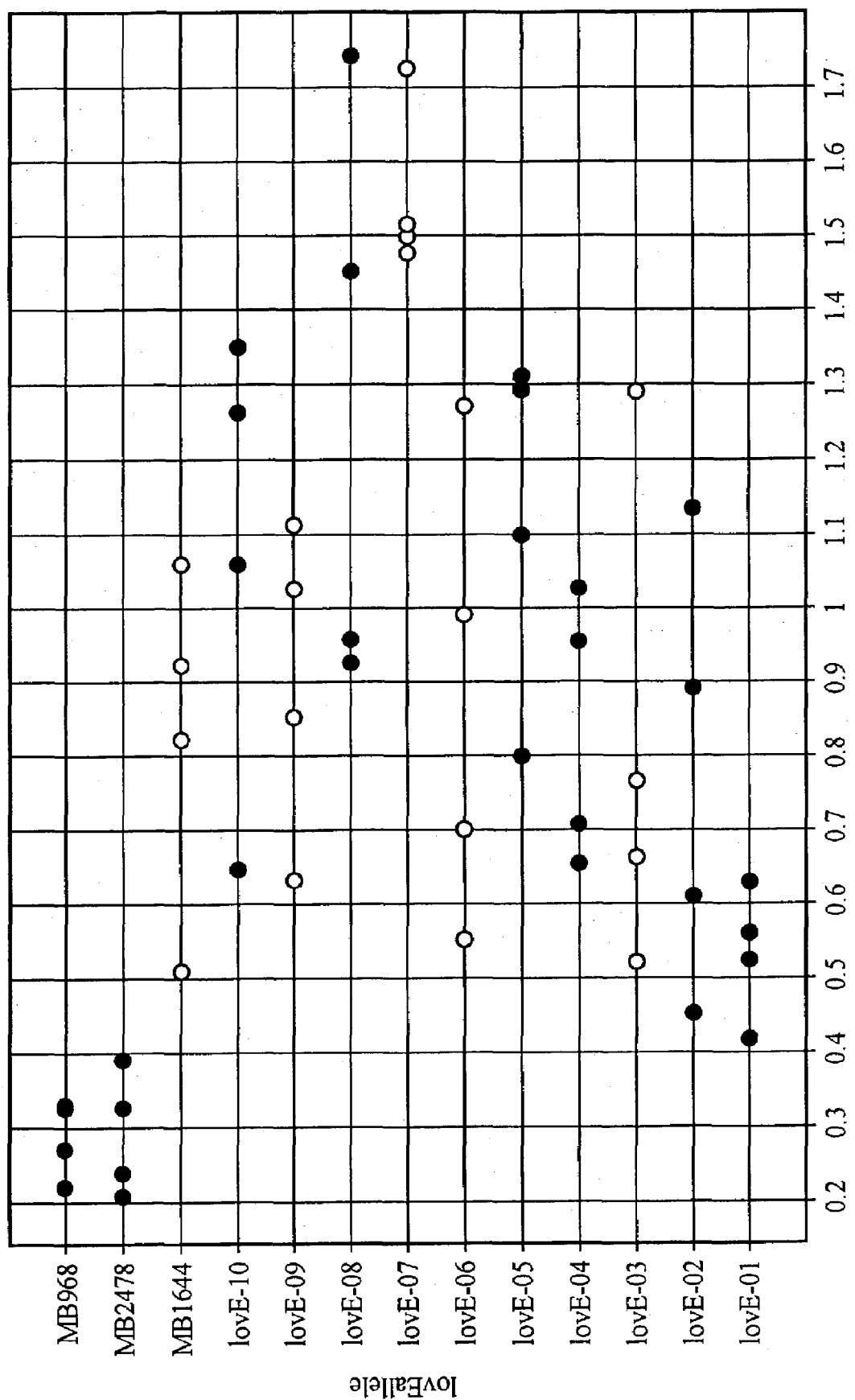
FIG. 4 is a graphic presentation of lovFp-lacZ expression in *S. cerevisiae* strains expressing lovE variant proteins from clones lovE 1–10.
Figure 5:
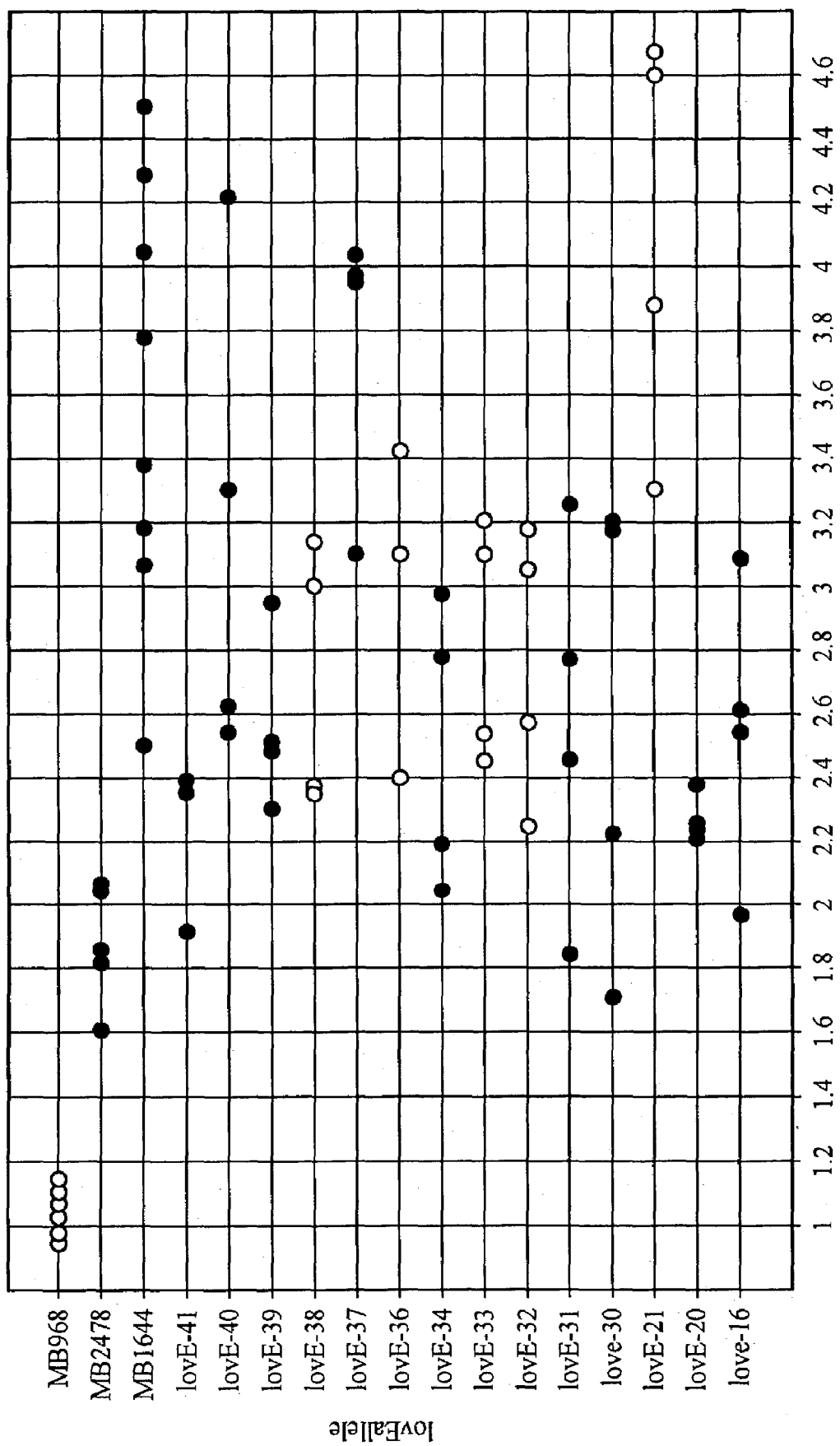
FIG. 5 is a graphic presentation of lovFp-lacZ expression in *S. cerevisiae* strains expressing lovE variant proteins from clones lovE 16, 20, 21, 30–34, and 36–41.

The invention provides variant secondary metabolite regulator proteins that enable production of secondary metabolites. The invention also provides methods to make these variant regulator proteins. Certain of the variant secondary metabolite regulator proteins have increased ability to stimulate production of secondary metabolites in at least some strains of certain fungal species, e.g., certain strains of *Aspergillus terreus* or *Saccharomyces cerevisiae*, compared to the cognate wild-type protein.

In certain embodiments of the aspects of the invention, the invention relates to the biosynthesis and improved production of secondary metabolites. The invention provides variant regulator proteins useful for the production of secondary metabolites, nucleic acid molecules encoding variant regulator proteins, and methods for their production.

As used herein, the terms "fungal" and "fungus" refer generally to eukaryotic, heterotrophic organisms with an absorptive mode of nutrition. Fungi typically contain chitin in their cell walls and exhibit mycelial or yeast-like growth habits (*More Gene Manipulations in Fungi*, edited by J. W. Bennet and L. L. Lasure, Academic Press Inc. (1991), ISBN 0120886421). More specifically, the terms refer to secondary metabolite producing organisms including, without limitation, *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp. and *Phaffia rhodozyma* (See, *Fungal Physiology*, Chapter 9 (Secondary (Special) Metabolism), Griffin, D. H., John Wiley & Sons, Inc.; ISBN: 0471166154).

The term "variant regulator protein" is used herein to refer to any regulatory protein having at least one change or difference in the amino acid sequence of the protein when compared to its cognate, wild-type regulatory protein sequence. The term does not include naturally occurring allelic variations of the cognate, wild-type regulatory protein.

The term "regulator protein" is meant to refer to a protein having a positive or negative function that modifies the production of a secondary metabolite. The function of the protein may be at the level of transcription, e.g., repression or activation, protein synthesis, or transport. The regulator may alter the level of transcription, RNA stability, translation, post-translational modification, or cellular localization of proteins involved in secondary metabolite synthesis and/or transport. The regulator may also have effects on precursor metabolite pools, flux through specific pathways and metabolite resistance.

By way of non-limiting example, certain embodiments of the aspects of the invention relate to a regulator protein that is a protein that contributes and/or promotes transcription of a gene sequence, i.e., a transcription-activating protein. "Transcription-activating" is a term used to refer to characteristics of a protein that promote transcription. As used herein, a transcription-activating protein would include proteins that increase accessibility of the DNA to transcription complexes, for example, by opening or relaxing chromatin structure, proteins that promote the recognition and/or binding of transcription complexes to a target gene sequence, and/or proteins that promote transcription complex movement along the length of the template DNA sequence.

Regulatory proteins of secondary metabolite production and the nucleic acid sequences encoding these are known to those skilled in the art. Non-limiting examples of regulatory proteins of secondary metabolite synthesis include: regulator proteins of the aflatoxin/sterigmatocystin biosynthetic cluster (Woloshuk, C. P., et al., *Appl, Environ. Microbiol.* 60:2408–2414 (1994) and Brown, D. W., et al., *Proc Natl Acad Sci USA*. 93:1418–1422 (1996)); regulator proteins of the paxilline biosynthetic cluster (Young, C., et al., *Mol, Microbiol.* 39:754–764 (2001)); regulator proteins of the cephalosporin and penicillin biosynthetic clusters (Litzka O., et al., *Antonie Van Leeuwenhoek* 75:95–105 (1999); Schmitt E. K. and Kuck U., *J. Biol. Chem.* 275:9348–9357 (2000); MacCabe et al. *Mol. Gen. Genet.* 250:367–374 (1996); Suarez et al. *Mol. Microbiol.* 20:529–540 (1996); Lambert et al. *Mol. Cell. Biol.* 17:3966–3976 (1997); Su et al. *Genetics* 133:67–77 (1993); regulator proteins of trichothecene synthesis (Trapp S. C., et al., *Mol. Gen. Genet.* 257:421–432 (1998); Brown D. W., et al., *Fungal Genet. Biol.* 32:121–133 (2001); and Matsumoto G., et al. *Biosci. Biotechnol. Biochem.* 63:2001–2004 (1999)); and regulator proteins of lovastatin synthesis (Kennedy, J., et al., *Science* 284:1368–1372 (1999); Hendrickson et al., *Chem. Biol.* 6:429–439 (1999) Tag, A. et al., *Mol Microbiol*. 38:658–65 (2000)).

Certain embodiments of the aspects of the invention disclosed herein relate to the lovE regulator protein, a protein which plays a key role in the biosynthesis of lovastatin. More particularly, certain embodiments of the aspects of the invention relate to variant proteins of the lovE regulator protein and methods of making the same. Such proteins are variant with respect to the following *A. terreus* wild-type lovE sequences (SEQ ID NOS:91 and 92).

The patents and publications cited herein reflect the level of knowledge in the art and are hereby incorporated by reference in their entirety. Any conflict between any teaching of such references and this specification shall be resolved in favor of the latter.

The invention utilizes techniques and methods common to the fields of molecular biology, genetics and microbiology. Useful laboratory references for these types of methodologies are readily available to those skilled in the art. See, for example, *Molecular Cloning, A Laboratory Manual*, 3rd edition, edited by Sambrook, J., MacCallum, P., and Russell, D. W. (2001), Cold Spring Harbor Laboratory Press (ISBN: 0-879-69576-5); *Current Protocols In Molecular Biology*, edited by Ausubel, F. M., Brent, R., Kingston, R. E., Moore, D. D., Seidman, J. G., Struhl, K. (1993), John Wiley and Sons, Inc. (ISBN: 0-471-30661-4); *PCR Applications: Protocols for Functional Genomics*, edited by Innis, M. A., Gelfand, D. H., Sninsky, J. J. (1999), Cold Spring Harbor Press (ISBN: 0-123-72186-5); and *Methods In Yeast Genetics*, 2000 Edition: A Cold Spring Habor Laboratory Course Manual, by Burke, D., Dawson, D. and Stearns, T., Cold Spring Harbor Press (ISBN: 0-879-69588-9).

TABLE 1

Amino Acid and Nucleic Acid Sequences of Wild-type lovE

Wild-type lovE Amino Acid Sequence

MAADQGIFTNSVTLSPVEGSRTGGTLPRRAFRRSCDRCHAQKIKCTGNKEVTGRAPCQR (SEQ ID NO:91)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAQGIAASISMSGEPGEDIARTGATNSARCEEQPTTPAA

RVLFMFLSDEGAFQEAKSAGSRGRTIAALRRCYEDIFSLARKHKHGMLRDLNNIPP

Wild-type lovE DNA Sequence (open reading frame only)

ATGGCTGCAGATCAAGGTATATTCACGAACTCGGTCACTCTCTCGCCAGTGGAGGGTTC (SEQ ID NO:92)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAATTTCTTGATCCACCGGACAGCTACGACTGGTCGTGGACCTCGATTGG

CACTGACGAGGCTATTGACACTGACTGCTGGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCATCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCTCCTATGTTGACCCCCTGACACACGCCCTATTCTCGGCTTGC

ACTACGTTACATGTTGGGGTACAATTGCTGCGTGAGAATGAGATTACTCTGGGAGTACA

TABLE 1-continued

Amino Acid and Nucleic Acid Sequences of Wild-type lovE

```
CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA
```

As used herein, the term "secondary metabolite" means a compound, derived from primary metabolites, that is produced by an organism, is not a primary metabolite, is not ethanol or a fusel alcohol, and is not required for growth under standard conditions. Secondary metabolites are derived from intermediates of many pathways of primary metabolism. These pathways include, without limitation, pathways for biosynthesis of amino acids, the shikimic acid pathway for biosynthesis of aromatic amino acids, the polyketide biosynthetic pathway from acetyl coenzyme A (CoA), the mevalonic acid pathway from acetyl CoA, and pathways for biosynthesis of polysaccharides and peptidopolysaccharides. Collectively, secondary metabolism involves all primary pathways of carbon metabolism. Particularly preferred in embodiments of the aspects of the invention are fungal secondary metabolites (See, *Fungal Physiology*, Chapter 9 (Secondary(Special) Metabolism), Griffin, D. H., John Wiley & Sons, Inc.; ISBN: 0471166154).

"Secondary metabolite" also includes intermediate compounds in the biosynthetic pathway for a secondary metabolite that are dedicated to the pathway for synthesis of the secondary metabolite. "Dedicated to the pathway for synthesis of the secondary metabolite" means that once the intermediate is synthesized by the cell, the cell will not convert the intermediate to a primary metabolite. "Intermediate compounds" also include secondary metabolite intermediate compounds which can be converted to useful compounds by subsequent chemical conversion or subsequent biotransformation. As such, providing improved availability of such intermediate compounds would still lead to improved production of the ultimate useful compound, which itself may be referred to herein as a secondary metabolite. The yeast *Saccharomyces cerevisiae* is not known to produce secondary metabolites.

The term "primary metabolite" means a natural product that has an obvious role in the functioning of almost all organisms. Primary metabolites include, without limitation, compounds involved in the biosynthesis of lipids, carbohydrates, proteins, and nucleic acids. The term "increasing the yield of the secondary metabolite" means increasing the quantity of the secondary metabolite present in the total fermentation broth per unit volume of fermentation broth or culture.

As used herein, the phrase "modulate production of a secondary metabolite" refers to a positive or negative or desirable change in one or more of the variables or values that affect the process or results of production of the primary or secondary metabolites in a liquid or solid state fungal fermentation. These positive or negative or desirable changes include, without limitation, an increase or decrease in the amount of a primary or secondary metabolite being produced (in absolute terms or in quantity per unit volume of fermentation broth or per unit mass of solid substrate); a decrease in the volume of the broth or the mass/quantity of substrate required for the production of sufficient quantities; a decrease in the cost of raw materials and energy, the time of fermentor or culture run, or the amount of waste that must be processed after a fermentor run; an increase or decrease in the specific production of the desired metabolite (both in total amounts and as a fraction of all metabolites and side products made by the fungus); an increase or decrease in the percent of the produced secondary metabolite that can be recovered from the fermentation broth or culture; and an increase in the resistance of an organism producing a primary or secondary metabolite to possible deleterious effects of contact with the secondary metabolite.

In certain embodiments of aspects of the invention, a secondary metabolite is an anti-bacterial. An "anti-bacterial" is a molecule that has cytocidal or cytostatic activity against some or all bacteria. Preferred anti-bacterials include, without limitation, β-lactams. Preferred β-lactams include, without limitation, penicillins and cephalosporins and biosynthetic intermediates thereof. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of aspects of the invention, the secondary metabolite is an anti-hypercholesterolemic or a biosynthetic intermediate thereof. An "anti-hypercholesterolemic" is a drug administered to a patient diagnosed with elevated cholesterol levels for the purpose of lowering the cholesterol levels. Preferred anti-hypercholesterolemics include, without limitation, lovastatin, mevastatin, simvastatin, and pravastatin.

According to other embodiments of the invention, a secondary metabolite is an immunosuppressant or a biosynthetic intermediate thereof. An "immunosuppressant" is a molecule that reduces or eliminates an immune response in a host when the host is challenged with an immunogenic molecule, including immunogenic molecules present on transplanted organs, tissues or cells. Preferred immunosuppressants include, without limitation, members of the cyclosporin family and beauverolide L. Preferred cyclosporins include, without limitation, cyclosporin A and cyclosporin C.

In certain embodiments of aspects of the invention, the secondary metabolite is an ergot alkaloid or a biosynthetic intermediate thereof. An "ergot alkaloid" is a member of a large family of alkaloid compounds that are most often produced in the sclerotia of fungi of the genus Claviceps. An "alkaloid" is a small molecule that contains nitrogen and has basic pH characteristics. The classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocorninine, ergonovine, ergometrinine, and ergoclavine.

In certain embodiments of aspects of the invention, the secondary metabolite is an inhibitor of angiogenesis or a biosynthetic intermediate thereof. An "angiogenesis inhibitor" is a molecule that decreases or prevents the formation of new blood vessels. Angiogenesis inhibitors have proven effective in the treatment of several human diseases including, without limitation, cancer, rheumatoid arthritis, and diabetic retinopathy. Preferred inhibitors of angiogenesis include, without limitation, fumagillin and ovalicin.

In certain embodiments of aspects of the invention, the secondary metabolite is a glucan synthase inhibitor or a biosynthetic intermediate thereof. A "glucan synthase inhibitor" is a molecule that decreases or inhibits the production of 1,3-β-D-glucan, a structural polymer of fungal cell walls. Glucan synthase inhibitors are a class of antifungal agents. Preferred glucan synthase inhibitors include, without limitation, echinocandin B, pneumocandin B, aculeacin A, and papulacandin.

In certain embodiments of aspects of the invention, the secondary metabolite is a member of the gliotoxin family of compounds or a biosynthetic intermediate thereof. The "gliotoxin family of compounds" are related molecules of the epipolythiodioxopiperazine class. Gliotoxins display diverse biological activities, including, without limitation, antimicrobial, antifungal, antiviral, and immunomodulating activities. Preferred members of the "gliotoxin family of compounds" include, without limitation, gliotoxin and aspirochlorine.

In certain embodiments of aspects of the invention, the secondary metabolite is a fungal toxin or a biosynthetic intermediate thereof. A "fungal toxin" is a compound that causes a pathological condition in a host, either plant or animal. Fungal toxins could be mycotoxins present in food products, toxins produced by phytopathogens, toxins from poisonous mushrooms, or toxins produced by zoopathogens. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

With some certain embodiments of aspects of the invention, the secondary metabolite is a modulator of cell surface receptor signaling or a biosynthetic intermediate thereof. The term "cell surface receptor" is as used before. Modulators of cell surface receptor signaling might function by one of several mechanisms including, without limitation, acting as agonists or antagonists, sequestering a molecule that interacts with a receptor such as a ligand, or stabilizing the interaction of a receptor and molecule with which it interacts. Preferred modulators of cell surface signaling include, without limitation, the insulin receptor agonist L-783,281 and the cholecystokinin receptor antagonist asperlicin.

In certain embodiments of aspects of the invention, the secondary metabolite is a plant growth regulator or a biosynthetic intermediate thereof. A "plant growth regulator" is a molecule that controls growth and development of a plant by affecting processes that include, without limitation, division, elongation, and differentiation of cells. Preferred plant growth regulators include, without limitation, cytokinin, auxin, gibberellin, abscisic acid, and ethylene.

In certain embodiments of aspects of the invention, the secondary metabolite is a pigment or a biosynthetic intermediate thereof. A "pigment" is a substance that imparts a characteristic color. Preferred pigments include, without limitation, melanins and carotenoids.

In certain embodiments of aspects of the invention, the secondary metabolite is an insecticide or a biosynthetic intermediate thereof. An "insecticide" is a molecule that is toxic to insects. Preferred insecticides include, without limitation, nodulisporic acid.

In certain embodiments of aspects of the invention, the secondary metabolite is an anti-neoplastic compound or a biosynthetic intermediate thereof. An "anti-neoplastic" compound is a molecule that prevents or reduces tumor formation. Preferred anti-neoplastic compounds include, without limitation, taxol (paclitaxel) and related taxoids.

The phrase "increased activity" is used herein to refer to a characteristic that results in an augmentation of the inherent negative or positive function of the regulatory protein.

The invention provides variant regulator proteins of secondary metabolite production with increased activity and methods of producing the same. The invention further provides for the identification of specific amino acid residues that are important to the functioning of secondary metabolite regulator proteins. By way of non-limiting example, variant regulator proteins of the secondary metabolite regulator lovE are presented herein.

As known to those skilled in the art, certain substitutions of one amino acid for another may be tolerated at one or more amino acid residues of a wild-type regulator protein absent a change in the structure, activity and/or function of the wild-type protein. Such substitutions are referred to in the art as "conservative" substitutions, and amino acids may be categorized into groups that identify which amino acids may be substituted for another without altering the structure and/or function of the protein.

As used herein, the term "conservative substitution" refers to the exchange of one amino acid for another in the same conservative substitution grouping in a protein sequence. Conservative amino acid substitutions are known in the art and are generally based on the relative similarity of the amino acid side-chain substituents, for example, their hydrophobicity, hydrophilicity, charge, size, and the like. In a preferred embodiment, conservative substitutions typically include substitutions within the following groups: Group 1: glycine, alanine, and proline; Group 2: valine, isoleucine, leucine, and methionine; Group 3: aspartic acid, glutamic acid, asparagine, glutamine; Group 4: serine, threonine, and cysteine; Group 5: lysine, arginine, and histidine; Group 6: phenylalanine, tyrosine, and tryptophan. Each group provides a listing of amino acids that may be substituted in a protein sequence for any one of the other amino acids in that particular group.

As stated supra, there are several criteria used to establish groupings of amino acids for conservative substitution. For example, the importance of the hydropathic amino acid index in conferring interactive biological function on a protein is generally understood in the art (Kyte and Doolittle, *Mol. Biol.* 157:105–132 (1982). It is known that certain amino acids may be substituted for other amino acids having a similar hydropathic index or score and still retain a similar biological activity. Amino acid hydrophilicity is also used as a criteria for the establishment of conservative amino acid groupings (see, e.g., U.S. Pat. No. 4,554,101).

Information relating to the substitution of one amino acid for another is generally known in the art (see, e.g., *Introduction to Protein Architecture: The Structural Biology of Proteins*, Lesk, A. M., Oxford University Press; ISBN: 0198504748; *Introduction to Protein Structure*, Branden, C.-I., Tooze, J., Karolinska Institute, Stockholm, Sweden (Jan. 15, 1999); and *Protein Structure Prediction: Methods and Protocols* (*Methods in Molecular Biology*), Webster, D. M. (Editor), August 2000, Humana Press, ISBN: 0896036375).

In one embodiment of the first aspect, the invention provides an improved regulator protein comprising an amino acid sequence coding for a variant of the lovE protein having at least one specific mutation that gives rise to greater transcription-activating properties of the regulator protein and/or increased lovastatin synthesis.

By way of non-limiting example, certain amino acid residues and mutations thereof in the lovE regulatory protein of *A. terreus* (SEQ ID NO:91) are identified by the invention described herein. Mutations at residues 31, 41, 52, 73, 101, 111, 133, 141, 153, 281, 367, and 389 of the wild-type lovE protein of *A. terreus* have been identified as being critical for the improvement of lovE regulator protein function. Those mutations include: F31L, Q41K, Q41R, T52I, T52N, C73R, P101S, P101Q, V111I, S133L, E141V, E141K, C153Y, C153R, T281A, N367I, N367Y, P389S and P389L. Each mutation, therefore, represents a change of one conservative class of amino acids for another. For example, the mutation F31L represents a change from a Group 6 amino acid residue to a Group 2 amino acid residue at position 31 of the wild-type, lovE regulator protein. Other mutations include the mutations described herein, e.g., V17L, H39L, A40T, R76H, H96R, S112P, T119I, P183L, S186R, A204T, the deletion of amino acids 271–373, I283L, L288Q, M299I, E303V, R312K, D314E, the deletion of S316, S317, S318, or S319, T396K, M418L, S421T, L461F, and I467N.

Poor transformation efficiency and the lack of efficient selection systems frequently preclude the screening of large numbers of variant regulator proteins of secondary metabolites in the organism from which the regulator protein is isolated. For example, there are currently certain technical obstacles to the successful screening of large numbers of variant regulator proteins in the fungus *A. terreus*, an organism that produces the secondary metabolite lovastatin.

The invention described herein takes advantage of the genetically tractable and experimentally amenable organism (e.g., *Saccharomyces cerevisiae* and other fungal organisms) for screening large numbers of variant regulator proteins of secondary metabolite production. Techniques common to the field of molecular biology are well developed in *S. cerevisiae*, and large numbers of vectors are available to assist the genetic manipulation and cloning of variant regulator proteins involved in secondary metabolite production. Other genetically tractable organisms could also be used for this purpose.

As used herein, "mutating" is used to refer to the deliberate alteration of at least one nucleotide residue of a wild-type, cognate nucleic acid sequence encoding a regulator protein of secondary metabolite production. A deliberate alteration or change in at least one nucleotide residue of a polynucleotide may be accomplished by any method known in the art. The mutation(s) can be made in vivo or in vitro and can include random, partially random or not random, i.e., directed, mutagenesis techniques.

By way of non-limiting example, in vivo mutagenesis can be done by placing this nucleic acid molecule in a cell with a high mutation frequency, i.e. a mutagenic strain. By way of non-limiting example, Muhlrad et al. (*Yeast* 8:79–82 (1992)) have developed a rapid method for localized mutagenesis of yeast genes. As a first step, the region of interest of a gene sequence is first amplified in vitro under error-prone polymerase chain reaction (PCR) conditions. Error-prone polymerase chain reaction (PCR) is a method of introducing amino acid changes into proteins. With this technique, mutations are deliberately introduced during the PCR reaction through the use of error-prone DNA polymerases under specific reaction conditions. With the Muhlrad et al. procedure, the PCR product is then co-transformed with a gapped plasmid containing homology to both ends of the PCR product, resulting in in vivo recombination to repair the gap with the mutagenized DNA.

There are a variety of commercially available kits that may be used to produce mutant nucleic acid molecules by error-prone PCR (see, e.g., GeneMorph™ PCR Mutagenesis Kit (Stratagene, La Jolla, Calif.); and Diversify™ PCR Random Mutagenesis Kit (BD Biosciences Clontech, Palo Alto, Calif.). Thus, a plurality of variant, i.e., mutated, regulator proteins of secondary metabolite production may be produced using established mutagenesis techniques.

As used herein, the term "activity" refers to a characteristic of the regulator protein that negatively or positively affects the biological system to bring about a modulation in secondary metabolite production. By way of non-limiting example, the activity is the transcription of downstream genes involved in the biosynthetic pathway of the secondary metabolite of choice. Thus, in the present example, the phrase "more activity" refers to the property of a variant regulator protein to bring about more transcription than that effected by the cognate, wild-type regulator protein.

In certain embodiments of the third aspect, the selected variant regulator protein has more activity in a fungal cell than the cognate, wild-type protein. In certain embodiments of the third aspect, the protein regulator of secondary metabolite production is a transcription factor. In certain embodiments of the fourth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain other embodiments of the third aspect, the selected variant regulator protein has more activity in a heterologous cell than the cognate, wild-type protein. In certain embodiments thereof, the heterologous cell is an organism selected from the group consisting of *S. cerevisiae, E. coli, A. nidulans, Candida* sp., and *N. crassa*. In yet certain other embodiments of the third aspect, the selected variant regulator protein has more activity in a homologous cell than the cognate, wild-type protein. In certain embodiments thereof, the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp.,

*Cochliobolus* sp., *Helminthosporium* sp., *Agaricus brunescens, Ustilago maydis, Neurospora* sp., *Pestalotiopsis* sp., and *Phaffia rhodozyma*.

In certain embodiments of the third aspect, the selected variant regulator protein has more activity in a heterologous cell and a homologous cell than the cognate, wild-type protein. In certain embodiments thereof, the heterologous cell is an organism selected from the group consisting of *S. cerevisiae, E. coli, A. nidulans, Candida* sp., and *N. crassa* and the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp. and *Phaffia rhodozyma*.

As used herein, the phrase "heterologous cell" refers to a system for gene expression, i.e., an organism for gene expression, that is one other than the organism from which the selected regulator protein of secondary metabolite production has been isolated. Preferred heterologous cells include, but are not limited to, *S. cerevisiae, E. coli, A. nidulans*, and *Candida* sp., and *N. crassa*. Particularly preferred are fungal heterologous cells. In an embodiment of the third aspect, the method comprises: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; and (c) selecting a mutagenized nucleic acid encoding a variant regulator protein with increased activity in a homologous cell than the cognate, wild-type protein.

As used herein, the phrase "homologous cell" refers to a system for gene expression, i.e., an organism for gene expression, that is the organism from which the regulator protein of secondary metabolite production has been isolated. Preferred homologous cells are fungal homologous cells, including, but not limited to, *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp and *Phaffia rhodozyma*. (See, *Fungal Physiology*, Chapter 9 (Secondary(Special) Metabolism), Griffin, D. H., John Wiley & Sons, Inc.; ISBN: 0471166154).

In certain embodiments of the third aspect, the method further comprises selecting a variant regulator protein that also increases production of a secondary metabolite in a cell when compared to the cognate, wild-type protein. In certain embodiments thereof, the cell is a fungal cell. In certain embodiments thereof, the cell is a heterologous cell, preferably selected from the group consisting of *S. cerevisiae, E. coli, A. nidulans, Candida* sp., and *N. crassa*.

In certain embodiments thereof, the cell is a homologous cell, preferably selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

Certain embodiments of the aspects of the invention relate to regulator proteins that promote secondary metabolite production by increasing transcription of one or more genes involved with secondary metabolite production. These wild-type sequences may be selected for mutagenesis to create a plurality of variant regulator proteins. The activity of these transcription-activating variant regulator proteins may be determined by measuring the activity of a reporter gene having the appropriate promoter sequences. These tests are done in a homologous and/or a heterologous cell. Certain embodiments of aspects of the invention are directed to fungal regulator proteins with transcription-activating activity that is tested in fungal heterologous and homologous cells.

Reporter genes are useful for isolating transformants expressing improved variant regulator proteins. The reporter genes may be operably linked to a promoter sequence that is normally regulated by the wild-type regulator protein. Reporter genes include, but are not limited to, genes encoding β-galactosidase (lacZ), β-glucoronidase (GUS), β-glucosidase, amylase and invertase, amino acid biosynthetic genes, e.g., the yeast LEU2, HIS3, LYS2, TRP1 genes (or homologous genes from other fungi, such as filamentous fungi, that encode proteins with the similar functional activities), nucleic acid biosynthetic genes, e.g., the yeast URA3 and ADE2 genes (or homologous genes from other fungi, such as filamentous fungi, that encode proteins with the similar functional activities), the mammalian chloramphenicol transacetylase (CAT) gene, or any surface antigen gene for which specific antibodies are available. A reporter gene can also be a neomycin phosphotransferase(neo) gene, which encodes neomycin, kanamycin resistance gene, a ble gene, which encodes phleomycin resistance, or a G418 (geneticin) resistance gene. A reporter gene may encode a protein detectable by luminescence or fluorescence, such as green fluorescent protein (GFP). Reporter genes may additionally or alternatively encode any protein that provides a phenotypic marker, for example, a protein that is necessary for cell growth or viability, or a toxic protein that causes cell death. Alternatively, the reporter gene may encode a protein detectable by a color assay leading to the presence or absence of color.

The choice of reporter gene will depend on the type of cell to be transformed. Preferred reporter genes are those that are operable in fungal cells. It is preferable to have two reporter genes within the cell. One reporter gene, when expressed, provides a growth advantage to transformed cells that are expressing the variant regulator protein. This allows for the isolation of such transformants though selective pressures. The other reporter gene provides a colorimetric marker, such as the lacZ gene and its encoded protein, β-galactosidase. Alternatively, the second reporter provides a fluorescent or luminescent marker, such as green fluorescent protein (GFP).

In a fourth aspect, the invention provides a method of increasing production of a secondary metabolite comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) expressing the selected variant regulator protein in a cell, thereby increasing production of the secondary metabolite in the cell. In some embodiments, the selection of the variant regulator the expression of the variant regulator to increase production of the secondary metabolite is performed in the same cell.

In certain embodiments of the fourth aspect, the cell is a fungal cell. In certain embodiments of the fourth aspect, the protein regulator of secondary metabolite production is a transcription factor. In certain embodiments of the fourth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain embodiments of the fourth aspect, the cell is a heterologous cell, preferably selected from the group consisting of *S. cerevisiae, E. coli, A. nidulans, Candida* sp., and *N. crassa*. In certain other embodiments of the fourth aspect, the cell is a homologous cell, preferably selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

In certain other embodiments of the fourth aspect, the cell is a heterologous cell and the method further comprises expressing the variant regulator protein in a homologous cell, thereby increasing secondary metabolite production in the homologous cell. In certain embodiments thereof, the heterologous cell is an organism selected from the group consisting of *S. cerevisiae, E. coli, A. nidulans, Candida* sp., and *N. crassa* and the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp. and *Phaffia rhodozyma*.

In a fifth aspect, the invention provides an isolated variant regulator protein of secondary metabolite production having increased activity compared to a cognate, wild-type protein, made by the process comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) recovering the selected variant regulator protein.

In certain embodiments of the fifth aspect, the variant regulator protein selected has more activity in a fungal cell. In certain embodiments of the fifth aspect, the protein regulator of secondary metabolite production is a transcription factor. In certain embodiments of the fifth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain embodiments of the fifth aspect, the variant regulator protein selected has more activity in a heterologous cell, preferably selected from the group consisting of *S. cerevisiae, E. coli, A. nidulans, Candida* sp., *Neurospora* sp., *Pestalotiopsis* sp., and *N. crassa*. In certain embodiments of the fifth aspect, the variant regulator protein selected has more activity in a homologous cell, preferably selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

In certain embodiments of the fifth aspect, the variant regulator protein selected has more activity in a homologous cell and a heterologous cell. In embodiments thereof, the heterologous cell is an organism selected from the group consisting of *S. cerevisiae, E. coli, A. nidulans, Candida* sp., *Neurospora* sp., *Pestalotiopsis* sp., and *N. crassa* and the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

In yet another embodiment of the fifth aspect, the variant regulator protein is a variant protein of the lovE protein having at least one of the following mutations: (1) a Group 6 amino acid residue mutated to a Group 2 amino acid residue at position 31, for example, the mutation represented by F31L; (2) a Group 3 amino acid residue mutated to a Group 5 amino acid residue at position 41, for example, the mutation represented by Q41K or Q41R; (3) a Group 4 amino acid residue mutated to a Group 2 amino acid residue at position 52, for example, the mutation represented by T52I; (4) a Group 4 amino acid residue mutated to a Group 3 amino acid residue at position 52, for example, the mutation represented by T52N; (5) a Group 4 amino acid residue mutated to a Group 5 amino acid residue at position 73, for example, the mutation represented by C73R; (6) a Group 1 amino acid residue mutated to a Group 4 amino acid residue at position 101, for example, the mutation represented by P101S; (7) a Group 1 amino acid residue mutated to a Group 3 amino acid residue at position 101, for example, the mutation represented by P101Q; (8) a valine amino acid residue mutated to another Group 2 amino acid residue at position 111, for example, the mutation represented by V111I; (9) a Group 4 amino acid residue mutated to a Group 2 amino acid residue at position 133, for example, the mutation represented by S133L; (10) a Group 3 amino acid residue mutated to a Group 2 amino acid residue at position 141, for example, the mutation represented by E141V; (11) a Group 3 amino acid residue mutated to a Group 5 amino acid residue at position 141, for example, the mutation represented by E141K; (12) a Group 4 amino acid residue mutated to Group 6 amino acid residue at position 153, for example, the mutation represented by C153Y; (13) a Group 4 amino acid residue mutated to a Group 5 amino acid residue at position 153, for example, the mutation represented by C153R; (14) a Group 4 amino acid residue mutated to a Group 1 amino acid residue at position 281, for example, the mutation represented by T281A; (15) a Group 3 amino acid residue mutated to a Group 2 amino acid residue at position 367, for example, the mutation represented by N367I; (16) a Group 3 amino acid residue mutated to a Group 6 amino acid residue at position 367, for example, the mutation represented by N367Y; (17) a Group 1 amino acid residue mutated to Group 4 amino acid residue at position 389, for example, the mutation represented by P389S; and/or (18) a Group 1 amino acid residue mutated to a Group 2 amino acid residue at position 389, for example, the mutation represented by P389L; (19) a Group 2 amino acid mutated to a Group 2 amino acid other than V at position 17, for example, the mutation represented by V17L; (20) a Group 5 amino acid mutated to a Group 5 amino acid residue other than H at position 39, for example, the mutation represented by H39L; (21) a Group 1 amino acid residue mutated to a Group 4 amino acid residue at position 40, for example, the mutation represented by A40T; (22) a Group 5 amino acid residue mutated to a Group 5 amino acid residue other than R at position 76, for example, the mutation represented by R76H; (23) a Group 5 amino acid residue mutated to a Group 5 amino acid residue other than H at position 96, for example, the mutation represented by H96R; (24) a Group 4 amino acid residue mutated to a Group 1 amino acid residue at position 112, for example, the mutation represented by S112P; (25) a Group 4 amino acid residue mutated to a Group 2 amino acid residue at position 119, for example, the mutation represented by T119I; (26) a Group 1 amino acid mutated to a Group 2 amino acid residue at position 183, for example, the mutation represented by P183L; (27) a Group 4 amino acid residue mutated to a Group 3 amino acid residue at position 186, for example, the mutation represented by S186R; (28) a Group 1 amino acid residue mutated to a Group 4 amino acid residue at position 204, for example, the mutation represented by A204T; (29) a deletion of amino acids residues 271–373; (30) a Group 2 amino acid residue mutated to a Group 2 amino acid residue other than Ile at position 283, for example, the mutation represented by I283L; (31) a Group 2 amino acid residue mutated to a Group 3 amino acid residue at position 288, for example, the mutation represented by L288Q; (32) a Group 2 amino acid residue mutated to a Group 2 amino acid residue other than Met at position 299, for example, the mutation represented by M299I; (33) a Group 3 amino acid residue mutated to a Group 2 amino acid residue at position 303, for example, the mutation represented by E303V; (34) a Group 5 amino acid residue mutated to a Group 5 amino acid residue other than Arg at position 312, for example, the mutation represented by R312K; (35) a Group 2 amino acid residue mutated to a Group 2 amino acid residue other than Asp at position 314, for example, the mutation represented by D314E; (36) a deletion of Ser at position 316, 317, 318, or 319; (37) a Group 4 amino acid residue mutated to a Group 5 amino acid residue at position 396, for example, the mutation represented by T396K; (38) a Group 2 amino acid residue mutated to a Group 2 amino acid residue other than Met at position 418, for example, the mutation represented by M418L; (39) a Group 4 amino acid residue mutated to a Group 4 amino acid residue other than Ser at position 421, for example, the mutation represented by S421T; (40) a Group 2 amino acid residue mutated to a Group 6 amino acid residue at position 461 for example, the mutation represented by L461F; and (41) a Group 2 amino acid residue mutated to a Group 3 amino acid residue at position 467, for example, the mutation represented by I467N.

In a sixth aspect, the invention provides a fungus having improved lovastatin production made by the process of transforming a fungal cell with a nucleic acid molecule encoding a variant of the lovE protein of the first aspect of the invention. In an embodiment thereof, the nucleic acid molecule is selected from a nucleic acid molecule of the second aspect of the invention.

In a seventh aspect, the invention provides an improved process for making lovastatin comprising transforming a fungal cell with a nucleic acid molecule encoding a variant of the lovE protein of the first aspect of the invention. In an embodiment thereof, the fungal cell is transformed with a nucleic acid molecule of the second aspect of the invention.

International Patent Application PCT/US99/29583 and U.S. Pat. No. 6,391,583 disclose lovastatin production genes. However, these references do not provide a mature lovE cDNA sequence. The invention herein remedies the shortcoming of these references by providing a complete cDNA sequence for the lovE mRNA.

The following examples illustrate the preferred modes of making and practicing the present invention but are not meant to limit the scope of the invention since alternative methods may be utilized to obtain similar results.

EXAMPLES

Example 1

Preparation of Strains and Plasmids

Strain MY2124 was derived from the Sigma 1278b strain background of *S. cerevisiae* and its complete genotype is as follows: MATα/MATα:LEU2 ura3Δ0/ura3α0 leu2Δ0/leu2Δ0 trp1Δ0::hisG/trp1Δ0::hisG his3Δ0::hisG/his3Δ0::hisG ura3Δ0::lovF-HIS3p-neo/ura3Δ0. MY2124 can be constructed by mating *S. cerevisiae* strains MY2112 (MATα ura3Δ0 leu2Δ0 trp1Δ0::hisG his3Δ0::hisG ura3Δ0::lovFp-HIS3p-neo) with MY1555 (matα::LEU2 ura3Δ0 leu2Δ0 trp1Δ0::hisG his3Δ0::hisG) and isolating zygotes. The ura3Δ0::lovFp-HIS3p-neo allele of MY2112 was derived by cotransforming SfiI-linearized plasmid MB2254 with pRS424 (Sikorski and Hieter (1989) *Genetics* 122:19–27) into MY1413 (MATα leu2Δ0 trp1Δ0::hisG his3Δ0::hisG). Transformants were selected on SC-Trp media and subsequently screened for 5-fluoro-orotic acid resistance to identify those transformants containing the ura3Δ0::lovFp-HIS3p-neo allele. Trp⁻ segregants lacking plasmid pRS424 were isolated by growing the strain under non-selective conditions.

The following oligonucleotides were used in the construction of plasmids.

TABLE 2

| Oligonucleotides Utilized For *LovE* Variant Cloning | | |
|---|---|---|
| MO664 | (5'GGCCATGGAGGCCGCTAGCTCGAGTCGACGGCCTAGGTGGCCAGCT3') | (SEQ ID NO: 1) |
| MO665 | (5'GGCCACCTAGGCCGTCGACTCGAGCTAGCGGCCTCCATGGCCGTAC3') | (SEQ ID NO: 2) |
| MO666 | (5'GGCGGCCGCTCTAGAACTAGTCTCGAGGGTACC3') | (SEQ ID NO: 3) |

TABLE 2-continued
Oligonucleotides Utilized For LovE Variant Cloning

| | | |
|---|---|---|
| MO667 | (5'GGTACCCTCGAGACTAGTTCTAGAGCGGCCGCC3') | (SEQ ID NO: 4) |
| MO1794 | (5'CACAGCGGCCGCTCAACCTTCCCATTGGGGC3') | (SEQ ID NO: 5) |
| MO1793 | (5'CACCACTAGTACGCGGGCTGATTCGAC3') | (SEQ ID NO: 6) |
| MO1785 | (5'CACCACTAGTTATACATTATATAAAGTAATGTG3') | (SEQ ID NO: 7) |
| MO1786 | (5'CACAGGATCCGTCATCTTTGCCTTCGTTTATC3') | (SEQ ID NO: 8) |
| MO195 | (5'CGCGGATCCTATTGAACAAGATGGATTGCAC3') | (SEQ ID NO: 9) |
| MO196 | (5'CGCGGATCCTATTGAACAAGATGGATTGCAC3') | (SEQ ID NO: 10) |
| MO841 | (5'ACAAAAAAGCAGGCTCCACAATGGCTGCAGATCAAGGTAT3') | (SEQ ID NO: 11) |
| MO842 | (5'ACAAGAAAGCTGGGTTCATGGAGGAATATTGTTGA3') | (SEQ ID NO: 12) |
| MO2278 | (5'GGGGATCCAATCGAGGTCCACGACCAGT3') | (SEQ ID NO: 13) |
| MO343 | (5'GGGGACAAGTTTGTACAAAAAAGCAGGCT3') | (SEQ ID NO: 14) |
| MO2273 | (5'GGGGATCCGCCAATGGTCCCGTTCAAAC3') | (SEQ ID NO: 15) |
| MO2274 | (5'ACAAGAAAGCTGGGTTCACAGAATGTTTAGCTCAA3') | (SEQ ID NO: 16) |
| MO344 | (5'GGGGACCACTTTGTACAAGAAAGCTGGGT3') | (SEQ ID NO: 17) |
| MO2624 | (5'GCGATGCCCCAAGCGCAAGCTACGCCAATCCAGGG3') | (SEQ ID NO: 18) |
| MO2654 | (5'CGTCGCGCCATTCGCCATTCAGGCTGCGCAACTGT3') | (SEQ ID NO: 19) |
| MO2680 | (5'GGACCTTTGCAGCATAAATTACTATACTTCT3') | (SEQ ID NO: 20) |
| MO2686 | (5'GGCGCGTCCATTCGCCATTCAGGCTGCGCAACTGT3') | (SEQ ID NO: 21) |
| MO2681 | (5'TAAAACTCTTGTTTTCTTCTTTTCTCTAAAT3') | (SEQ ID NO: 22) |
| MO2700 | (5'CAGTGAGCGCGCGTAATACGACTCACTATAGGGCGA3') | (SEQ ID NO: 23) |
| MO2701 | (5'ATACTTCTATAGACACACAAACACAAATACACACAC3') | (SEQ ID NO: 24) |
| MO107 | (5'CGCGGATCCCGTCGTTTTACAAC3') | (SEQ ID NO: 25) |
| MO197 | (5'CCCAAGCTTATTATTTTTGACACCAGACCAA3') | (SEQ ID NO: 26) |
| MO1293 | (5'GGAAGATCTAGCATCGTGGCCAATTTCTTCTAGTTT3') | (SEQ ID NO: 27) |
| MO1294 | (5'ATAAGAATGCGGCCGCTCAACCTTCCCATTGGGGCGTTTGC3') | (SEQ ID NO: 28) |
| MO1787 | (5'CACAGGATCCAGCATTATTAATTTAGTGTGTGTATTT3') | (SEQ ID NO: 29) |
| MO1788 | (5'CACCACTAGTCTCGAGCAGATCCGCCAG3') | (SEQ ID NO: 30) |
| MO1793 | (5'CACCACTAGTACGCGGGCTGATTCGAC3') | (SEQ ID NO: 31) |
| MO1794 | (5'CACAGCGGCCGCTCAACCTTCCCATTGGGGC3') | (SEQ ID NO: 32) |
| MO511 | (5'GGCCATCGATACAAGTTTGTACAAAAAAGCTGAAC3') | (SEQ ID NO: 33) |
| MO540 | (5'GGCGCCCTATTACACCACTTTGTACAAGAAAGC3') | (SEQ ID NO: 34) |
| MO1985 | (5'CACACGTCTCCGGCCTCAACCTTCCCATTGGGGCG3') | (SEQ ID NO: 35) |
| MO1986 | (5'CACACAGATCTCGTGGCCAATTTCTTCTAGTTTGA3') | (SEQ ID NO: 36) |
| MO1992 | (5'CACACGGATCCACAATGTTACGTCCTGTAGAAACCCC3') | (SEQ ID NO: 37) |
| MO1993 | (5'CACAGCGGCCGCTTCATTGTTTGCCTCCCTGCTG3') | (SEQ ID NO: 38) |
| MO316 | (5'GCGGCCGCGGCGCCCGGCCCATGTCAACAAGAAT3') | (SEQ ID NO: 39) |
| MO318 | (5'CCGCGGCCGAGTGGAGATGTGGAGT3') | (SEQ ID NO: 40) |

Plasmid MB2254 contains the lovFp-HIS3p-neo reporter gene flanked by URA3 sequence. First primers MO664 (SEQ ID NO:1) and MO665 (SEQ ID NO:2) were annealed and inserted into the KpnI-SacI sites of plasmid pBluescript II KS (Stratagene,). The resulting vector, MB1038, contains a SalI site in the polylinker. Next, the SpeI-XhoI fragment from pJL164 (Brachmann et al. *Yeast* 14:115–132 (1998)) containing a deletion of the URA3 gene with additional flanking sequences was inserted into the NheI-SalI sites of MB1038 to create MB1053. Primers MO666 (SEQ ID NO:3) and MO667 (SEQ ID NO:4) that contain multiple restriction sites (NotI, XbaI, SpeI, XhoI and KpnI) were then annealed together and ligated into the SmaI site of MB1053 to create MB1054. Next, the following four fragments were combined in MB1054 to obtain plasmid MB2254. The lovF promoter from *A. terreus* genomic DNA was PCR amplified with MO1794 (SEQ ID NO:5) and MO1793 (SEQ ID NO:6) and inserted into MB1054 on a NotI-SpeI fragment. The HIS3 basal promoter from pRS403 (Sikorski and Hieter, *Genetics* 122:19–27 (1989)) was PCR amplified with primers MO1785 (SEQ ID NO:7) and MO1786 (SEQ ID NO:8) and inserted into MB1054 on a SpeI-BamHI fragment. Finally, the neo gene (PCR amplified with MO195 (BamHI) (SEQ ID NO:) and MO196 (EcoRI) (SEQ ID NO:10) from plasmid pYX11 (Xiao and Weaver, *Nucl. Acids Res.* 25:2985–2991 (1997)) and CYC1 terminator sequences (XhoI-KpnI fragment from pRS426-GAL-S (Mumberg, et al., *Nucl. Acids. Res.* 22:5767–5768 (1994)) were first combined in pRS416 (Sikorski and Hieter, *Genetics* 122:19–27 (1989)) and then cut out with BamHI-KpnI and inserted into MB1054 to create MB2254.

The lovFp-HIS3p-neo reporter in MY2124 can confer resistance to the drug geneticin (G418). It was empirically determined that MY2124 (untransformed or transformed with parental plasmids MB2478 (CYC1-lovE/CEN) or MB2848 (CYC1-lovE/At274/CEN) was unable to grow on YPD media supplemented with 100 µg/ml G418. Plasmid MB2478 contains the CYC1 promoter operationally linked to the entire *A. terreus* lovE open reading frame. The CYC1 promoter is a relatively weak promoter and thus the lovE ORF in MB2478 was expressed at low levels. MB2478 was the parental vector plasmid for creating full length lovE variants. Plasmid MB2848 contains the CYC1 promoter operationally linked to a chimeric open reading frame consisting of the *A. terreus* lovE DNA binding domain fused to the carboxy-terminal portion of the At274 gene (U.S. Ser. No. 60/257,431, filed Dec. 22, 2000).

MB2848 was used to create lovE variants in which the DNA binding domain was not mutated. Both MB2478 and MB2848 contain yeast CEN and autonomously replicating sequences and both are maintained at 1–2 copies per cell. In contrast to strains transformed with MB2478 or MB2848, strains transformed with plasmid MB1644 (TEF1-lovE/2 micron) were able to grow on G418-supplemented YPD media. The lovE gene of MB1644 is under control of the constitutively strong *S. cerevisiae* TEF1 promoter. MB1644 contains a 2-micron origin for high-copy replication in yeast. An objective of these studies was to identify lovE variants which when expressed at low levels could confer G418 resistance similar to the highly expressed wild-type lovE molecule of MB1644. *S. cerevisiae* expression vectors used in these studies were constructed as follows.

MB968 is a low copy *S. cerevisiae* URA3 based expression vector. MB968 was created by inserting the EcoRV fragment (containing the destination cassette) from gateway pEZC7201 (Invitrogen™, Carlsbad, Calif.) into XhoI/SalI (filled in with Klenow) linearized pRS416 CYC1 (Mumberg, et al., *Gene* 156:119–122 (1995)).

MB1644 and MB2478 are URA3-based *S. cerevisiae* expression plasmids that contain the wild-type lovE gene. They are both derivatives of MB1199. MB1199 was created by using primers MO841 (SEQ ID NO:11) and MO842 (SEQ ID NO:12) to amplify the lovE ORF from *A. terreus* cDNA. Gateway (Invitrogen™, Carlsbad, Calif.) Cloning Technology (U.S. Pat. No. 5,888,732) was used to clone the lovE PCR fragment into the gateway entry vector pDONR206 (Invitrogen™, Carlsbad, Calif.) to create MB1199. Similarly, Gateway Cloning Technology was used to transfer the lovE ORF from MB1199 into MB968 to create MB2478 and into MB969 (U.S. Ser. No. 60/198,335, filed Apr. 18, 2000) to create MB1644.

MB2848 is a derivative of MB968 that contains a lovE-AT274 chimera. The lovE portion of MB2848 was derived by using oligos MO841 (SEQ ID NO:11) and MO2278 (SEQ ID NO:13) to PCR amplify the lovE DNA binding domain from *A. terreus* cDNA. A second round of PCR was performed with primers MO343 (SEQ ID NO:14) and MO2278 to add appropriate Gateway Cloning Technology compatible sequences. The At274 portion of MB2848 can be derived by using primers MO2273 (SEQ ID NO:15) and MO2274 (SEQ ID NO:16) to PCR amplify the carboxy-terminal domain of At274 from *A. terreus* cDNA. A second round of PCR was performed with primers MO344 (SEQ ID NO:17) and MO2273 to add appropriate Gateway Cloning Technology compatible sequences. The lovE and At274 PCR products were cut with BamHI and purified over a QIAquick PCR purification kit (Qiagen, Valencia, Calif.) according to manufacturer's instructions. Finally, the products were mixed 3–4 hours in a standard ligation reaction and used in Gateway entry and destination reactions to create MB2848.

Gateway cloning technology was used to clone the lovE variants of interest into plasmid MB1419 which is a filamentous fungal expression vector. The MB1419 fungal selection marker is the *A. nidulans* GPD promoter controlling the ble gene from *S. hindustanus*. The transgene is controlled by the *A. nidulans* PGK promoter. *A. terreus* strain MF117 is a derivative of *A. terreus* strain ATCC 20542.

Example 2

PCR Mutagenesis of the lovE DNA Binding Domain

The zinc finger DNA binding domain of lovE is encoded by nucleotides 100–201 (SEQ ID NO:92). Oligos MO2624 (SEQ ID NO:18) and MO2654 (SEQ ID NO:19) were used to PCR amplify a lovE containing fragment from plasmid MB2478. The 1.7 kb product contains nucleotides 212–1410 of lovE and ~500 bp of flanking vector sequence. Two rounds of standard PCR (1.5 mM $MgCl_2$) were performed with Amplitaq DNA polymerase (Applied Biosystems, Foster City, Calif.) according to the manufacturer's instructions.

Plasmid MB2848 was cut with KpnI-BamHI to release a 1.1 kb fragment containing the At274 portion of the lovE-At274 chimeric open reading frame. The remaining 5.5 kb vector sequence retains the lovE DNA binding domain.

Example 3

PCR Mutagenesis of the lovE Open Reading Frame lovE open reading frame insert was prepared according to the following procedure. Oligo pairs MO2680 (SEQ ID NO:20)/MO2686 (SEQ ID NO:21), MO2681 (SEQ ID NO:22)/MO2686, and MO2700 (SEQ ID NO:23)/MO2701 (SEQ ID NO:24) were used to PCR amplify the entire lovE open reading frame from plasmid MB2478. The PCR products differ in the amount of 5' and 3' vector sequence flanking the lovE open reading frame.

PCR was performed using a GeneMorph PCR mutagenesis kit (Stratagene, La Jolla, Calif.) according to manufacturer's instructions to achieve medium and high range mutation frequencies.

Plasmid MB2478 was cut with Asp718/XbaI to release a 1.7 kb fragment. The remaining 5.0 kb vector sequence completely lacks lovE ORF sequence.

gel extraction kit (Qiagen) according to manufacturer's instructions.

The mutagenesis strategy of Muhlrad et al. (*Yeast* 8:79–82 (1992)) was used which involves cotransforming a mutated PCR product and gapped plasmids into *S. cerevisiae*, and then screening for in vivo recombinants having the desired phenotype).

Transformation of *Saccharomyces cerevisiae* was accomplished by the lithium acetate/single-stranded carrier DNA/polyethylene glycol (LiAc/ss-DNA/PEG) protocol (Woods R. A. and Gietz R. D. *Methods Mol. Biol.* 177:85–97 (2001)) with a 1:5 molar ratio of vector:insert DNA to generate >55,000 in vivo recombinant transformants on SC-Ura plates. Transformants were transferred by replica printing to YPD plates containing 100 µg/ml G418 and allowed to grow for 2–4 days at 30° C. (FIG. 1).

Drug resistant clones were confirmed in secondary assays including growth on G418 concentrations up to 2000 µg/ml. The plasmid-dependence of the phenotype was determined by observing the re-appearance of drug sensitivity correlating with loss of the library plasmid. lovE variant plasmids were recovered from promising candidates (Hoffman and Winston (1986) *Gene* 57:267). More than 70 lovE variants were identified and definitively characterized by DNA sequence and/or restriction digestion analysis.

Table 3 summarizes the G418 resistance phenotype and sequence analysis of 26 of these variants.

TABLE 3

Variant lovE Mutations

| lovE allele | lovFp-neo Mediated G418R | MO oligos for used random PCR mutagenesis | Amino Acid Change 1 | Amino Acid Change 2 | Amino Acid Change 3 | Amino Acid Change 4 | Amino Acid Change 5 | Amino Acid Change 6 | Amino Acid Change 7 | Amino Acid Change 8 | Amino Acid Change 9 | Amino Acid Change 10 | Amino Acid Change 11 |
|---|---|---|---|---|---|---|---|---|---|---|---|---|---|
| 1 | −/+ | 2624/2654 | H253R | S341P | | | | | | | | | |
| 2 | +/− | 2824/2654 | R121W | S133L | S322G | | | | | | | | |
| 3 | +++ | 2624/2854 | C73R | A83V | T135I | | | | | | | | |
| 4 | ++ | 2624/2654 | C73R | E177G | | | | | | | | | |
| 5 | ++ | 2624/2854 | C73R | | | | | | | | | | |
| 6 | +/− | 2624/2654 | C153Y | E197K | T281A | | | | | | | | |
| 7 | + | 2624/2654 | C73R | T256A | N466S | | | | | | | | |
| 8 | +++ | 2624/2654 | C73R | E141V | | | | | | | | | |
| 9 | ++ | 2624/2654 | C73R | E303K | | | | | | | | | |
| 10 | +++ | 2624/2654 | Q41K | | | | | | | | | | |
| 16 | +++ | 2680/2686 | Q41K | P16A | G23S | T9M | Q362E | | | | | | |
| 19 | +/− | 2700/2701 | R21H | S34A | Q80H | A84S | E303D | H374D | A440T | A441V | C445S | P469S | |
| 20 | + | 2700/2701 | F31L | T409I | | | | | | | | | |
| 21 | +++ | 2700/2701 | F31L | M97I | E113D | D146N | P163S | N367I | H458Y | | | | |
| 30 | +/− | 2681/2686 | I43V | Q295L | | | | | | | | | |
| 31 | ++ | 2680/2686 | F31L | P101S | C153R | C159S | E162K | R293L | S311N | | | | |
| 32 | ++ | 2680/2680 | L14I | E18V | G138C | E338C | V361L | P389S | N400S | | | | |
| 33 | ++ | 2680/2686 | Q41R | S174Y | A402T | | | | | | | | |
| 34 | ++ | 2680/2686 | F31L | T52I | P101Q | P108S | V111I | | | | | | |
| 35 | +/− | 2700/2701 | D85N | I143F | M232I | T315I | S382Y | M385K | | | | | |
| 37 | ++ | 2700/2701 | T46I | Q62R | K77R | S323C | N367I | V373I | | | | | |
| 36 | +/− | 2700/2701 | Q41R | T294I | P310L | G337D | P389L | A394V | G436S | | | | |
| 39 | + | 2680/2686 | T52N | V111I | T139 | V184I | T281A | | | | | | |
| 40 | +++ | 2680/2686 | Q41R | D4E | V63I | D110E | E141K | A189T | N276D | T347R | N367I | Q377R | A425T |
| 41 | −/+ | 2880/2686 | D131N | D131N | S133L | R312G | A429G | | | | | | |
| wild-Type | − | N/A | N/A | | | | | | | | | | |

Example 4
Transformation and Selection for G418R Isolates

All PCR products were purified using a QIAquick PCR purification kit (Qiagen) according to manufacturer's instructions. All vectors were gel purified using a QIAquick Table 4 summarizes amino acid substitutions that were isolated multiple times, suggesting that they are particularly important for improving lovE variant activity on lovFp-HIS3p-neo expression.

TABLE 4 lovE Mutations Isolated Multiple Times

| Amino Acid Change | Number of Times Isolated in lovE 1–41 | lovE variant |
|---|---|---|
| F31L | 4 | 20, 21, 31, 34 |
| Q41K | 2* | 10, 16 |
| Q41R | 3* | 33, 38, 40 |
| T52I/T52N | 1 each | 34, 39 |
| C73R | 6* | 3, 4, 5, 7, 8, 9 |
| P101S/P101Q | 1 each | 31, 34 |
| V111I | 2 | 34, 39 |
| S133L | 2 | 2, 41 |
| E141V, E141K | 1 each | 8, 40 |
| C153Y/C153R | 1 each | 6, 31 |
| T281A | 2 | 6, 39 |
| N367I/N367Y | 2/1 | 21, 40, 37 |
| P389S/P389L | 1 each | 32, 38 |

*allele was isolated in additional lovE variants that were not fully sequenced

Example 5

Increased lovF-lacZ Expression in *S. cerevisiae*

In order to quantify the increase in lovF expression, β-galactosidase activity was measured in lovE variant transformed *S. cerevisiae* strains that also harbored lovFp-lacZ reporter derivative plasmids. lovF-lacZ reporter derivative plasmids were constructed as follows.

Plasmid MB1918 contains the lovFp-lacZ reporter gene. It can be derived from pRS424 (Sikorski and Hieter (1989) *Genetics* 122:19–27). First, primers MO107 (SEQ ID NO:25) and MO197 (SEQ ID NO:26) are used to PCR amplify the lacZ gene from Yep355 (Myers, et al., *Gene* 45:299–310 (1986)). This lacZ-containing fragment was inserted into the BamHI-HindIII sites of pRS416 (Sikorski and Hieter, *Genetics* 122:19–27 (1989)). This same lacZ fragment can be cut out of the resulting vector with KpnI-NotI and inserted into the same sites of pRS424 to create pRS424-lacZ. Primers MO1293 (SEQ ID NO:27) and MO1294 (SEQ ID NO:28) are used to PCR amplify a 2.09 kb fragment of the lovF promoter from *A. terreus* genomic DNA. The lovF promoter fragment was then cut with NotI-BglII and inserted into NotI-BamHI linearized pRS424-lacZ.

Plasmid MB2114 contains the lovFp-CYC1p-lacZ reporter gene. It can be derived from pRS424-lacZ (see MB1918 plasmid construction). Primers MO1787 (SEQ ID NO:29) and MO1788 (SEQ ID NO:30) are used to amplify the 264 bp basal CYC1 element from pRS415 CYC1 (Mumberg, et al., *Gene* 156:119–122 (1995)). This 264 bp fragment was inserted upstream of the pRS424-lacZ derivative which has been digested with SpeI-BamHI. Finally, the lovF promoter from MB1918 was PCR amplified with MO1793 (SEQ ID NO:31) and MO1794 (SEQ ID NO:32) and inserted into the NotI-SpeI sites to create MB2114.

Yeast strains utilized in this study include strains MY2145 and MY2159, which are both derived from the *S. cerevisiae* sigma 1278b strain background; the genotypes are both strains are as follows: MATa ura3Δ0 leu2Δ0 his3Δ::hisG trp1Δ0::hisG. MY2145 and MY2159 contain the lovFp-lacZ reporter plasmids MB2114 and MB1918, respectively.

MY2124 transformed with individual lovE variant plasmids was mated to *S. cerevisiae* strains MY2154 and MY2159. Diploids were selected on SC-UraTrp media. Multiple diploids from each individual mating were assayed for lovFp-lacZ expression using 96 well format β-galactosidase assays. For β-galactosidase assays, cells were transferred from transformation plates to 96-well microtiter plates containing 200 µl Z buffer. 12 strains were transferred simultaneously using a 12-channel multi-pipettor to scoop cells from transformation plates. Duplicate samples were prepared for all assays. $OD_{600}$ readings were taken on samples in Z buffer. These values were used to normalize for equal cell number in all assays. After determining $OD_{600}$, 150 µl of each sample in Z buffer was transferred onto a Millipore Multiscreen Assay System (Nitrocellulose Immobilon NC), filtered, and then washed by filtering 200 µl Z buffer. 100 µl Z buffer with βME and detergents was then added to each well, as was 20 µl 4 mg/ml ONPG. Reactions were incubated at 30° C., stopped with 50 µl 1 M $Na_2CO_3$, filtered into a polystyrene 96-well assay plate, and $OD_{420}$ was determined for each assay well. β-galactosidase units were determined using the Miller formula (O.D. 420×1000)/(OD600*minutes*volume in mL). Z buffer is made by dissolving the following in 1 L of water (16.1 g $Na_2HPO_4$-$7H_2O$, 5.5 g $NaH_2PO_4$—$H_2O$, 0.75 g KCl and 0.246 g $MgSO_4$-$7H_2O$). Z buffer with detergents and βME is made as follows: 9.8 ml Z buffer, 100 µl 20 mg/ml CTAB, 100 µl 10 mg/ml sodium deoxycholate, and 69 µl βME. Control plasmids utilized in these studies included MB968, MB2478 and MB1644.

Results of these studies are presented in FIGS. 2–5, demonstrating increased transcription-activating properties of the lovE variants disclosed herein.

Example 6

Secondary Metabolite Production

Transformation of filamentous fungi was performed according to the following procedure. Protoplasts were generated by inoculating rich media with spores. Spores were allowed to germinate for about 20 hrs or until germ tubes were between 5 and 10 spore lengths. The germlings were centrifuged and washed twice with sterile distilled water and once with 1 M magnesium sulfate. Germlings were then resuspended in 1M magnesium sulfate containing approximately 2 mg/ml of Novozyme. Tubes were then incubated at 30° C. shaking at 80 RPM for about 2 hrs or until most of the hyphae were digested and protoplasts were abundant. Protoplasts were filtered through one layer of Miracloth. At least one volume of STC was added and protoplasts were centrifuged. Protoplasts were washed twice with STC. Protoplasts then were resuspended in 1 ml STC and counted in a hemacytometer. A final concentration of approximately $5×10^7$ protoplasts/ml were frozen in a 9:1:0.1 solution of STC, SPTC and DMSO in a Nalgene Cryo cooler at −80° C. (cools −1° C./min).

Solutions for transformation were as follows: STC (0.8 M Sorbitol, 25 mM Tris-HCl pH 7.5, 25 mM $CaCl_2$) and SPTC (0.8 M Sorbitol, 40% PEG 4000, 25 mM Tris-HCl pH 8, 50 mM $CaCl_2$). Transformation was accomplished according to the following protocol. 1–5 µg of DNA comprising a lovE variant according to the invention in a fungal expression vector was placed in a 50 ml Falcon tube. 100 µl of previously frozen protoplasts were added to the DNA, gently mixed, and then incubated on ice for 30 min. 15 µl of SPTC was added, followed by mixing by tapping and incubation at RT for 15 min. 500 µl SPTC was added and mixed well by tapping and rolling, then incubated at RT for 15 min. 25 mls of regeneration minimal medium was added, mixed well and poured on plates containing 25 mls of regeneration minimal medium with 2× the concentration of selection drug.

Transformation plates were incubated at 26° C. for 5–6 days or until colonies started to appear. Regeneration minimal medium contains trace elements, salts, 25 mM sodium nitrate, 0.8 M Sucrose, and 1% agarose at pH 6.5. The selection drug that was used successfully with *A. terreus* is phleomycin, a broad-spectrum glycopeptide antibiotic. Transformants were picked onto new plates with a toothpick (if the fungus was sporulating) or with sterile forceps (if the fungus did not sporulate). Purification plates contained minimal medium (same as regeneration minimal medium but containing 2% instead of 0.8 M sucrose) and 1× drug concentration. Picked transformants were incubated at 26° C. for 5–6 days.

Transformants were grown in production media for secondary metabolite production. Briefly, for *A. terreus* and lovastatin production, spores were used as the inoculum. Spores were obtained from the purification plate by using a wooden inoculation stick. The medium was RPM containing corn steep liquor, sodium nitrate, potassium phosphate, magnesium sulfate, sodium chloride, P2000 (Dow chemical), trace elements and lactose or glucose as carbon source. The medium was pH 6.5. Flasks were incubated at 26° C. with shaking at 225 RPM. For static 96-well cultures, the same medium was used and the spores were obtained from the purification plate with a wooden toothpick. 96-well plates were incubated, without shaking at 26° C.

Sampling was done after 5 days for lovastatin. For shake flask experiments 1–1.5 mls of supernatant was placed into 96-well plates, which were centrifuged and supernatants transferred to new 96-well plates. Samples were frozen at −80° C. for storage or for later assays.

Cultures that were grown standing in a 96-well plate were centrifuged and the supernatant was transferred to a new 96 well plate. Samples were frozen at −80° C.

Example 7

Measurement of Secondary Metabolite Production

Figure 6:
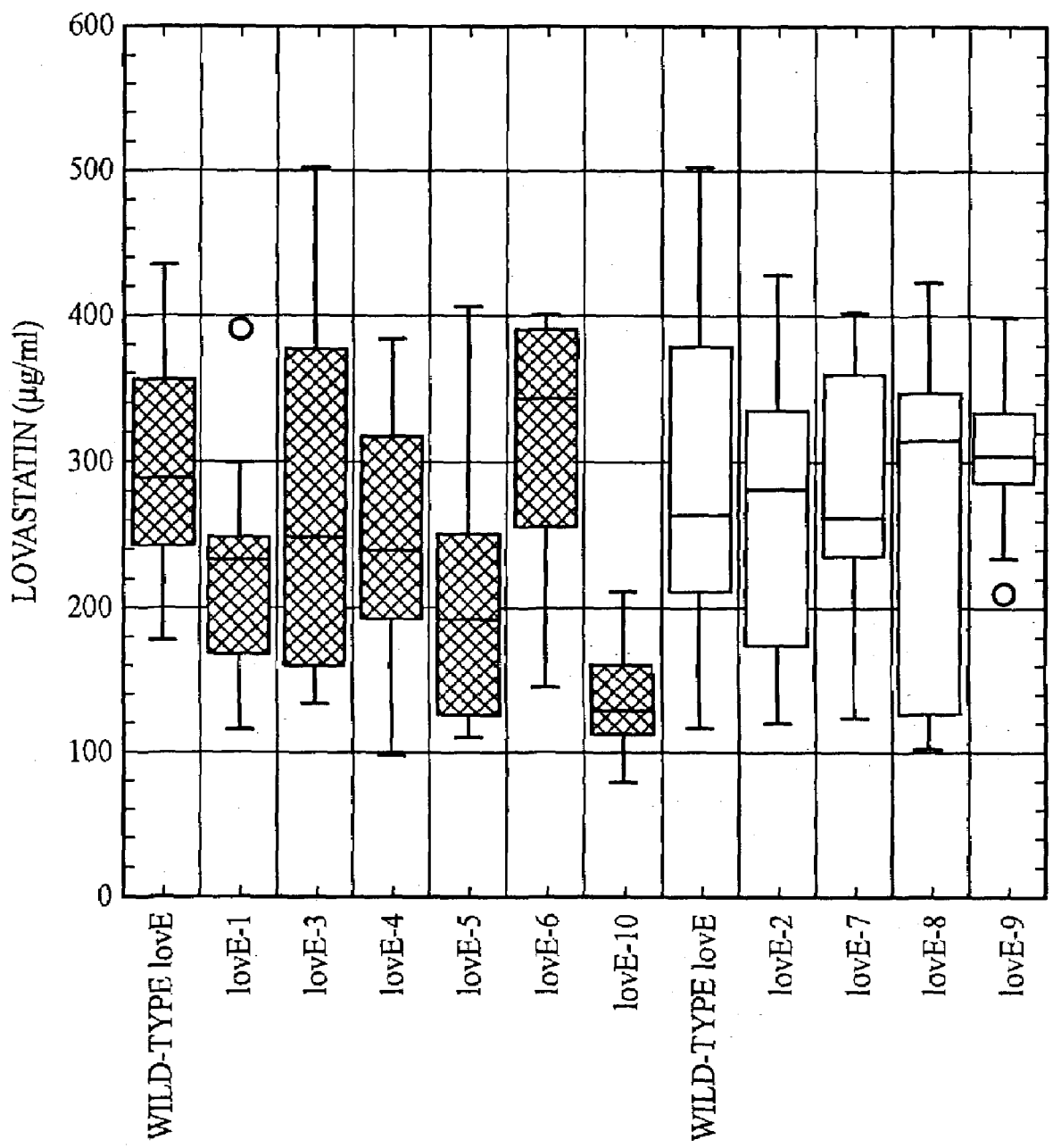
FIG. 6 is a graphic presentation of lovastatin culture concentration, as measured by enzyme inhibition assay, from broths of *A. terreus* cultures expressing lovE variant proteins 1–10.

The concentration of the secondary metabolite lovastatin was determined by enzyme inhibition assay (FIG. 6). Briefly, 10 µL of sample was removed and diluted 1:100 in $H_2O$. 10 µl of this diluted broth was assayed in a reaction (200 µL total) containing 1 mM HMGCoA, 1 mM NADPH, 0.005 mM DTT and 5 µl $(His)_6$HMGR. The disappearance of absorbance at 340 nm was observed over time. This represents the disappearance of NADPH, and lovastatin inhibits this reaction.

The initial velocities were calculated for the reactions containing samples, adjusted for dilution, and compared to reactions containing lovastatin standards to determine levels of metabolite produced. $(His)_6$HMGR was expressed in *Saccharomyces cerevisiae* and purified with a nickel column.

The results from ten individual transformants for each allele are shown in standard box plot format in FIG. 6. Lovastatin concentration from the corresponding wild-type lovE control is shown in matching fill pattern. For example, lovE alleles 2, 7, 8 and 9 were all transformed and assayed at the same time as the non-hatched wild-type control. The horizontal line in each individual box represents the median.

Lovastatin concentration was also determined by high pressure liquid chromatography (HPLC). Briefly, 100 µL of broth sample was removed and diluted 1:10 into 70% $H_2O$-30% acetonitrile (900 µl). This mixture was spun down to pellet debris at 13000 RPM for 5 minutes. 900 µl of this diluted broth was transferred to a vial and the sample was analyzed by HPLC. 10 µl were injected into a Waters HPLC system (996 photo-diode array detector, 600 E pump controller and 717 autosampler) equipped with a YMC-Pack ODS column (Aq-302-3, 150×4.6 mm ID, S-3 µM pore size) and eluted with isocratic 40% aqueous acetic acid (0.7%)-60% acetonitrile for 8 minutes. Lovastatin was detected at 238 nm to have a retention time of 6.5 minutes and was quantified using a calibration curve created from pure lovastatin samples.

Figure 7A:
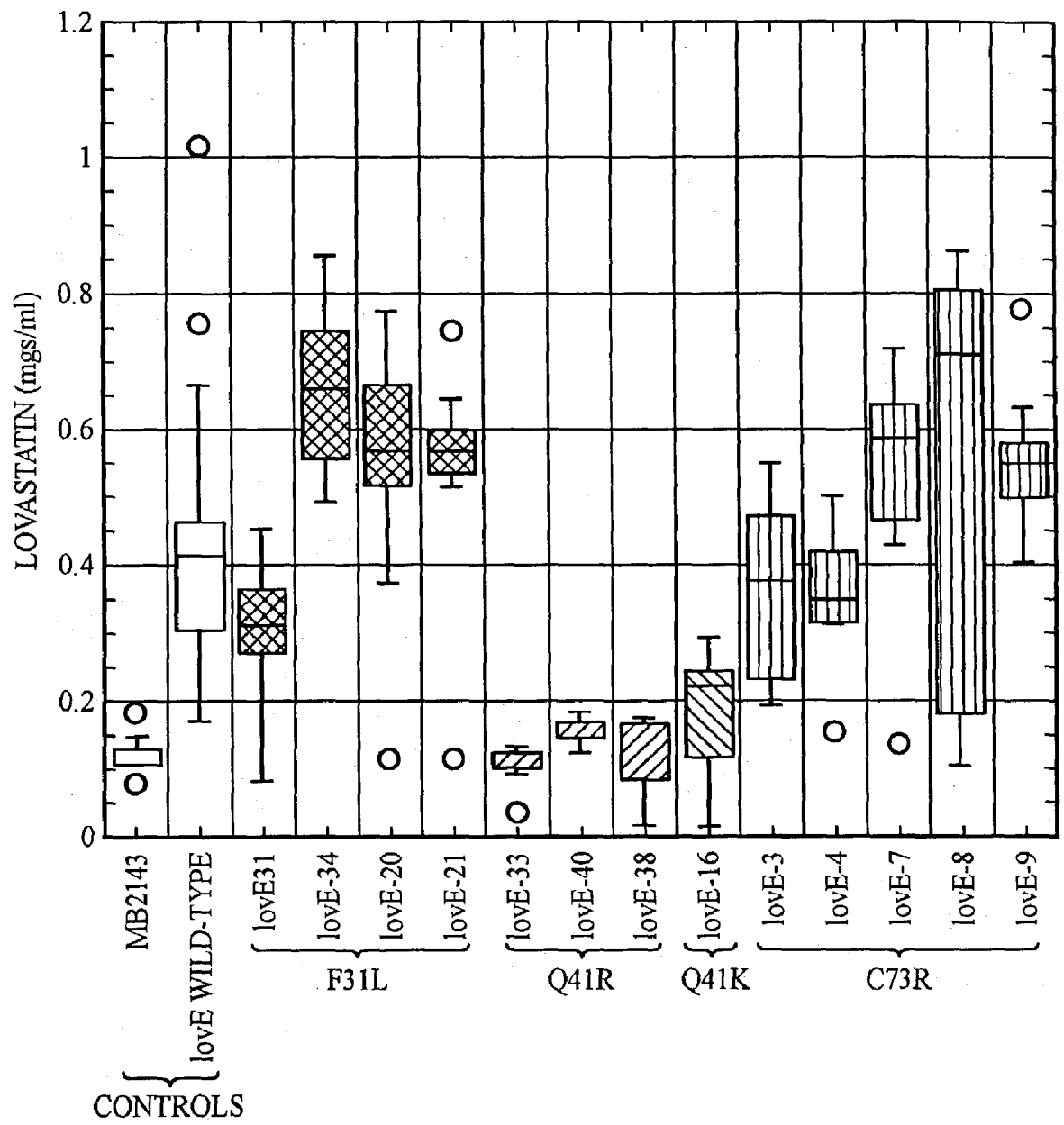
FIG. 7A is a graphic depiction of lovastatin culture concentration, as measured by HPLC analysis, from broths of *A. terreus* cultures expressing lovE variant proteins 1–10 in MF117.
Figure 7B:
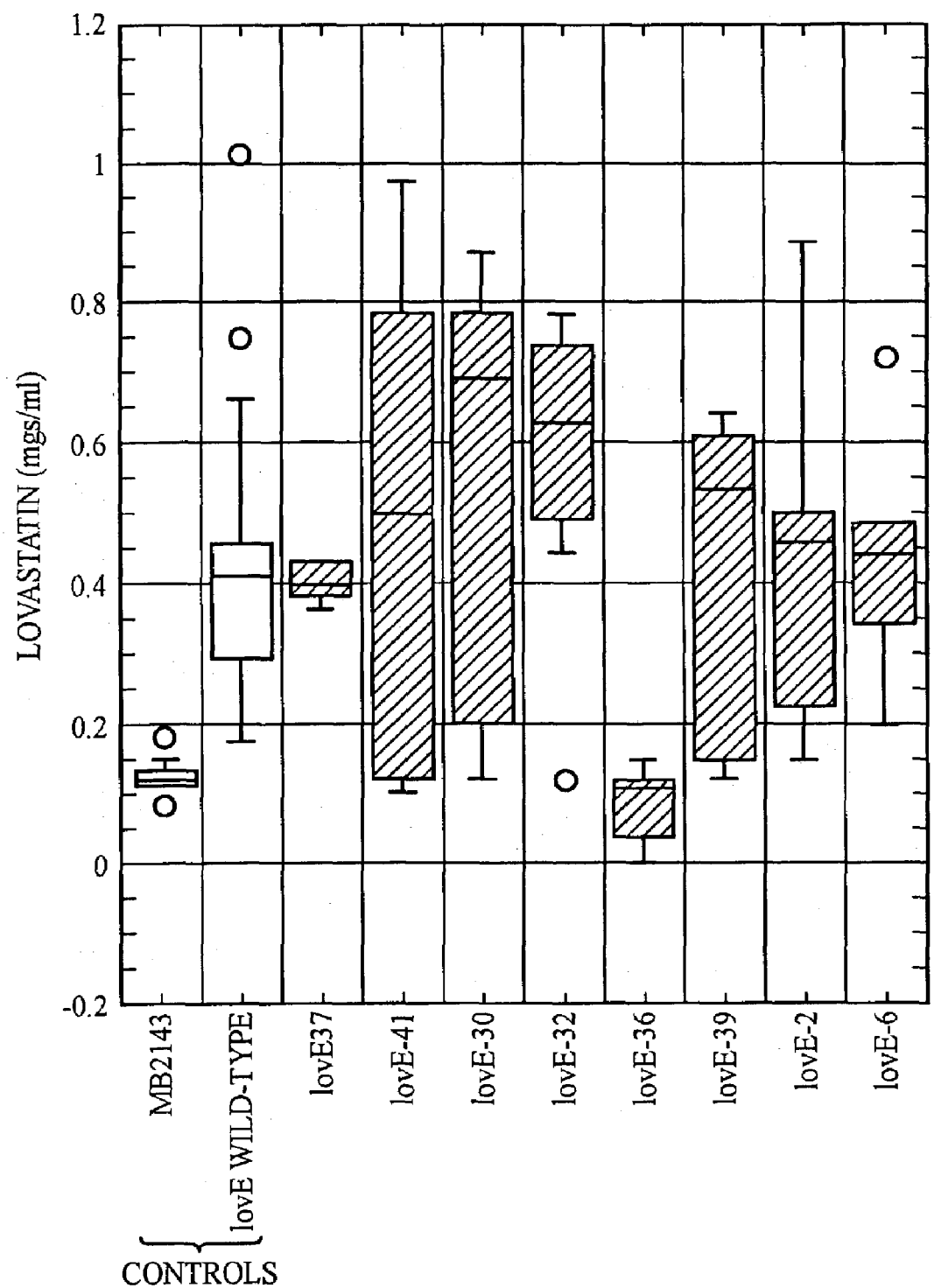
FIG. 7B is a graphic depiction of lovastatin culture concentration, as measured by HPLC analysis, from broths of *A. terreus* cultures expressing lovE variant proteins 2, 6, 30, 32, 36, 37, 39, and 41 in MF117.

The results from ten individual transformants for each lovE variant are shown in standard box plot format in FIGS. 7A and 7B. Thirty individual wild-type lovE transformants and ten individual MB2143 negative control transformants were tested. Identical controls are plotted in FIGS. 7A and 7B.

PCR analysis of *A. terreus* transformants demonstrates that greater than fifty percent of the transformants contain the transgene. Variability in levels of transgene expression can presumably be influenced by integration site and copy number. lovE variants containing identical amino acid substitutions are labeled.

The amino acid and nucleic acid sequences of lovE variant sequences are presented in Table 5 and Table 6, respectively.

Example 8

Isolation of Additional Forms of lovE

An *A. terreus* cDNA was screened to identify sequences that increase expression of a lovF reporter gene in *A. terreus*. This analysis led to the identification of two cDNAs that could encode lovE variants having additional amino acids at their amino terminus compared to the lovE of SEQ ID NO:91. One variant, at242, has the amino sequence mtqdtaqyrga (SEQ ID NO:95) preceding the sequence of SEQ ID NO:91. The entire amino acid sequence of at242 (SEQ ID NO:93) is shown in Table 7. The other variant, at258, has the amino sequence mlmtqdtaqyrga (SEQ ID NO:96) preceding the sequence of SEQ ID NO:91. The entire amino acid sequence of at258 (SEQ ID NO:94) is shown in Table 7. Thus, both variants appear to encode forms of lovE that is longer than the lovE of SEQ ID NO:91. The various amino acid changes present in the various lovE variants of Table 5 can be introduced into the at242 or at258 to generate additional forms of lovE.

Example 9

Generation of Additional lovE Variants

New lovE variants were generated using plasmid MB3048 as a template for mutagenic PCR. MB3048 is a gateway entry plasmid which encodes the at242 form of lovE. The Gene Morph® PCR kit (Stratagene) was used with oligos MO985 (5'TTACCGCTAGCATGGATCTCG3') (SEQ ID NO:115) and MO986 (5'TCTTGTGCAATGTAA-CATCAG3') (SEQ ID NO:116) to generate PCR products containing mutations in the lovE coding sequence. Gateway Cloning Technology® was used to generate an *E. coli* library of mutants in plasmid MB3647. The lovE coding sequences in the MB3647 plasmid are operably linked to the *A. nidulans* PGK promoter. DNA was isolated from the libraries using a Qiagen Maxi® kit and transformed into fungal reporter strains MF186 and MF191. These strains contain the lovF promoter fused to the ble gene which confers resistance to phleomycin (Drocourt et al. *Nucl. Acids Res.* 18:4009, 1990). These strains also contain an endogenous copy of wild type lovE which activates the lovF promoter, and thus are able to grow at phleomycin concentrations of 10 μg/ml or less. Transformants expressing a functional lovE variant should be capable of growing at phleomycin concentrations above 10 μg/ml. Transformants which grew at elevated phleomycin concentrations (concentrations of 75, 150, 300, and 600 μg/ml) were picked to 12 well plates of identical phleomycin concentration, or to minimal plates, grown for 5 days and analyzed for lovastatin production.

Genomic DNA was prepared from selected transformants exhibiting increased phleomycin resistance and PCR-amplified using Pfu polymerase and oligos MO3100 (GAGCTGTATCTGGAAGAGG) (SEQ ID NO:117) and MO3452 (CGTCCATCTCTCTCCGTA) (SEQ ID NO:118), in order to amplify the transfected lovE sequences without amplifying the native, wild type lovE gene. PCR products were introduced into Gateway™ Entry vectors (Invitrogen) via a "BP" reaction and sequenced by established protocols (Seqwright, Inc.). Three clones were identified which contained one PGK-lovE variant (lovE 198, lovE 22409, and lovE 32403A4). In addition, three clones were identified which contained two different PGK-lovE variants in the original isolate (lovE 199-1 and lovE 199-2; lovE 32691A2-1 and lovE 32691A2-2; and lovE 32701C1-1 and lovE 32701C1-2). The amino acid and nucleotide sequences of these variants are shown in Table 5 and Table 6, respectively. The amino acid changes present in each clone are shown in Table 8, below.

Figure 8:
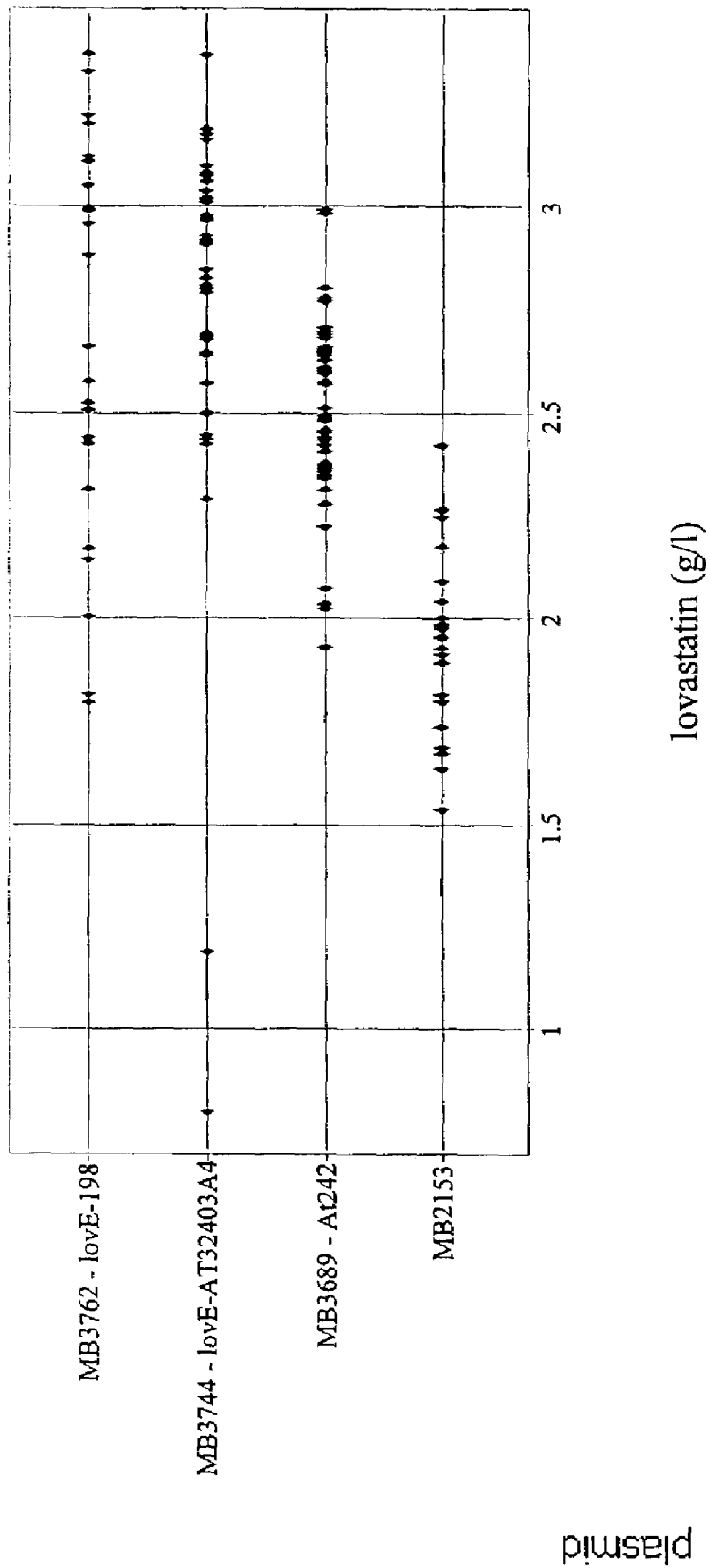
FIG. 8 is a graphic depiction of lovastatin culture concentration, as measured by HPLC analysis, from broths of fungal cultures expressing lovE variant proteins AT32403A4 and 198 in MF172.
Figure 9:
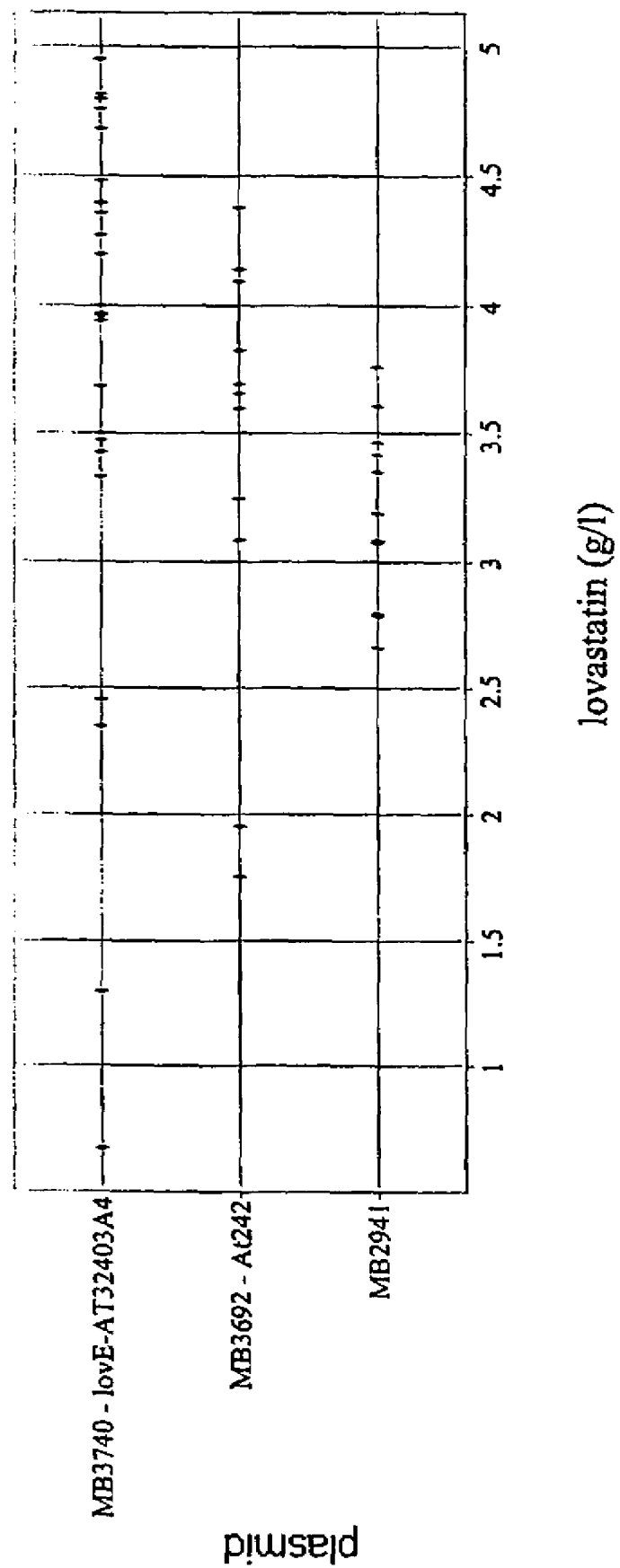
FIG. 9 is a graphic depiction of lovastatin culture concentration, as measured by HPLC analysis, from broths of fungal cultures expressing lovE variant proteins AT32403A4 and 198 in MF172.

The lovE variants were cloned into a Gateway vector and re-transformed into a parental strain of the fungal strain used for selection. Levels of lovastatin production in transformants expressing lovE variants are depicted in FIGS. 8 and 9. Briefly, transformants were cultured and lovastatin levels were assayed by HPLC as described in Example 7, above. FIG. 8 shows lovastatin levels produced by MF172 harboring a vector expressing various lovE variants. Transformants containing empty vector (MB2153) (n=24) produced between 1.5 and 2.4 g/l of lovastatin, with an average production of approximately 2 g/l. Transformants containing the At242 lovE isoform (n=48) produced between 1.8 and 3 g/l of lovastatin, with an average production of approximately 2.5 g/l. Transformants expressing lovE variant AT32403A4 (n=48) produced between 0.8 and 3.4 g/l of lovastatin, with an average of approximately 2.78 g/l. (numbers were changed based on looking at the original data, the scale is every 0.5 not every 1) Transformants expressing the lovE variant 198 (n=24) produced between 1.8 and 3.36 g/l of lovastatin, with an average of approximately 2.6 g/l.

FIG. 9 shows lovastatin levels produced by MF172 harboring a vector expressing various lovE variants. Transformants containing empty vector (n=12) produced between 2.6 and 3.75 g/l of lovastatin, with an average of approximately 3.3 g/l Transformants containing At242 (n=12) produced between 1.75 and 4.4 g/l of lovastatin. Transformants containing lovE variant AT32403A4 (n=24) produced between 0.66 and 5 g/l of lovastatin.

TABLE 8

Variant lovE Mutations

| lovE variant | Amino Acid Change 1 | Amino Acid Change 2 | Amino Acid Change 3 | Amino Acid Change 4 |
|---|---|---|---|---|
| 198 | E303V | | | |
| 199-1 | D314E | T396K | M418L | |
| 199-2 | A40T | M299I | | |
| 22409 | T119I | ΔS316 | S421T | |
| 32403A4 | P183L | I283L | | |
| 32691A2-1 | R76H | H96R | L461F | |
| 32691A2-2 | S186R | L288Q | R312K | |
| 32701C1-1 | S112P | A204T | | |
| 32701C1-2 | V17L | H39L | Δ271–373 | I467N* |

*This mutation is numbered with respect to the position in the original sequence, before the deletion of amino acids 271–373.

TABLE 5

Amino Acid Sequences of Variants of the *lovE* Gene

*lovE-1*

MAADQGIFTNSVTLSPVEGSRTGGTLPRRAFRRSCDRCHAQKIKCTGNKEVTGRAPCQR (SEQ ID NO:41)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCRQGTLDECLRTKNLFTAVHCYILNVRILTAISELLLSQIRRTQ

NSHMSPLEGSRSQSPSRDDTSSSSGHSSVDTIPFFSENLPIGELFPYVDPLTHALFSAC

TTLHVGVQLLRENEITLGVHSAQGIAASISMSGEPGEDIARTGATNSARCEEQPTTPAA

RVLFMFLSDEGAFQEAKSAGSRGRTIAALRRCYEDIFSLARKHKHGMLRDLNNIPP

*lovE-2*

MAADQGIFTNSVTLSPVEGSRTGGTLPRRAFRRSCDRCHAQKIKCTGNKEVTGRAPCQR (SEQ ID NO:42)

CQQAGLRCVYSERCPKRKLRQSRAADLVSADPDPCLHMSSPPVPSQSLPLDVSESHSSN

TABLE 5-continued

Amino Acid Sequences of Variants of the lovE Gene

TSWQFLDPPDSYDWLWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHGSVDTIPFFSENLPIGELFSYVDPLTHALFSAC

TTLHVGVQLLRENEITLGVHSAQGIAASISMSGEPGEDIARTGATNSARCEEQPTTPAA

RVLFMFLSDEGAFQEAKSAGSRGRTIAALRRCYEDIFSLARKHKHGMLRDLNNIPP lovE-3

MAADQGIFTNSVTLSPVEGSRTGGTLPRRAFRRSCDRCHAQKIKCTGNKEVTGRAPCQR (SEQ ID NO:43)

CQQAGLRCVYSERRPKRKLRQSRVADLVSADPDPCLHMSSPPVPSQSLPLDVSESHSSN

TSRQFLDPPDSYDWSWISIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAQGIAASISMSGEPGEDIARTGATNSARCEEQPTTPAA

RVLFMFLSDEGAFQEAKSAGSRGRTIAALRRCYEDIFSLARKHKHGMLRDLNNIPP lovE-4

MAADQGIFTNSVTLSPVEGSRTGGTLPRRAFRRSCDRCHAQKIKCTGNKEVTGRAPCQR (SEQ ID NO:44)

CQQAGLRCVYSERRPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVG

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAWGIAASISMSGEPGEDIARTGATNSARCEEQPTTPAA

RVLFMFLSDEGAFQEAKSAGSRGRTIAALRRCYEDIFSLARKHKHGMLRDLNNIPP lovE-5

MAADQGIFTNSVTLSPVEGSRTGGTLPRRAFRRSCDRCHAQKIKCTGNKEVTGRAPCQR (SEQ ID NO:45)

CQQAGLRCVYSERRPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAQGIAASISMSGEPGEDIARTGATNSARCEEQPTTPAA

RVLFMFLSDEGAFQEAKSAGSRGRTIAALRRCYEDIFSLARKHKHGMLRDLNNIPP lovE-6

MAADQGIFTNSVTLSPVEGSRTGGTLPRRAFRRSCDRCHAQKIKCTGNKEVTGRAPCQR (SEQ ID NO:46)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQYDGGFSCQLEPTLPDLPSPFESTVE

KAPLPPVSSDIARAASAQRKLFDDLSAVSQELEEILLAVTVEWPKQEIWTHPIGMFFNA

TABLE 5-continued

Amino Acid Sequences of Variants of the *lovE* Gene

SRRLLTVLRQQAQADCHQGTLDECLRTKNLFTAVHCYILNVRILAAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAQGIAASISMSGEPGEDIARTGATNSARCEEQPTTPAA

RVLFMFLSDEGAFQEAKSAGSRGRTIAALRRCYEDIFSLARKHKHGMLRDLNNIPP

*lovE-7*

MAADQGIFTNSVTLSPVEGSRTGGTLPRRAFRRSCDRCHAQKIKCTGNKEVTGRAPCQR (SEQ ID NO:47)

CQQAGLRCVYSERRPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQETWTHPIGMFFNA

SRRLLTVLRQQAQADCHQGALDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAQGTAASISMSGEPGEDIARTGATNSARCEEQPTTPAA

RVLFMFLSDEGAFQEAKSAGSRGRTIAALRRCYEDIFSLARKHKHGMLRDLNSIPP

*lovE-8*

MAADQGIFTNSVTLSPVEGSRTGGTLPRRAFRRSCDRCHAQKIKCTGNKEVTGRAPCQR (SEQ ID NO:48)

CQQAGLRCVYSERRPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQETWTHPIGMFFNA

SRRLLTVLRQQAQADCHQGALDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAQGTAASISMSGEPGEDIARTGATNSARCEEQPTTPAA

RVLFMFLSDEGAFQEAKSAGSRGRTIAALRRCYEDIFSLARKHKHGMLRDLNSIPP

*lovE-9*

MAADQGIFTNSVTLSPVEGSRTGGTLPRRAFRRSCDRCHAQKIKCTGNKEVTGRAPCQR (SEQ ID NO:49)

CQQAGLRCVYSERRPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQETWTHPIGMFFNA

SRRLLTVLRQQAQADCHQGALDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TTLHVGVQLLRENEITLGVHSAQGTAASISMSGEPGEDIARTGATNSARCEEQPTTPAA

RVLFMFLSDEGAFQEAKSAGSRGRTIAALRRCYEDIFSLARKHKHGMLRDLNSIPP

*lovE-10*

MAADQGIFTNSVTLSPVEGSRTGGTLPRRAFRRSCDRCHAQKIKCTGNKEVTGRAPCQR (SEQ ID NO:50)

CQQAGLRCVYSERRPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQETWTHPIGMFFNA

SRRLLTVLRQQAQADCHQGALDECLRTKNLFTAVHCYILNVRILTAISELLLSQIRRTQ

NSHMSPLEGSRSQSPSRDDTSSSSGHSSVDTIPFFSENLPIGELFSYVDPLTHALFSAC

TABLE 5-continued

Amino Acid Sequences of Variants of the lovE Gene

TTLHVGVQLLRENEITLGVHSAQGTAASISMSGEPGEDIARTGATNSARCEEQPTTPAA
RVLFMFLSDEGAFQEAKSAGSRGRTIAALRRCYEDIFSLARKHKHGMLRDLNSIPP lovE-16

MAADQGIFMNSVTLSAVEGSRTSGTLPRRAFRRSCDRCHAKKIKCTGNKEVTGRAPCQR (SEQ ID NO:51)
CQQAGLRCVYSERRPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFESTVE
KAPLPPVSSDIARAASAQRELFDDLSAVSQELEEILLAVTVEWPKQETWTHPIGMFFNA
SRRLLTVLRQQAQADCHQGTLDECLRTKNLFTAVHCYILNVRILTAISELLLSQIRRTQ
NSHMSPLEGSRSQSPSRDDTSSSSGHSSVDTIPFFSENLPIGELFSYVDPLTHALFSAC
TTLHVGVQLLRENEITLGVHSAQGTAASISMSGEPGEDIARTGATNSARCEEQPTTPAA
RVLFMFLSDEGAFQEAKSAGSRGRTIAALRRCYEDIFSLARKHKHGMLRDLNSIPP lovE-19

MAADQGIFTNSVTLSPVEGSRTGGTLPRRAFRRSCDRCHAQKIKCTGNKEVTGRAPCQR (SEQ ID NO:52)
CQQAGLRCVYSERRPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFESTVE
KAPLPPVSSDIARAASAQRELFDDLSAVSQELEEILLAVTVEWPKQETWTHPIGMFFNA
SRRLLTVLRQQAQADCHQGTLDECLRTKNLFTAVHCYILNVRILTAISELLLSQIRRTQ
NSHMSPLDGSRSQSPSRDDRSSSSGHSSVDTIPFFSENLPIGELFSYVDPLTHALFSAC
TTLHVGVQLLRENEITLGVHSAQGTAASISMSGEPGEDIARTGATNSARCEEQPTTPAA
RVLFMFLSDEGAFQEAKSAGSRGRTITVLRRSYEDIFSLARKHKHGMLRDLNNIPS lovE-20

MAADQGIFTNSVTLSPVEGSRTGGTLPRRALRRSCDRCHAQKIKCTGNKEVTGRAPCQR (SEQ ID NO:53)
CQQAGLRCVYSERCPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFESTVE
KAPLPPVSSDIARAASAQRELFDDLSAVSQELEEILLAVTVEWPKQETWTHPIGMFFNA
SRRLLTVLRQQAQADCHQGALDECLRTKNLFTAVHCYILNVRILTAISELLLSQIRRTQ
NSHMSPLEGSRSQSPSRDDTSSSSGHSSVDTIPFFSENLPIGELFSYVDPLTHALFSAC
TTLHVGVQLLRENEITLGVHSAQGTAASISMSGEPGEDIARTGATNSARCEEQPTTPAA
TVLFMFLSDEGAFQEAKSAGSRGRTIAALRRCYEDIFSLARKHKHGMLRDLNNIPP lovE-21

MAADQGIFTNSVTLSPVEGSRTGGTLPRRAFRRSCDRCHAQKIKCTGNKEVTGRAPCQR (SEQ ID NO:54)
CQQAGLRCVYSERCPKRKLRQSRAADLVSADPDPCLHISSPPVPSQSLPLDVSDSHSSN
TSRQFLDPPDSYDWSWTSIGTDEAIDTNCWGLSQCDGGFSCQLESTLPDLPSPFESTVE
KAPLPPVSSDIARAASAQRELFDDLSAVSQELEEILLAVTVEWPKQETWTHPIGMFFNA
SRRLLTVLRQQAQADCHQGTLDECLRTKNLFTAVHCYILNVRILTAISELLLSQIRRTQ
NSHMSPLEGSRSQSPSRDDTSSSSGHSSVDTIPFFSENLPIGELFSYVDPLTHALFSAC
TTLHVGVQLLREIEITLGVHSAQGIAASISMSGEPGEDIARTGATNSARCEEQPTTPAA
RVLFMFLSDEGAFQEAKSAGSRGRTIAALRRCYEDIFSLARKHKYGMLRDLNNIPP

TABLE 5-continued

Amino Acid Sequences of Variants of the lovE Gene lovE-30

MAADQGIFTNSVTLSPVEGSRTGGTLPRRAFRRSCDRCHAQKIKCTGNKEVTGRAPCQR (SEQ ID NO:55)
CQQAGLRCVYSERCPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFESTVE
KAPLPPVSSDIARAASAQRELFDDLSAVSQELEEILLAVTVEWPKQEIWTHPIGMFFNA
SRRLLTVLRQQAQADCHQGTLDECLRTKNLFTAVHCYILNVRILTAISELLLSQIRRTT
NSHMSPLEGSRSQSPSRDDTSSSSGHSSVDTIPFFSENLPIGELFPYVDPLTHALFSAC
TTLHVGVQLLRENEITLGVHSAQGIAASISMSGEPGEDIARTGATNSARCEEQPTTPAA
RVLFMFLSDEGAFQEAKSAGSRGRTIAALRRCYEDIFSLARKHKHGMLRDLNNIPPC lovE-31

MAADQGIFTNSVTLSPVEGSRTGGTLPRRAFRRSCDRCHAQKIKCTGNKEVTGRAPCQR (SEQ ID NO:56)
CQQAGLRCVYSERCPKRKLRQSRAADLVSADPDPCLHMSSPPVPSQSLPLDVSESHSSN
TSRQFLDPPDSYDWSWTSIGTDEAIDTDCWGLSQRDGGFSSQLKPTLPDLPSPFESTVE
KAPLPPVSSDIARAASAQRELFDDLSAVSQELEEILLAVTVEWPKQEIWTHPIGMFFNA
SRRLLTVLRQQAQADCHQGTLDECLRTKNLFTAVHCYILNVRILTAISELLLSQIRLTQ
NSHMSPLEGSRSQSPSRDDTSSSSGHSSVDTIPFFSENLPIGELFPYVDPLTHALFSAC
TTLHVGVQLLRENEITLGVHSAQGIAASISMSGEPGEDIARTGATNSARCEEQPTTPAA
TVLFMFLSDEGAFQEAKSAGSRGRTIAALRRCYEDIFSLARKHKHGMLRDLNNIPP lovE-32

MAADQGIFTNSVTISPVVGSRTGGTLPRRAFRRSCDRCHAQKIKCTGNKEVTGRAPCQR (SEQ ID NO:57)
CQQAGLRCVYSERCPKRKLRQSRAADLVSADPDPCLHMSSPPVPSQSLPLDVSESHSSN
TSRQFLDPPDSYDWSWTSICTDEAIDTDCWGLSQCDGGFSCQLEPTLPDLPSPFESTVE
KAPLPPVSSDIARAASAQRELFDDLSAVSQELEEILLAVTVEWPKQEIWTHPIGMFFNA
SRRLLTVLRQQAQADCHQGTLDECLRTKNLFTAVHCYILNVRILTAISELLLSQIRRTQ
NSHMSPLEGSRSQSPSRDDTSSSSGHSSVDTIPFFSENLPIGGLFSYVDPLTHALFSAC
TTLHVGLQLLRENEITLGVHSAQGIAASISMSGESGEDIARTGATSSARCEEQPTTPAA
RVLFMFLSDEGAFQEAKSAGSRGRTIAALRRCYEDIFSLARKHKHGMLRDLNNIPP lovE-33

MAADQGIFTNSVTLSPVEGSRTGGTLPRRAFRRSCDRCHARKIKCTGNKEVTGRAPCQR (SEQ ID NO:58)
CQQAGLRCVYSERCPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFEYTVE
KAPLPPVSSDIARAASAQRELFDDLSAVSQELEEILLAVTVEWPKQEIWTHPIGMFFNA
SRRLLTVLRQQAQADCHQGTLDECLRTKNLFTAVHCYILNVRILTAISELLLSQIRRTQ
NSHMSPLEGSRSQSPSRDDTSSSSGHSSVDTIPFFSENLPIGELFPYVDPLTHALFSAC
TTLHVGVQLLRENEITLGVHSAQGIAASISMSGEPGEDIARTGATNSTRCEEQPTTPAA
RVLFMFLSDEGAFQEAKSAGSRGRTIAALRRCYEDIFSLARKHKHGMLRDLNNIPP lovE-34

MAADQGIFTNSVTLSPVEGSRTGGTLPRRALRRSCDRCHAQKIKCTGNKEVTGRAPCQR (SEQ ID NO:59)
CQQAGLRCVYSERCPKRKLRQSRAADLVSADPDPCLHMSSPQVPSQSLSLDISESHSSN

TABLE 5-continued

Amino Acid Sequences of Variants of the lovE Gene

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIGELFPYVDPLTHALFSAC

TTLHVGVQLLRENEITLGVHSAQGIAASISMSGEPGEDIARTGATNSARCEEQPTTPAA

RVLFMFLSDEGAFQEAKSAGSRGRTIAALRRCYEDIFSLARKHKHGMLRDLNNIPP lovE-36

MAADQGIFTNSVTLSPVEGSRTGGTLPRRAFRRSCDRCHAQKIKCTGNKEVTGRAPCQR (SEQ ID NO:60)

CQQAGLRCVYSERCPKRKLRQSRAANLVSADPDPCLHMSSPPVPSQSLPLDVSESHSSN

TSRQFLDPPDSYDWSWTSIGTDEAFDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIGELFPYVDPLTHALFSAC

TTLHVGVQLLRENEITLGVHSAQGIAASISMSGEPGEDIARTGATNSTRCEEQPTTPAA

RVLFMFLSDEGAFQEAKSAGSRGRTIAALRRCYEDIFSLARKHKHGMLRDLNNIPP lovE-37

MAADQGIFTNSVTLSPVEGSRTGGTLPRRAFRRSCDRCHAQKIKCTGNKEVTGRAPCQR (SEQ ID NO:61)

CQRAGLRCVYSERCPKRRLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSCVDTIPFFSENLPIGELFPYVDPLTHALFSAC

TTLHVGVQLLREYEITLGIHSAQGIAASISMSGEPGEDIARTGATNSTRCEEQPTTPAA

RVLFMFLSDEGAFQEAKSAGSRGRTIAALRRCYEDIFSLARKHKHGMLRDLNNIPP lovE-38

MAADQGIFTNSVTLSPVEGSRTGGTLPRRAFRRSCDRCHARKIKCTGNKEVTGRAPCQR (SEQ ID NO:62)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIDELFSYVDPLTHALFSAC

TTLHVGVQLLRENEITLGVHSAQGIAASISMSGEPGEDIVRTGATNSTRCEEQPTTPAA

RVLFMFLSDEGAFQEAKSAGSRGRTIAALRRCYEDIFSLARKHKHGMLRDLNNIPP lovE-39

MAADQGIFTNSVTLSPVEGSRTGGTLPRRAFRRSCDRCHAQKIKCTGNKEVTGRAPCQR (SEQ ID NO:63)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFEYSVE

KAPLPPVSSDIARAASAQRELFDDLSAVSQELEEILLAVTVEWPKQEIWTHPIGMFFNA

TABLE 5-continued

Amino Acid Sequences of Variants of the lovE Gene

SRRLLTVLRQQAQADCHQGTLDECLRTKNLFTAVHCYILNVRILAAISELLLSQIRRTQ

NSHMSPLEGSRSQSPSRDDTSSSSGHSSVDTIPFFSENLPIGELFPYVDPLTHALFSAC

TTLHVGVQLLRENEITLGVHSAQGIAASISMSGEPGEDIARTGATNSTRCEEQPTTPAA

RVLFMFLSDEGAFQEAKSAGSRGRTIAALRRCYEDIFSLARKHKHGMLRDLNNIPP lovE-40

MAAEQGIFTNSVTLSPVEGSRTGGTLPRRAFRRSCDRCHARKIKCTGNKEVTGRAPCQR (SEQ ID NO:64)

CQQAGLRCVYSERCPKRKLRQSRAADLISADPDPCLHMSSPPVPSQSLPLEVSESHSSN

TSRQFLDPPDSYDWSWTSIGTDKAIDTDCWGLSQCDGGFSCQLEPTLPDLPSPFESTVE

KAPLPPVSSDITRAASAQRELFDDLSAVSQELEEILLAVTVEWPKQEIWTHPIGMFFNA

SRRLLTVLRQQAQADCHQGTLDECLRTKNLFTAVHCYILDVRILTAISELLLSQIRRTQ

NSHMSPLEGSRSQSPSRDDTSSSSGHSSVDTIPFFSENLPIGELFPYVDPLRHALFSAC

TTLHVGVQLLREIEITLGVHSARGIAASISMSGEPGEDIARTGATNSTRCEEQPTTPAA

RVLFMFLSDEGTFQEAKSAGSRGRTIAALRRCYEDIFSLARKHKHGMLRDLNNIPP lov-41

MAADQGIFTNSVTLSPVEGSRTGGTLPRRAFRRSCDRCHAQKIKCTGNKEVTGRAPCQR (SEQ ID NO:65)

CQQAGLRCVYSERCPKRKLRQSRAADLVSADPDPCLHMSSPPVPSQSLPLDVSESHSSN

TSRQFLDPPDSYNWLWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSGDDTSSSSGHSSVDTIPFFSENLPIGELFPYVDPLTHALFSAC

TTLHVGVQLLRENEITLGVHSAQGIAASISMSGEPGEDIARTGATNSTRCEEQPTTPAA

RVLFMFLSDEGAFQEGKSAGSRGRTIAALRRCYEDIFSLARKHKHGMLRDLNNIPP lovE-198

MAADQGIFTNSVTLSPVEGSRTGGTLPRRAFRRSCDRCHAQKIKCTGNKEVTGRAPCQR (SEQ ID NO:97)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLVGSRSQSPSRDDTSSSSGHSSVDTIPFFSENLPIGELFPYVDPLTHALFSAC

TTLHVGVQLLRENEITLGVHSAQGIAASISMSGEPGEDIARTGATNSTRCEEQPTTPAA

RVLFMFLSDEGAFQEAKSAGSRGRTIAALRRCYEDIFSLARKHKHGMLRDLNNIPP lovE-199-1

MAADQGIFTNSVTLSPVEGSRTGGTLPRRAFRRSCDRCHAQKIKCTGNKEVTGRAPCQR (SEQ ID NO:98)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDETSSSSGHSSVDTIPFFSENLPIGELFPYVDPLTHALFSAC

TABLE 5-continued

Amino Acid Sequences of Variants of the lovE Gene

TTLHVGVQLLRENEITLGVHSAQGIAASISMSGEPGEDIARKGATNSTRCEEQPTTPAA

RVLFLFLSDEGAFQEAKSAGSRGRTIAALRRCYEDIFSLARKHKHGMLRDLNNIPP lovE-199-2

MAADQGIFTNSVTLSPVEGSRTGGTLPRRAFRRSCDRCHTQKIKCTGNKEVTGRAPCQR (SEQ ID NO:99)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHISPLEGSRSQSPSRDDTSSSSGHSSVDTIPFFSENLPIGELFPYVDPLTHALFSAC

TTLHVGVQLLRENEITLGVHSAQGIAASISMSGEPGEDIARTGATNSTRCEEQPTTPAA

RVLFMFLSDEGAFQEAKSAGSRGRTIAALRRCYEDIFSLARKHKHGMLRDLNNIPP lovE 22409

MAADQGIFTNSVTLSPVEGSRTGGTLPRRAFRRSCDRCHAQKIKCTGNKEVTGRAPCQR (SEQ ID NO:100)

CQQAGLRCVYSERCPKRKLRQSRAADLVSADPDPCLHMSSPPVPSQSLPLDVSESHSSN

ISRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSSGHSSVDTIPFFSENLPIGELFSYVDPLTHALFSACT

TTLHVGVQLLRENEITLGVHSAQGIAASISMSGEPGEDIARTGATNSTRCEEQPTTPAAR

VLEMFLSDEGAFQEAKSAGSRGRTIAALRRCYEDIFSLARKHKHGMLRDLNNIPP lovE 32404A4

MAADQGIFTNSVTLSPVEGSRTGGTLPRRAFRRSCDRCHAQKIKCTGNKEVTGRAPCQR (SEQ ID NO:101)

CQQAGLRCVYSERCPKRKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPLVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTALSELLLSQIRRTQ

NSHMSPLEGSRSQSPSRDDTSSSSGHSSVDTIPFFSENLPIGELFPYVDPLTHALFSAC

TTLHVGVQLLRENEITLGVHSAQGIAASISMSGEPGEDIARTGATNSTRCEEQPTTPAA

RVLFMFLSDEGAFQEAKSAGSRGRTIAALRRCYEDIFSLARKHKHGMLRDLNNIPP lovE 32691A2-1

MAADQGIFTNSVTLSPVEGSRTGGTLPRRAFRRSCDRCHAQKIKCTGNKEVTGRAPCQR (SEQ ID NO:102)

CQQAGLRCVYSERCPKHKLRQSRAADLVSADPDPCLHMSSPPVPSQSLPLDVSESHSSN

TSRQFLDPPDSYDWSWTSIGTDEAIDTDCWGLSQCDGGFSCQLEPTLPDLPSPFESTVE

KAPLPPVSSDIARAASAQRELFDDLSAVSQELEEILLAVTVEWPKQEIWTHPIGMFFNA

SRRLLTVLRQQAQADCHQGTLDECLRTKNLFTAVHCYILNVRILTAISELLLSQIRRTQ

NSHMSPLEGSRSQSPSRDDTSSSGHSSVDTIPFFSENLPIGELFPYVDPLTHALFSAC

TTLHVGVQLLRENEITLGVHSAQGIAASISMSGEPGEDIARTGATNSTRCEEQPTTPAA

RVLFMFLSDEGAFQEAKSAGSRGRTIAALRRCYEDIFSLARKHKHGMLRDLNNIPP

TABLE 5-continued

Amino Acid Sequences of Variants of the lovE Gene lovE 32691A2-2

MAADQGIFTNSVTLSPVEGSRTGGTLPRRAFRRSCDRCHAQKIKCTGNKEVTGRAPCQR (SEQ ID NO:103)
CQQAGLRCVYSERCPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFESTVE
KAPLPPVSRDIARAASAQRELFDDLSAVSQELEEILLAVTVEWPKQEIWTHPIGMFFNA
SRRLLTVLRQQAQADCHQGTLDECLRTKNLFTAVHCYILNVRILTAISELLLSQIRRTQ
NSHMSPLEGSRSQSPSKDDTSSSSGHSSVDTIPFFSENLPIGELFPYVDPLTHALFSAC
TTLHVGVQLLRENEITLGVHSAQGIAASISMSGEPGEDIARTGATNSTRCEEQPTTPAA
RVLFMFLSDEGAFQEAKSAGSRGRTIAALRRCYEDIFSLARKHKHGMLRDLNNIPP lovE 32701C1-1

MAADQGIFTNSVTLSPVEGSRTGGTLPRRAFRRSCDRCHAQKIKCTGNKEVTGRAPCQR (SEQ ID NO:104)
CQQAGLRCVYSERCPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFESTVE
KAPLPPVSSDIARAASAQRELFDDLSAVSQELEEILLAVTVEWPKQEIWTHPIGMFFNA
SRRLLTVLRQQAQADCHQGTLDECLRTKNLFTAVHCYILNVRILTAISELLLSQIRRTQ
NSHMSPLEGSRSQSPSRDDTSSSSGHSSVDTIPFFSENLPIGELFPYVDPLTHALFSAC
TTLHVGVQLLRENEITLGVHSAQGIAASISMSGEPGEDIARTGATNSTRCEEQPTTPAA
RVLFMFLSDEGAFQEAKSAGSRGRTIAALRRCYEDIFSLARKHKHGMLRDLNNIPP lovE 32701C1-2

MAADQGIFTNSVTLSPLEGSRTGGTLPRRAFRRSCDRCLAQKIKCTGNKEVTGRAPCQR (SEQ ID NO:105)
CQQAGLRCVYSERCPKRKLRQSRAADLVSADPDPCLHMSSPPVPSQSLPLDVSESHSSN
TSRQFLDPPDSYDWSWTSIGTDEAIDTDCWGLSQCDGGFSCQLEPTLPDLPSPFESTVE
KAPLPPVSSDIARAASAQRELFDDLSAVSQELEEILLAVTVEWPKQEIWTHPIGMFFNA
SRRLLTVLRQQAQADCHQGTLDECLRTKNLFTAVHSAQGIAASISMSGEPGEDIARTGA
TNSARCEEQPTTPAARVLFMFLSDEGAFQEAKSAGSRGRTIAALRRCYEDIFSLARKHK
HGMLRDLNNIPP

TABLE 6

DNA Sequences of Variants of the lovE Gene lovE-1

ATGGCTGCAGATCAAGGTATATTCACGAACTCGGTCACTCTCTCGCCAGTGGAGGGTTC (SEQ ID NO:66)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGCTGTCCCAATGTGATGGAGGCTTCA

TABLE 6-continued

DNA Sequences of Variants of the lovE Gene

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

<u>lovE-2</u>

ATGGCTGCAGATCAAGGTATATTCACGAACTCGGTCACTCTCTCGCCAGTGGAGGGTTC (SEQ ID NO:67)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TABLE 6-continued

DNA Sequences of Variants of the lovE Gene

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA lovE-3

ATGGCTGCAGATCAAGGTATATTCACGAACTCGGTCACTCTCTCGCCAGTGGAGGGTTC (SEQ ID NO:68)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA lovE-4

ATGGCTGCAGATCAAGGTATATTCACGAACTCGGTCACTCTCTCGCCAGTGGAGGGTTC (SEQ ID NO:69)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

TABLE 6-continued

DNA Sequences of Variants of the lovE Gene

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA lovE-5

ATGGCTGCAGATCAAGGTATATTCACGAACTCGGTCACTCTCTCGCCAGTGGAGGGTTC (SEQ ID NO:70)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-6

ATGGCTGCAGATCAAGGTATATTCACGAACTCGGTCACTCTCTCGCCAGTGGAGGGTTC (SEQ ID NO:71)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGA
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-7

ATGGCTGCAGATCAAGGTATATTCACGAACTCGGTCACTCTCTCGCCAGTGGAGGGTTC (SEQ ID NO:72)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

<u>lovE-8</u>

ATGGCTGCAGATCAAGGTATATTCACGAACTCGGTCACTCTCTCGCCAGTGGAGGGTTC   (SEQ ID NO:73)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-9

ATGGCTGCAGATCAAGGTATATTCACGAACTCGGTCACTCTCTCGCCAGTGGAGGGTTC (SEQ ID NO:74)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGA
ACGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-10

ATGGCTGCAGATCAAGGTATATTCACGAACTCGGTCACTCTCTCGCCAGTGGAGGGTTC (SEQ ID NO:75)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

<u>lovE-16</u>

ATGGCTGCAGATCAAGGTATATTCACGAACTCGGTCACTCTCTCGCCAGTGGAGGGTTC (SEQ ID NO:76)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

TAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTAGAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-19

ATGGCTGCAGATCAAGGTATATTCACGAACTCGGTCACTCTCTCGCCAGTGGAGGGTTC (SEQ ID NO:77)
ACACACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCATTCCAGGGCATCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCGC
ACTAGACGAATGTTTACGGACCAAGAACCTCTTTACGGCAGTACACTGTTACATATTGA
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
TAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTAGAATTGCTGCGTGAGAATGAGATTACTCTGGGAGTAGA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-20

ATGGCTGCAGATCAAGGTATATTCACGAACTCGGTCACTCTCTCGCCAGTGGAGGGTTC (SEQ ID NO:78)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

*lovE-21*

ATGGCTGCAGATCAAGGTATATTCACGAACTCGGTCACTCTCTCGCCAGTGGAGGGTTC (SEQ ID NO:79)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-30

ATGGCTGCAGATCAAGGTATATTCACGAACTCGGTCACTCTCTCGCCAGTGGAGGGTTC (SEQ ID NO:80)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGA
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-31

ATGGCTGCAGATCAAGGTATATTCACGAACTCGGTCACTCTCTCGCCAGTGGAGGGTTC (SEQ ID NO:81)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA lovE-32

ATGGCTGCAGATCAAGGTATATTCACGAACTCGGTCACTCTCTCGCCAGTGGAGGGTTC (SEQ ID NO:82)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-33

ATGGCTGCAGATCAAGGTATATTCACGAACTCGGTCACTCTCTCGCCAGTGGAGGGTTC (SEQ ID NO:83)
ACGCACCGGTGGAACATTACCCCGCCGTGCATTCCGACGCTCTTGTGATCGGTGTCATG
CACGAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGA
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-34

ATGGCTGCAGATCAAGGTATATTCACGAACTCGGTCACTCTCTCGCCAGTGGAGGGTTC (SEQ ID NO:84)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCAAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

<u>lovE-36</u>

ATGGCTGCAGATCAAGGTATATTCACGAACTCGGTCACTCTCTCGCCAGTGGAGGGTTC (SEQ ID NO:85)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGGCTGTCCCAATGTGATGGAGGCTTCA

GCTGTCAGCTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAT

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTGTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-37

ATGGCTGCAGATCAAGGTATATTCACGAACTCGGTCACTCTCTCGCCAGTGGAGGGTTC (SEQ ID NO:86)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAACGGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCT
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGA
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-38

ATGGCTGCAGATCAAGGTATATTCACGAACTCGGTCACTCTCTCGCCAGTGGAGGGTTC (SEQ ID NO:87)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGTAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

TCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAAGTCGAACCATCGCAGCACTGCGACGATGCTATGAGGATATCTTTTCCCTCG

CCCGCAAACACAAACATGGCATGCTCAGAGACCTCAACAATATTCCTCCATGA

<u>lovE-39</u>

ATGGCTGCAGATCAAGGTATATTCACGAACTCGGTCACTCTCTCGCCAGTGGAGGGTTC (SEQ ID NO:88)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCCCAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CATTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGATATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-40

ATGGCTGCAGAACAAGGTATATTCACGAACTCGGTCACTCTCTCGCCAGTGGAGGGTTC (SEQ ID NO:89)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGTGTCTACAGTGAGCGATGCCCCAAGCGCAAGCTACG
CCAATCCAGGGCAGCGGATCTCATCTCTGCTGACCCAGATCCCTGCTTGCACATGTCCT
CGCCTCCAGTGCCCTCACAGAGCTTGCCGCTAGAAGTATCCGAGTCGCATTCCTCAAAT
ACCTCCCGGCAGTTTCTTGATCCACCGGACAGCTACGACTGGTCGTGGACCTCGATTGG
CACTGACAAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGG
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-41

ATGGCTGCAGATCAAGGTATATTCACGAACTCGGTCACTCTCTCGCCAGTGGAGGGTTC (SEQ ID NO:90)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CACCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGTATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGGAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

<u>lovE-198</u>

ATGGCTGCAGATCAAGGTATATTCACGAACTCGGTCACTCTCTCGCCAGTGGAGGGTTC (SEQ ID NO:106)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGTAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene lovE-199-1

ATGGCTGCAGATCAAGGTATATTCACGAACTCGGTCACTCTCTCGCCAGTGGAGGGTTC (SEQ ID NO:107)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGA
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGAGAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGAAAGGGGCGACCAATTCCGCAAGATGCGAGGAGCAGCCGACCACTCCAGCGGCT
CGGGTTTTGTTCTTGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA lovE-199-2

ATGGCTGCAGATCAAGGTATATTCACGAACTCGGTCACTCTCTCGCCAGTGGAGGGTTC (SEQ ID NO:108)
ACGCACCGGTGGAACATTACCCCGCCGTGCATTCCGACGCTCTTGTGATCGGTGTCATA
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTTGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATAAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

<u>lovE-22409</u>

ATGGCTGCAGATCAAGGTATATTCACGAACTCGGTCACTCTCTCGCCAGTGGAGGGTTC (SEQ ID NO:109)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCATTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCGGCCACAGCAGTGTTGACACCATACCCTTCTTTAGCGAGAACCTCCCTA

TTGGTGAGCTGTTCTCCTATGTTGACCCCCTGACACACGCCCTATTCTCGGCTTGCACT

ACGTTACATGTTGGGGTACAATTGCTGCGTGAGAATGAGATTACTCTGGGAGTACACTC

CGCCCAGGGCATTGCAGCTTCCATCAGCATGAGCGGGGAACCAGGCGAGGATATAGCCA

GGACAGGGGCGACCAATTCCGCAAGATGCGAGGAGCAGCCGACCACTCCAGCGGCTCGG

GTTTTGTTCATGTTCTTGACTGATGAAGGGGCTTTCCAGGAGGCAAAGTCTGCTGGTTC

CCGAGGTCGAACCATCGCAGCACTGCGACGATGCTATGAGGATATCTTTTCCCTCGCCC

GCAAACACAAACATGGCATGCTCAGAGACCTCAACAATATTCCTCCATGA

TABLE 6-continued

DNA Sequences of Variants of the lovE Gene lovE 32403A4

ATGGCTGCAGATCAAGGTATATTCACGAACTCGGTCACTCTCTCGCCAGTGGAGGGTTC (SEQ ID NO:110)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACTGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA lovE 32691A2-1

ATGGCTGCAGATCAAGGTATATTCACGAACTCGGTCACTCTCTCGCCAGTGGAGGGTTC (SEQ ID NO:66)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACTGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGTAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAGAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA lovE 32691A2-2

ATGGCTGCAGATCAAGGTATATTCACGAACTCGGTCACTCTCTCGCCAGTGGAGGGTTC  (SEQ ID NO:112)

ACGCACCGGTGGAACATTACCCCGCCGTGCATTCCGACGCTCTTGTGATCGGTGTCATG

CACAAAAGATCAAATGTACTGGAAATAAGGAGGTTACTGGCCGTGCTCCCTGTCAGCGT

TGCCAGCAGGCTGGACTTCGATGCGTCTACAGTGAGCGATGCCCCAAGCGCAAGCTACG

CCAATCCAGGGCAGCGGATCTCGTCTCTGCTGACCCAGATCCCTGCTTGCACATGTCCT

CGCCTCCAGTGCCCTCACAGAGCTTGCCGCTAGACGTATCCGAGTCGCATTCCTCAAAT

ACCTCCCGGCAGTTTCTTGATCCACCGGACAGCTACGACTGGTCGTGGACCTCGATTGG

CACTGACGAGGCTATTGACACTGACTGCTGGGGCTGTCCCAATGTGATGGAGGCTTCA

GCTGTCAGTTAGAGCCAACGCTGCCGGATCTACCTTCGCCCTTCGAGTCTACGGTTGAA

AAAGCTCCGTTGCCACCGGTATCGAGCGACATTGCTCGTGCGGCCAGTGCGCAACGAGA

GCTTTTCGATGACCTGTCGGCGGTGTCGCAGGAACTGGAAGAGATCCTTCTGGCCGTGA

CGGTAGAATGGCCGAAGCAGGAAATCTGGACCCATCCCATCGGAATGTTTTTCAATGCG

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTGTTACATATTGA

ATGTGCGGATTTTGACCGCCATATCGGAGTTGCTCCTGTCGCAAATTAGGCGGACCCAG

AACAGCCATATGAGCCCACTGGAAGGGAGTCGATCCCAGTCGCCGAGCAAAGACGACAC

CAGCAGCAGCAGCGGCCACAGCAGTGTTGACACCATACCCTTCTTTAGCGAGAACCTCC

CTATTGGTGAGCTGTTCCCCTATGTTGACCCCCTGACACACGCCCTATTCTCGGCTTGC

ACTACGTTACATGTTGGGGTACAATTGCTGCGTGAGAATGAGATTACTCTGGGAGTACA

CTCCGCCCAGGGCATTGCAGCTTCCATCAGCATGAGCGGGGAACCAGGCGAGGATATAG

CCAGGACAGGGGCGACCAATTCCGCAAGATGCGAGGAGCAGCCGACCACTCCAGCGGCT

CGGGTTTTGTTCATGTTCTTGAGTGATGAAGGGGCTTTCCAGGAGGCAAAGTCTGCTGG

TTCCCGAGGTCGAACCATCGCAGCACTGCGACGATGCTATGAGGATATCTTTTCCCTCG

CCCGCAAACACAAACATGGCATGCTCAGAGACCTCAACAATATTCCTCCATGA

TABLE 6-continued

DNA Sequences of Variants of the lovE Gene

<u>lovE 32701C1-1</u>

ATGGCTGCAGATCAAGGTATATTCACGAACTCGGTCACTCTCTCGCCAGTGGAGGGTTC (SEQ ID NO:113)
ACGCACCGGTGGAACATTACCCCGCCGTGCATTCCGACGCTCTTGTGATCGGTGTCATG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG
TCACGACGGCTTCTTACTGTCCTGCGCCAACAAGCGCAGGCCGACTGCCGTCAAGGCAC
ACTAGACGAATGTTTACGGACCAAGAACCTCTTTACGGCAGTACACTGTTACATATTGA
ATGTGCGGATTTTGACCGCCATATCGGAGTTGCTCCTGTCGCAAATTAGGCGGACCCAG
AACAGCCATATGAGCCCACTGGAAGGGAGTCGATCCCAGTCGCCGAGCAGAGACGACAC
CAGCAGCAGCAGCGGCCACAGCAGTGTTGACACCATACCCTTCTTTAGCGAGAACCTCC
CTATTGGTGAGCTGTTCCCCTATGTTGACCCCCTGACACACGCCCTATTCTCGGCTTGC
ACTACGTTACATGTTGGGGTACAATTGCTGCGTGAGAATGAGATTACTCTGGGAGTACA
CTCCGCCCAGGGCATTGCAGCTTCCATCAGCATGAGCGGGGAACCAGGCGAGGATATAG
CCAGGACAGGGGCGACCAATTCCGCAAGATGCGAGGAGCAGCCGACCACTCCAGCGGCT
CGGGTTTTGTTCATGTTCTTGAGTGATGAAGGGGCTTTCCAGGAGGCAAAGTCTGCTGG
TTCCCGAGGTCGAACCATCGCAGCACTGCGACGATGCTATGAGGATATCTTTTCCCTCG
CCCGCAAACACAAACATGGCATGCTCAGAGACCTCAACAATATTCCTCCATGA

<u>lovE 32701C1-2</u>

ATGGCTGCAGATCAAGGTATATTCACGAACTCGGTCACTCTCTCGCCAGTGGAGGGTTC (SEQ ID NO:114)
ACGCACCGGTGGAACATTACCCCGCCGTGCATTCCGACGCTCTTGTGATCGGTGTCTTG
CACAAAAGATCAAATGTACTGGAAATAAGGAGGTTACTGGCCGTGCTCCCTGTCAGCGT
TGCCAGCAGGCTGGACTTCGATGCGTCTACAGTGAGCGATGCCCCAAGCGCAAGCTACG
CCAATCCAGGGCAGCGGATCTCGTCTCTGCTGACCCAGATCCCTGCTTGCACATGTCCT
CGCCTCCAGTGCCCTCACAGAGCTTGCCGCTAGACGTATCCGAGTCGCATTCCTCAAAT
ACCTCCCGGCAGTTTCTTGATCCACCGGACAGCTACGACTGGTCGTGGACCTCGATTGG
CACTGACGAGGCTATTGACACTGACTGCTGGGGGCTGTCCCAATGTGATGGAGGCTTCA
GCTGTCAGTTAGAGCCAACGCTGCCGGATCTACCTTCGCCCTTCGAGTCTACGGTTGAA
AAAGCTCCGTTGCCACCGGTATCGAGCGACATTGCTCGTGCGGCCAGTGCGCAACGAGA
GCTTTTCGATGACCTGTCGGCGGTGTCGCAGGAACTGGAAGAGATCCTTCTGGCCGTGA
CGGTAGAATGGCCGAAGCAGGAAATCTGGACCCATCCCATCGGAATGTTTTTCAATGCG

TABLE 6-continued

DNA Sequences of Variants of the lovE Gene

TCACGACGGCTTCTTACTGTCCTGCGCCAACAAGCGCAGGCCGACTGCCGTCAAGGCAC

ACTAGACGAATGTTTACGGACCAAGAACCTCTTTACGGCAGTACACTCCGCCCAGGGCA

TTGCAGCTTCCATCAGCATGAGCGGGGAACCAGGCGAGGATATAGCCAGGACAGGGGCG

ACCAATTCCGCAAGATGCGAGGAGCAGCCGACCACTCCAGCGGCTCGGGTTTTGTTCAT

GTTCTTGAGTGATGAAGGGGCTTTCCAGGAGGCAAAGTCTGCTGGTTCCCGAGGTCGAA

CCATCGCAGCACTGCGACGATGCTATGAGGATATCTTTTCCCTCGCCCGCAAACACAAA

CATGGCATGCTCAGAGACCTCAACAATAATCCTCCATGA

TABLE 7

Amino Acid Sequence of lovE Variants At242 and At258 lovE at242

MTQDTAQYRGAMAADQGIFTNSVTLSPVEGSRTGGTLPRRAFRRSCDRCHAQKIKCTGN (SEQ ID NO:93)

KEVTGRAPCQRCQQAGLRCVYSERCPKRKLRQSRAADLVSADPDPCLHMSSPPVPSQSL

PLDVSESHSSNTSRQFLDPPDSYDWSWTSIGTDEAIDTDCWGLSQCDGGFSCQLEPTLP

DLPSPFESTVEKAPLPPVSSDIARAASAQRELFDDLSAVSQELEEILLAVTVEWPKQEI

WTHPIGMFFNASRRLLTVLRQQAQADCHQGTLDECLRTKNLFTAVHCYILNVRILTAIS

ELLLSQIRRTQNSHMSPLEGSRSQSPSRDDTSSSSGHSSVDTIPFFSENLPIGELFSYV

DPLTHALFSACTTLHVGVQLLRENEITLGVHSAQGIAASISMSGEPGEDIARTGATNSA

RCEEQPTTPAARVLFMFLSDEGAFQEAKSAGSRGRTIAALRRCYEDIFSLARKHKHGML

RDLNNIPP lovE at258

MLMTQDTAQYRGAMAADQGIFTNSVTLSPVEGSRTGGTLPRRAFRRSCDRCHAQKIKCT (SEQ ID NO:94)

GNKEVTGRAPCQRCQQAGLRCVYSERCPKRKLRQSRAADLVSADPDPCLHMSSPPVPSQ

SLPLDVSESHSSNTSRQFLDPPDSYDWSWTSIGTDEAIDTDCWGLSQCDGGFSCQLEPT

LPDLPSPFESTVEKAPLPPVSSDIARAASAQRELFDDLSAVSQELEEILLAVTVEWPKQ

EIWTHPIGMFFNASRRLLTVLRQQAQADCHQGTLDECLRTKNLFTAVHCYILNVRTLTA

ISELLLSQIRRTQNSHMSPLEGSRSQSPSRDDTSSSSGHSSVDTIPFFSENLPIGELFS

YVDPLTHALFSACTTLHVGVQLLRENEITLGVHSAQGIAASISMSGEPGEDIARTGATN

SARCEEQPTTPAARVLFMFLSDEGAFQEAKSAGSRGRTIAALRRCYEDIFSLARKHKHG

MLRDLNNIPP

EQUIVALENTS

Those skilled in the art will recognize, or be able to ascertain, using no more than routine experimentation, many equivalents to the specific embodiments of the invention described herein. Such equivalents are intended to be encompassed by the following claims.

What is claimed is:

1. An isolated nucleic acid molecule comprising a nucleotide sequence encoding a polypeptide comprising the amino acid sequence of SEQ ID NO:91 having at least one amino acid change selected from the group consisting of:
   (a) a phenylalanine changed to valine, isoleucine, leucine, or methionine at position 31;
   (b) a glutamine changed to lysine, arginine, or histidine at position 41;
   (c) a threonine changed to valine, isoleucine, leucine, or methionine at position 52;
   (d) a threonine changed to aspartic acid, glutamic acid, asparagine, or glutamine at position 52;
   (e) a cysteine changed to lysine, arginine, or histidine at position 73;
   (f) a proline changed to serine, threonine, or cysteine at position 101;
   (g) a proline changed to aspartic acid, glutamic acid, asparagine, or glutamine at position 101;
   (h) a valine changed to isoleucine, leucine, or methionine at position 111;
   (i) a serine changed to valine, isoleucine, leucine, or methionine at position 133;
   (j) a glutamic acid changed to valine, isoleucine, leucine, or methionine at position 141;
   (k) a glutamic acid to lysine, arginine, or histidine at position 141;
   (l) a cysteine changed to phenylalanine, tyrosine, or tryptophan at position 153;
   (m) a cysteine changed to lysine, arginine, or histidine at position 153;
   (n) a threonine changed to glycine, alanine, or proline at position 281;
   (o) an asparagine changed to valine, isoleucine, leucine, or methionine at position 367;
   (p) an asparagine changed to phenylalanine, tyrosine, or tryptophan at position 367;
   (q) a proline changed to serine, threonine, or cysteine at position 389; and
   (r) a proline changed to valine, isoleucine, leucine, or methionine at position 389;
   wherein the polypeptide further comprises the amino acid sequence of SEQ ID NO:95 immediately amino terminal to the amino acid sequence of SEQ ID NO:91.

2. The isolated nucleic acid molecule of claim 1 wherein the polypeptide when expressed in an A. terreus cell harboring a lovF gene increases expression of the lovF gene relative to an otherwise identical cell not expressing the polypeptide.

3. The isolated nucleic acid molecule of claim 1 wherein the polypeptide when expressed in an S. cerevisiae harboring a gene under the control of the A. terreus lovF expression control region increases expression of the gene relative to an otherwise identical cell not expressing the polypeptide.

4. The isolated nucleic acid molecule of claim 1 wherein the polypeptide has fewer than 15 amino acid changes.

5. The isolated nucleic acid molecule of claim 1 wherein the polypeptide has fewer than 11 amino acid changes.

6. The isolated nucleic acid molecule of claim 1 wherein the polypeptide has fewer than 10 amino acid changes.

7. The isolated nucleic acid molecule of claim 1 wherein the polypeptide has fewer than 8 amino acid changes.

8. The isolated nucleic acid molecule of claim 1 wherein the polypeptide has fewer than 5 amino acid changes.

9. The isolated nucleic acid molecule of claim 1 wherein the polypeptide has fewer than 3 amino acid changes.

10. The isolated nucleic acid molecule of claim 1 wherein the polypeptide has one amino acid change.

11. The isolated nucleic acid molecule of claim 1 wherein the polypeptide has an amino acid change selected from the group consisting of: phenylalanine changed to leucine at position 31, glutamine changed to lysine at position 41, glutamine changed to arginine at position 41, threonine changed to isoleucine at position 52, threonine changed to asparagine at position 52, cysteine changed to arginine at position 73, proline changed to serine at position 101, proline changed to glutamine at position 101, valine changed to isoleucine at position 111, seine changed to leucine at position 133, glutamic acid changed to valine at position 141, glutamic acid changed to lysine at position 141, cysteine changed to tyrosine at position 153, cysteine changed to arginine at position 153, threonine changed to alanine at position 281, asparagine changed to isoleucine at position 367, asparagine changed to tyrosine at position 367, proline changed to serine at position 389, and proline changed to leucine at position 389.

12. The isolated nucleic acid molecule of claim 1 comprising a nucleotide sequence selected from the group consisting of: SEQ ID NO:70, SEQ ID NO:75, SEQ ID NO:78, SEQ ID NO:79, SEQ ID NO:81, SEQ ID NO:83, SEQ ID NO:84, SEQ ID NO:86, SEQ ID NO:87, SEQ ID NO:88.

13. The isolated nucleic acid molecule of claim 1 wherein the nucleotide sequence encoding the polypeptide is contiguous.

14. A fungal cell containing a recombinant nucleic acid molecule comprising the nucleic acid molecule of claim 1.

15. The fungal cell of claim 14 wherein the fungus is A. terreus.

16. A method for providing a fungal cell having improved production of lovastatin the method comprising transforming the fungal cell with a nucleic acid molecule of any of claim 1 whereby the fungal cell has increased lovastatin production compared to an otherwise identical fungal cell that has not been so transformed.

17. A method for producing lovastatin, the method comprising providing a fungal cell containing the nucleic acid molecule of any of claim 1, culturing the cell under conditions so as to produce lovastatin, and isolating from the cells a fraction containing lovastatin.

18. An isolated nucleic acid molecule comprising a nucleotide sequence encoding a polypeptide comprising the amino acid sequence of SEQ ID NO: 91 having at least one amino acid change selected from the group consisting of:
   (a) a valine changed to isoleucine, leucine, or methionine at position 17;
   (b) a histidine changed to lysine or alanine at position 39;
   (c) an alanine changed to seine, threonine, or cysteine at position 40;
   (d) an arginine changed to lysine or histidine at position 76;
   (e) a histidine changed to lysine or arginine at position 96;
   (f) a seine changed to glycine, alanine, or proline at position 112;
   (g) a threonine changed to valine, isoleucine, leucine, or methionine at position 119;
   (h) a proline changed to valine, isoleucine, leucine, or methionine at position 183;
   (i) a serine changed to aspartic acid, glutamic acid, asparagine, or glutamine at position 186;
   (j) an alanine changed to serine, threonine, or cysteine at position 204;
   (k) a deletion of amino acids residues 271–373;
   (l) an isoleucine changed to valine, leucine, or methionine at position 283;
   (m) a leucine changed to aspartic acid, glutamic acid, asparagine, or glutamine at position 288;
   (n) a methionine changed to valine, isoleucine, or leucine at position 299;
   (o) a glutamic acid changed to valine, isoleucine, leucine, or methionine at position 303;
   (p) an arginine changed to lysine or histidine at position 312;
   (q) an aspartic acid changed to valine, isoleucine, leucine, or methionine at position 314;
   (r) a deletion of serine at position 316, 317, 318, or 319;
   (s) a threonine changed to lysine, arginine, or histidine at position 396;
   (t) a methionine changed to valine, isoleucine, or leucine at position 418;
   (u) a serine changed to threonine or cysteine at position 421;
   (v) a leucine changed to phenylalanine, tyrosine, or tryptophan at position 461; and
   (w) an isoleucine changed to aspartic acid, glutamic acid, asparagine, or glutamine at position 467.

19. The isolated nucleic acid molecule of claim 18 wherein the polypeptide when expressed in an *A. terreus* cell harboring a lovF gene increases expression of the lovF gene relative to an otherwise identical cell not expressing the polypeptide.

20. The isolated nucleic acid molecule of claim 18 wherein the polypeptide when expressed in an *S. cerevisiae* cell-harboring a gene under the control of the *A. terreus* lovF expression control region increases expression of the gene relative to an otherwise identical cell not expressing the polypeptide.

21. The isolated nucleic acid molecule of claim 18 wherein the polypeptide has fewer than 11 amino acid changes.

22. The isolated nucleic acid molecule of claim 18 wherein the polypeptide has fewer than 10 amino acid changes.

23. The isolated nucleic acid molecule of claim 18 wherein the polypeptide has fewer than 8 amino acid changes.

24. The isolated nucleic acid molecule of claim 18 wherein the polypeptide has fewer than 5 amino acid changes.

25. The isolated nucleic acid molecule of claim 18 wherein the polypeptide further comprises the amino acid sequence of SEQ ID NO: 95 immediately amino terminal to the amino acid sequence of SEQ ID NO: 91.

26. The isolated nucleic acid molecule of claim 18 wherein the polypeptide further comprises the amino acid sequence of SEQ ID NO: 96 immediately amino terminal to the amino acid sequence of SEQ ID NO: 91.

27. A fungal cell containing a recombinant nucleic acid molecule comprising the nucleic acid molecule of claim 18.

28. A method for providing a fungal cell having improved production of lovastatin, the method comprising transforming the fungal cell with a nucleic acid molecule of claim 18, whereby the fungal cell has increased production of lovastatin compared to an otherwise identical fungal cell that has not been so transformed.

29. A method for producing lovastatin, the method comprising providing a fungal cell containing the nucleic acid molecule of claim 18 and culturing the cell under conditions so as to produce lovastatin.

30. The method of claim 29 further comprising isolating a fraction comprising lovastatin from either the cell or the media in which the cell was cultured.

31. The method of claim 29 further comprising measuring the level of lovastatin in the media in which the cell was cultured.

32. A plasmid comprising a nucleic acid according to of claim 1 or 18.

33. The isolated nucleic acid molecule of claim 18 wherein the polypeptide has one of the following amino acid changes:
   (a) valine changed to leucine at position 17;
   (b) histidine changed to leucine at position 39;
   (c) alanine changed to threonine at position 40;
   (d) arginine changed to histidine at position 76;
   (e) histidine changed to arginine at position 96;
   (f) serine changed to proline at position 112;
   (g) threonine changed to isoleucine at position 119;
   (h) proline changed to leucine at position 183;
   (i) seine changed to arginine at position 186:
   (j) alanine changed to threonine at position 204;
   (k) a deletion of amino acids 271–373;
   (l) isoleucine changed to leucine at position 283:
   (m) leucine changed to glutamine at position 288;
   (n) methionine changed to isoleucine at position 299:
   (o) glutamic acid changed to valine at position 303:
   (p) arginine changed to lysine at position 312;
   (q) aspartic acid changed to glutamic acid at position 314;
   (r) a deletion of serine 316, serine 317, serine 318, or serine 319;
   (s) threonine changed to lysine at position 396;
   (t) methionine changed to leucine at position 418;
   (u) serine changed to threonine at position 421:
   (v) leucine changed to phenylalanine at position 461; and
   (w) isoleucine changed to asparagine at position 467.

34. The isolated nucleic acid molecule of claim 33 wherein the polypeptide has two of the amino acid changes.

35. The isolated nucleic acid molecule of claim 33 wherein the polypeptide has two of the following amino acid changes:
(a) aspartic acid changed to glutamic acid at position 314;
(b) threonine changed to lysine at position 396; and
(c) methionine changed to leucine at position 418.

36. The isolated nucleic acid molecule of claim 33 wherein the polypeptide has two of the following amino acid changes:
(a) threonine changed to isoleucine at position 119;
(b) a deletion of serine 316, serine 317, serine 388, or serine 319; and
(c) serine changed to threonine at position 421.

37. The isolated nucleic acid molecule of claim 33 wherein the polypeptide has two of the following amino acid changes:
(a) arginine changed to histidine at position 76;
(b) histidine changed to arginine at position 96: and
(c) leucine changed to phenylalanine at position 461.

38. The isolated nucleic acid molecule of claim 33 wherein the polypeptide has two of the following amino acid changes:
(a) serine changed to alanine at position 186:
(b) leucine changed to glutamine at position 288; and
(c) arginine changed to lysine at position 312.

39. The isolated nucleic acid molecule of claim 33 wherein the polypeptide has two of the following amino acid changes:
(a) valine changed to leucine at position 17;
(b) histidine changed to leucine at position 39;
(c) a deletion of amino acids 271–373; and
(d) isoleucine changed to asparagine at position 467.

40. The isolated nucleic acid molecule of claim 33 wherein the polypeptide has three of the following amino acid changes:
(a) valine changed to leucine at position 17;
(b) histidine changed to leucine at position 39;
(c) a deletion of amino acids 271–373; and
(d) isoleucine changed to asparagine at position 467.

41. The isolated nucleic acid molecule of claim 33 comprising a nucleotide sequence selected from the group consisting of: SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105.

42. The isolated nucleic acid molecule of claim 33 wherein the nucleotide sequence encoding the polypeptide is contiguous.

43. An isolated nucleic acid molecule comprising a nucleotide sequence encoding a polypeptide comprising SEQ ID NO:93.

44. A fungal cell containing a recombinant nucleic acid molecule comprising the nucleic acid molecule of claim 43.

45. The fungal cell of claim 44 or 27 wherein the fungus is *A. terreus*.

46. The fungal cell of claim 44 or 27 wherein the fungus is *S. cerevisiae*.

* * * * *